(12) United States Patent
Karnieli

(10) Patent No.: US 11,859,163 B2
(45) Date of Patent: Jan. 2, 2024

(54) METHOD OF USING A BIOREACTOR

(71) Applicant: ADVA Biotechnology Ltd., Kiryat Tivon (IL)

(72) Inventor: Ohad Karnieli, Kiryat Tivon (IL)

(73) Assignee: ADVA Biotechnology Ltd., Kiryat Tivon (IL)

( * ) Notice: Subject to any disclaimer, the term of this patent is extended or adjusted under 35 U.S.C. 154(b) by 0 days.

(21) Appl. No.: 18/049,110

(22) Filed: Oct. 24, 2022

(65) Prior Publication Data

US 2023/0099216 A1  Mar. 30, 2023

Related U.S. Application Data

(63) Continuation of application No. 16/325,389, filed as application No. PCT/IL2017/050927 on Aug. 21, 2017, now Pat. No. 11,549,090.

(60) Provisional application No. 62/489,065, filed on Apr. 24, 2017, provisional application No. 62/377,628, filed on Aug. 21, 2016.

(51) Int. Cl.
    *C12M 1/00* (2006.01)
    *C12M 1/34* (2006.01)
    *C12M 1/36* (2006.01)

(52) U.S. Cl.
    CPC ........... *C12M 23/34* (2013.01); *C12M 29/14* (2013.01); *C12M 29/18* (2013.01); *C12M 41/12* (2013.01); *C12M 41/40* (2013.01); *C12M 41/42* (2013.01); *C12M 41/48* (2013.01); *C12M 21/00* (2013.01)

(58) Field of Classification Search
    CPC ...... C12M 23/34; C12M 29/14; C12M 29/18; C12M 41/12; C12M 41/40; C12M 41/42; C12M 41/48; C12M 21/00
    See application file for complete search history.

(56) References Cited

U.S. PATENT DOCUMENTS

| | | | |
|---|---|---|---|
| 4,839,046 A | 6/1989 | Chandler | |
| 4,978,616 A | 12/1990 | Dean, Jr. et al. | |
| 5,187,095 A * | 2/1993 | Bliem | C12M 23/34 435/299.1 |

(Continued)

FOREIGN PATENT DOCUMENTS

| | | |
|---|---|---|
| CN | 201241144 Y | 5/2009 |
| CN | 103849567 A | 11/2014 |

(Continued)

OTHER PUBLICATIONS

International Search Report for PCT Application No. PCT/IL2017/050927 dated Dec. 28, 2017.

*Primary Examiner* — William H. Beisner
*Assistant Examiner* — Danielle B Henkel
(74) *Attorney, Agent, or Firm* — Greenberg Traurig, LLP

(57) ABSTRACT

An inverted conical bioreactor is provided for growing cells or microorganisms. The bioreactor has an internal space and a perforated barrier within the vessel, through which a liquid may flow, where cells or microorganisms cannot pass through the perforated barrier. The perforated barrier divides the internal space of the bioreactor into a first chamber and a second chamber. Cells are grown within the second chamber and can be perfused by re-circulating the liquid, for example a growth medium, through the bioreactor. Various inlet ports and outlet ports allow controlling the parameters of flow of the growth medium.

30 Claims, 21 Drawing Sheets

(56) References Cited

U.S. PATENT DOCUMENTS

| | | |
|---|---|---|
| 6,607,910 B1 | 8/2003 | Dimitrijevich et al. |
| 6,670,169 B1 | 12/2003 | Schob et al. |
| 6,864,084 B2 | 3/2005 | Schob |
| 8,137,959 B2 | 3/2012 | Castillo Fernandez |
| 8,597,939 B2 | 12/2013 | Castillo Fernandez |
| 8,835,159 B2 | 9/2014 | Harvey et al. |
| 9,677,038 B2 | 6/2017 | Stobbe |
| 10,351,824 B2 | 7/2019 | Rooney et al. |
| 10,364,413 B2 | 7/2019 | Shaaltiel et al. |
| 10,392,593 B2 * | 8/2019 | Kasuto ............... C12M 25/14 |
| 11,155,784 B2 | 10/2021 | Rooney et al. |
| 11,549,090 B2 * | 1/2023 | Karnieli ............. C12M 41/40 |
| 2004/0132175 A1 | 7/2004 | Vetillard et al. |
| 2005/0135984 A1 | 6/2005 | Ferron et al. |
| 2007/0134790 A1 | 6/2007 | Gould et al. |
| 2007/0166817 A1 | 7/2007 | Wilkes et al. |
| 2008/0227190 A1 | 9/2008 | Antwiler |
| 2008/0248552 A1 | 10/2008 | Castillo Fernandez |
| 2010/0112700 A1 | 5/2010 | Shaaltiel et al. |
| 2010/0203638 A1 | 8/2010 | Adachi et al. |
| 2012/0058560 A1 | 3/2012 | Deriches et al. |
| 2012/0171764 A1 * | 7/2012 | Castillo Fernandez ................ C12M 27/22 435/325 |
| 2012/0295352 A1 | 11/2012 | Antwiler |
| 2013/0059339 A1 | 3/2013 | Kererangabo et al. |
| 2013/0196375 A1 | 8/2013 | Strobbe |
| 2014/0030762 A1 | 1/2014 | Deplano et al. |
| 2014/0162363 A1 | 6/2014 | Castillo Fernandez |
| 2014/0186937 A1 | 7/2014 | Smith et al. |
| 2014/0227769 A1 | 8/2014 | Strobbe |
| 2014/0331552 A1 | 11/2014 | Lau et al. |
| 2015/0017723 A1 | 1/2015 | Rooney et al. |
| 2016/0032238 A1 | 2/2016 | Lawin et al. |
| 2016/0108351 A1 | 4/2016 | Lee |
| 2017/0073625 A1 | 3/2017 | Kasuto et al. |
| 2017/0096627 A1 | 4/2017 | Smith et al. |
| 2017/0145365 A1 | 5/2017 | Nozaki et al. |
| 2017/0198246 A1 | 7/2017 | Niazi |
| 2019/0211294 A1 * | 7/2019 | Karnieli ............. C12M 41/48 |
| 2019/0270966 A1 | 9/2019 | Rooney et al. |
| 2022/0204905 A1 * | 6/2022 | Karnieli ............. C12M 29/18 |

FOREIGN PATENT DOCUMENTS

| | | |
|---|---|---|
| EP | 0380610 B1 | 3/1995 |
| JP | S5476893 A | 6/1797 |
| JP | S61202680 | 8/1986 |
| JP | H03240486 A | 10/1991 |
| JP | 2009509559 A1 | 3/2009 |
| JP | 2014014365 A | 1/2014 |
| JP | 2015501651 A | 1/2015 |
| JP | 2016086791 A | 5/2016 |
| WO | 1986005202 A1 | 9/1986 |
| WO | 93/18132 A2 | 9/1993 |
| WO | 1998033886 A1 | 8/1998 |
| WO | 2008056734 A1 | 5/2008 |
| WO | 2009010661 A2 | 1/2009 |
| WO | 2011/161086 A2 | 12/2011 |
| WO | 2013/048546 A1 | 4/2013 |
| WO | 2016050544 A1 | 4/2016 |

* cited by examiner

METHOD OF USING A BIOREACTOR

This application claims the benefit of priority of U.S. patent application Ser. No. 16/325,389, filed Feb. 14, 2019, issued as U.S. Pat. No. 11,549,090; which is the National Stage Entry of and claims the benefit of priority of PCT/IL/2017/050927, filed Aug. 21, 2017; which claims priority to each of U.S. provisional application 62/489,065, filed Apr. 24, 2017, and U.S. provisional application 62/377,628, filed Aug. 21, 2016, each of which is incorporated by reference herein in its entirety.

FIELD OF DISCLOSURE

Bioreactors comprising a perforated barrier for growing living cells or microorganisms are disclosed herein. Methods for growing cells or microorganisms in the bioreactors described herein, wherein regulation of flow-rates may be used for growth of cells or microorganisms at different densities.

BACKGROUND

Bioreactors are used to culture microorganisms and isolated living cells, including mammalian and human cells, in a contained and controlled environment. In many cases, the culturing of microorganisms and cells require the microorganisms or cells be physically separated and isolated from the surrounding environment and maintained in a sterile environment. Such cases can include the development and manufacturing of therapeutic microorganisms or cells, such as vaccines and genetically modified cells, and the manufacturing of tools for therapy such as viruses for gene therapy, proteins, antibodies or therapeutic cells. Additionally, the need for containment of the microorganism or cell from the environment could be in cases in which the organism is hazardous.

Culturing and processing of such microorganisms and cells requires several typical steps that might include, but are not limited to, inoculating a bioreactor with a small number of organisms or cells, constantly supplying the microorganism or cells with nutrients, media, supplements, activators, measuring microorganism or cell number, maintaining viability, maintaining identity of the microorganism or cell, maintaining the physical state, and cell collection. During growth and expansion of microorganisms and cells in a bioreactor, it is also important to monitor parameters such as media and glucose consumption, Oxyen, H+ ions in media, conductivity and more. Additionally, long term culturing will usually include transfer of the microorganisms or cells to larger containers as they proliferate. Once the number of microorganism or cells reaches the needed number or activity, the microorganisms or cells are usually processed and formulated. Such processing can include washing of the growth media, concentrating the cells or microorganisms, replacing the media to the final preservation media, or packaging and freezing the microorganisms or cells for further use.

Bioreactors may be used for growing, proliferating, differentiating and maintaining living cells and/or microorganisms for different purposes. Cells grown in such bioreactors are typically perfused by a growth medium, which provides nutrients and oxygen to the cells and removes waste materials and carbon dioxide excreted by the cells. Typically, various steps may be performed before and/or during the culturing of cells or microorganisms in such bioreactors including, for example, selecting cells, culturing cells, modifying cells, activating the cells, expanding the cells (by cell proliferation), washing the cells, concentrating the cells and final formulating of the cells (or microorganisms).

To date, propagation is commonly performed by transferring the medium with the microorganisms or cells between different containers and various tools are used for this purpose, such as larger growth vessels, centrifugation tubes or bags, intermediate storage containers and the final packaging. The above processes may typically include open manipulations were the microorganisms or cells are transferred from one step to the other.

Several of the above indicated steps may require removing the cells from the bioreactor and further subjecting them to steps such as, among others centrifugation, separation, incubation, counting, testing, separation, formulation and packaging. Unfortunately, any steps involving taking the cells or microorganisms out of the bioreactor significantly increase the risk of contamination of the cell by unwanted microorganisms (such as, for example, fungi, bacteria, mycoplasma or other undesired microorganisms) which may adversely compromise the cell culturing process.

There is a long felt need for closed system bioreactors that may reduce or eliminate the need to process the cells or microorganisms by taking them out of the bioreactor and reduce or eliminate the steps and human interaction with the cells during the culture. Furthermore, there is a need to automate and optimize the process end to end by processing the cells from early stages to a final product in one automated and closed system. The bioreactors described herein address these needs and further provide advantageous growth conditions allowing for higher yields and lower media needs.

SUMMARY

In one aspect, disclosed herein is a bioreactor for growing cells or microorganisms therein, the bioreactor comprising:
  a closed vessel enclosing a space therein;
  a first barrier having a plurality of pores therein, the first barrier is sealingly disposed within the space configured to divide the space into a first chamber and a second chamber, wherein the second chamber is configured to accommodate the growing cells or microorganisms therein, and wherein a diameter of the pores is configured to allow a fluid flow solely between the first chamber and the second chamber and vice versa,
  one or more fluid inlet ports for introducing the fluid into the first chamber; and
  one or more fluid outlet ports for allowing the fluid to exit from the second chamber.

In some related aspects, the first barrier does not allow cells or microorganisms grown in the vessel to pass between the first chamber and the second chamber.

In some related aspects, the first chamber is a lower chamber and the second chamber is an upper chamber and wherein the fluid flow comprises an upstream flow In some related aspects, the first barrier is disposed in contact with walls of the vessel.

In some related aspects, the bioreactor further comprises an aligning barrier having a plurality of pores therein; the aligning barrier is sealingly disposed within the space of the first chamber under the first barrier; the aligning barrier is configured to align the fluid flow and prevent bubbles passage.

In some related aspects, the aligning barrier is configured to control velocity of the fluid flow.

In some related aspects, the pores of the aligning barrier comprise conical shapes.

In some related aspects, the bioreactor further comprises an additional screening barrier having a plurality of pores therein; the screening barrier is disposed within the space of the second chamber, at top section of the second chamber, such that the growing cells or microorganisms are accommodated between the first barrier and the screening barrier; the screening barrier is configured to prevent the cells passage.

In some related aspects, the bioreactor vessel is constructed of at least two parts.

In some related aspects, the vessel of the bioreactor is configured to provide a fluid velocity gradient in the fluid disposed within the second chamber, such that the velocity of the fluid decreases in a direction from the first barrier towards a top surface of the fluid.

In some related aspects, at least the second chamber comprises an increasing transversal cross sectional area from bottom top of the second chamber.

In some related aspects, the shape of the transversal cross sections is selected from: a circle, an ellipse, a polygon, and any combination thereof.

In some related aspects, the shape of the vessel is selected from: a conical shape, a frustoconical shape, a tapering shape, a cylindrical shape, a polygonal prism shape, a tapering shape having an ellipsoidal transversal cross section, a tapering shape having a polygonal transversal cross section, a shape having a cylindrical part and a tapering part and a shape having a conical or tapered part and a hemispherical part, and any combination thereof.

In some related aspects, at least one of the one or more fluid outlet ports is configured to be fluidically connected to a pump, which is configured to receive the fluid from the second chamber, and optionally wherein the pump is further configured to recirculate the fluid back into the first chamber via a t least one of the fluid inlet ports.

In some related aspects, the rate of flow of the fluid through the second chamber is controlled by the pump's pumping rate.

In some related aspects, the fluid comprises any one of: a growth media, a washing solution, a nutrient solution, a collection solution, a harvesting solution, a storage solution, and any combination thereof.

In some related aspects, wherein the one or more fluid outlet ports comprise a plurality of fluid outlet ports opening at different positions along the height of the second chamber.

In some related aspects, the first barrier is a fixed non-movable barrier.

In some related aspects, the fixed barrier is selected from: a flat barrier, a flat barrier inclined at an angle to a longitudinal axis of the bioreactor, a concave barrier with a concave upper surface facing top of the vessel, a tapering barrier and a conical barrier.

In some related aspects, the bioreactor further comprises at least one harvesting port disposed in the vicinity of an upper surface of the first barrier configured to harvest cells from the bioreactor.

In some related aspects, the bioreactor is configured to be inverted.

In some related aspects, the bioreactor further comprises a supporting matrix disposed within the second chamber for supporting the cells or microorganisms.

In some related aspects, the bioreactor further comprises a controller is operably coupled and configured to control at least to one of:

at least one sensor unit comprising one or more sensors configured to sense one or more chemical and/or physical properties of the fluid within the vessel;

a plurality of controllably openable and closable valves configured to control the flow the fluid within the one or more fluid outlet ports outlet and fluid inlet ports;

a controllably openable and closable valve configured to control the flow of fresh liquid fluid from a fluid reservoir into an inlet port of the the pump;

a heater unit configured to heat the fluid within the vessel;

a cooling unit configured to cool the fluid within the vessel; and a gas valve configured to control the flow of a gas comprising oxygen from an oxygen source into a gas dispersing head disposed within the vessel.

In a related aspect, a method for growing cells or microorganisms is disclosed, in a bioreactor of according to any one of the above aspects, the method comprises the steps of:
introducing cells or microorganisms into the second chamber of the bioreactor;
perfusing the cells or microorganisms with the fluid;
growing the cells to a desired concentration; and
harvesting the cells or microorganisms from the bioreactor.

In some related aspects, the step of perfusing comprises controlling the level and/or the rate of flow of the fluid within the bioreactor.

In some related aspects, the step of perfusing comprises re-circulating the fluid through the first barrier.

In some related aspects, the step of re-circulating further comprises at least one of:
a step of adding an amount of fresh fluid to the bioreactor; and
a step of draining an amount of the fluid from the bioreactor.

In some related aspects,
the step of perfusing further comprises a step of oxygenating the fluid; or
the step of perfusing further comprises controlling the level and/or the rate of flow of the fluid within bioreactor; or
the method further comprises step of increasing the level of the fluid in the second chamber; or
the method further comprises one or more steps of washing the cells or microorganisms; or
the method further comprises a step of concentrating the cells by reducing the volume of the fluid within the second chamber; or
the method further comprises a step of maintaining the cell mass in a floating position at a specific region in the second chamber, due to a balance between gravity force applied on the cell mass and selected velocity of the upstream fluid flow; or
any combination thereof.

In some related aspects, the cells are adherent cells and the method further comprises a step of allowing the cells to attach to one or more surfaces disposed within the second chamber.

In some related aspects, the one or more surfaces are selected from the group consisting of, the upper surface of the first barrier, the surface of the walls of the second chamber, the surface of a cell supporting matrix disposed within the second chamber and any combination thereof.

In some related aspects, the method further comprises a step of co-culturing the cells with additional different cells.

In some related aspects,
the cells are T-cells and the additional different cells are cytokine secreting cells; or
the cells are T-cells and the additional different cells are antigen presenting cells; or
the cells are embryonic stem cells and the additional different cells are feeder cells.

In some related aspects, the steps of introducing, perfusing, growing, washing and harvesting the cells are continuous and performed in or from the second chamber.

In one aspect, disclosed herein is a bioreactor for growing cells or microorganisms therein, the bioreactor comprising: a vessel having a vessel wall enclosing a space thein; a perforated barrier having a plurality of perforations therein, the barrier is sealingly disposed within the space to divide the space into a first chamber and a second chamber, wherein the diameter of the perforations is configured to allow solely a liquid flow from the first chamber to the second chamber and from the second chamber to the first chamber, one or more fluid inlet ports for introducing the liquid into the first chamber, and one or more fluid outlet ports for allowing the liquid to exit the second chamber.

In a related aspect, the bioreactor further comprises a fluid impeller disposed within the first chamber and fluidically coupled to the one or more fluid inlet port. According to some embodiments, the fluid impeller comprises a hollow member having a plurality of perforations and/or fluid nozzles therein configured for ejecting multiple jets of a liquid within the first chamber when the liquid is pumped into the one or more fluid inlet port. In another related aspect, the bioreactor further comprises a gas dispersing head configured for providing oxygen to the liquid.

In another related aspect, one or more fluid outlet ports comprises a single fluid outlet port, and the one or more inlet ports comprises a single fluid inlet port, and wherein the fluid inlet port is configured for introducing the liquid into the first chamber by a pump fluidically connected to the fluid inlet port, wherein the pump is configured to fluidically connect to the single fluid outlet port and configured to receive the liquid from the second chamber, and configured for recirculating the liquid within the bioreactor.

In a related aspect, the rate of flow of the liquid through the second chamber is controlled by controlling the rate of pumping of the liquid by the pump. In another related aspect, the liquid comprises a growth media, a washing solution, a nutrient solution, a collection solution, a harvesting solution, a storage solution, or any combination thereof.

In a related aspect, one or more fluid inlet port comprises one fluid inlet port and the one or more fluid outlet ports comprise a plurality of fluid outlet ports opening at different positions along the height of the second chamber, and wherein the plurality of fluid outlet ports are configured to each be fluidically connectable to a fluid manifold, wherein the fluid manifold is fluidically connected to a pump such that any selected fluid output port of the plurality of fluid outlet ports is configured to be fluidically controllably connected to the pump by the fluid manifold for receiving the liquid from the second chamber into the pump through the selected fluid output port and for introducing the liquid by the pump into the first chamber through the single fluid inlet port, wherein the level of the liquid within the second chamber is determined by the fluid outlet port selected from the plurality of fluid outlet ports.

In another related aspect, the bioreactor further comprises a plurality of valves, each fluid outlet port of the plurality of fluid outlet ports is configured to be fluidically coupled to a valve of the plurality of valves, and wherein the fluid manifold is configured to be fluidically selectably connectable to any selected fluid outlet port of the plurality of fluid outlet ports through the valve connected to the fluid output port. In another related aspect, the bioreactor further comprises a temperature control unit configured for regulating the temperature of the liquid disposed within the bioreactor. In another related aspect, the temperature control unit is selected from: a heating element, a cooling element, and a combination of a heating element and a cooling element.

In a related aspect, the bioreactor is configured for establishing a fluid velocity gradient in the liquid disposed within the second chamber such that the velocity of the liquid in the second chamber gradually decreases in the direction from the perforated barrier towards the top surface of the liquid in the second chamber. In another related aspect, the fluid velocity gradient in the liquid is achieved by the transversal cross sectional area of the top part of the second chamber being larger than the transversal cross sectional area of the bottom part of the second chamber.

In another related aspect, the shape of transversal cross sections of the second chamber is selected from a circle, an ellipse, a polygon, and a regular polygon. In another related aspect, the vessel walls of the bioreactor comprise one or more closable and/or sealable openings formed therein. In another related aspect, one or more closable and/or sealable openings are selected from one or more openings disposed in the top part of the bioreactor, and one or more openings disposed in the side walls of the bioreactor, and any combinations thereof.

In a related aspect, the bioreactor further comprises a self-sealing gasket sealingly disposed in the vessel walls and configured for inserting of a syringe needle through the gasket for injecting the cells or microorganisms into the second chamber through the needle.

In a related aspect, the shape of the bioreactor is selected from a conical shape, a frustoconical shape, a tapering shape, a cylindrical shape, a polygonal prism shape, a tapering shape having an ellipsoidal transversal cross section, a tapering shape having a polygonal transversal cross section, a shape having a cylindrical part and a tapering part and a shape having a conical or tapered part and a hemispherical part, or a combination thereof.

In a related aspect, the perforated barrier is a fixed non-movable perforated barrier. In another related aspect, the fixed perforated barrier is selected from, a flat perforated barrier, a flat perforated barrier inclined at an angle to a longitudinal axis of the bioreactor, a concave perforated barrier with a concave upper surface facing the top of the bioreactor, a tapering perforated barrier and a conical perforated barrier. In another related aspect, the perforated barrier is a movable perforated barrier. In another related aspect, the movable perforated barrier is selected from, a movable perforated barrier sealingly attached to the vessel walls by a flexible and/or stretchable member the flexible and/or stretchable member is sealingly attached to a perimeter of the perforated barrier and sealingly attached to the vessel wall, a deformable and/or flexible perforated barrier, and a convex buckling perforated barrier with a convex upper surface facing the top of the bioreactor. In another related aspect, the perforated barrier further comprises a magnetic member attached thereto for enabling moving and/or tilting and/or deforming and/or buckling of the perforated barrier by applying force to the perforated barrier using a magnet disposed outside of the bioreactor. In another related aspect, the perforated barrier does not allow cells or microorganisms grown in the vessel to pass through the perforated barrier from the first chamber to the second chamber and the second chamber to the first chamber.

In a related aspect, the bioreactor further comprises an additional perforated barrier within the first chamber between the bottom of the vessel and the perforated barrier that separates the first and second chambers, or an additional perforated barrier within the second chamber between the cells and the top of the vessel, or a combination thereof.

In a related aspect, the bioreactor further comprises at least one harvesting port disposed in the vessel walls and opening into the second chamber in the vicinity of an upper surface of the perforated barrier configured for harvesting cells from the bioreactor. In a related aspect, the bioreactor further comprises a harvesting port including a hollow member having a first end sealingly attached to the perforated barrier and opening at an upper surface of the perforated barrier, and a second end sealingly passing through the walls of the first chamber and closeably opening outside the bioreactor. In another related aspect, the bioreactor includes at least one harvesting port disposed in the vessel walls and opening into the second chamber in the vicinity of an upper surface of the perforated barrier, and wherein the bioreactor is a tiltable bioreactor configured to be tilted at an angle to a vertical direction to assist the harvesting of cells through the at least one harvesting port.

In a related aspect, the bioreactor is configured to be inverted.

In a related aspect, the bioreactor further comprises an openable/closable outlet port disposed in the walls or bottom part of the first chamber configured for draining at least some of the liquid from the bioreactor. In another related aspect, the bioreactor is configured to be fluidically connected to a pump fluidically couplable to a fluid reservoir disposed outside of the bioreactor for introducing fresh liquid from the fluid reservoir into the bioreactor.

In a related aspect, the bioreactor further comprises at least one sensor unit comprising at least one sensor configured for sensing one or more chemical and/or physical properties of the liquid.

In a related aspect, the bioreactor is operationally couplable to a controller for controlling the operation of the bioreactor.

In a related aspect, the bioreactor further comprises a fluid impeller disposed within the first chamber and fluidically coupled to at least one fluid inlet port of the one or more fluid inlet ports, the fluid impeller comprises a hollow member having a plurality of perforations and/or fluid nozzles therein configured for ejecting multiple jets of a liquid within the first chamber when the liquid is pumped into the at least one fluid inlet port. In another related aspect, the one or more fluid inlet ports and the one or more fluid outlet ports comprise or are configured to be fluidically connected to valves for controllably opening and closing the one or more fluid inlet ports and the one or more fluid outlet ports. In another related aspect, the valves are selected from manually operable valves and automatically operable valves connectable to a controller. In another related aspect, the automatically operable valves are electrically actuated solenoid based valves connectable to a controller for automatically controlling the opening and closing of the valves.

In a related aspect, the bioreactor further comprises a supporting matrix disposed within the second chamber for supporting the cells or microorganisms.

In one aspect, this application discloses a bioreactor system comprising: a bioreactor as disclosed herein; and a pump for circulating a liquid within the bioreactor.

In a related aspect, the pump receives liquid from the one or more fluid outlet ports and pumps the received liquid into the one or more fluid inlet ports. In another related aspect, the bioreactor system further comprises a fluid reservoir fluidically couplable to an inlet port of the pump for controllably providing fresh liquid to the pump to be pumped into the first chamber.

In a related aspect, the bioreactor system further comprises a controller for manually or automatically controlling the operation of the bioreactor. In another related aspect, the controller is operably coupled to one or more of, at least one sensor unit comprising one or more sensors for sensing one or more chemical and/or physical properties of the liquid, a plurality of controllably openable and closable valves for controlling the flow of the liquid within the one or more fluid outlet ports outlet, a controllably openable and closable valve for controlling the flow of fresh liquid from a fluid reservoir into an inlet port of the pump, a heater unit for heating the liquid, a cooling unit for cooling the liquid, and a gas valve for controlling the flow of a gas comprising oxygen from an oxygen source into a gas dispersing head disposed within the bioreactor.

In a related aspect, the bioreactor further comprises a supporting matrix disposed within the second chamber for supporting the cells or microorganisms.

BRIEF DESCRIPTION OF THE DRAWINGS

The subject matter disclosed herein is particularly pointed out and distinctly claimed in the concluding portion of the specification. However, the bioreactors disclosed herein, both as to organization and method of operation, together with objects, features, and advantages thereof, may best be understood by reference to the following detailed description when read with the accompanying drawings in which:

FIG. 4A presents a bioreactor (300) that has a shape that has a cylindrical part (304A) and a frustoconical part (304B); FIG. 4B presents a bioreactor (310) that has a shape that has a cylindrical part (314A) and a tapering part (314B); FIG. 4C presents another embodiment of a bioreactor (320) that has a shape that has a cylindrical part (324A) and a tapering part (324B); FIG. 4D presents a bioreactor (330) that has a tapering shape; FIG. 4E presents another embodiment of a bioreactor (340) that has a tapering shape; FIG. 4F presents a bioreactor (350) that has a shape that has a conical part (354A) and a frustoconical part (354B); FIG. 4G presents a bioreactor (360) that has a cylindrical shape; FIG. 4H presents a bioreactor (370) that has a shape similar to a chalice, comprising a first chamber (374A) shaped as a hemispherical and a second chamber (374B) shaped as a frustoconical part; FIG. 4I presents a bioreactor (380) that comprises a vertical wall portion (380H) and a slanted wall portion (380E);

In FIG. 6A, the bioreactor (510) is in a vertical state; In FIG. 6B, the bioreactor (510) is in a tilted state:

FIG. 14B shows growth curves after 5 days in the T75 flask (Blue line) and the Bioreactor (orange); FIG. 14C shows growth curves after 14 days of growth in the bioreactor (yellow line) in comparison with cells grown in T175 flasks, with (blue line) and without (grey line) change of media;

FIG. 15A presents an embodiment of replacing one liquid with another, for example replacing growth media with wash buffer; FIG. 15B presents another embodiment of replacing one liquid with another, wherein the bioreactor comprises a second barrier (barrier 2) located in a position within a second (upper chamber) above the level of the cells; the bioreactor vessel shown in FIG. 15B is inverted in the image; FIGS. 15C and 15D show representative diagrams of a bioreactor constructed of two frusto-conical parts, divided into three chambers by two perforated barriers, where FIG. 15C demonstrates the bioreactor during cell growth stage and FIG. 15D demonstrates the bioreactor as its flipped position during a washing stage.

Figure 1:
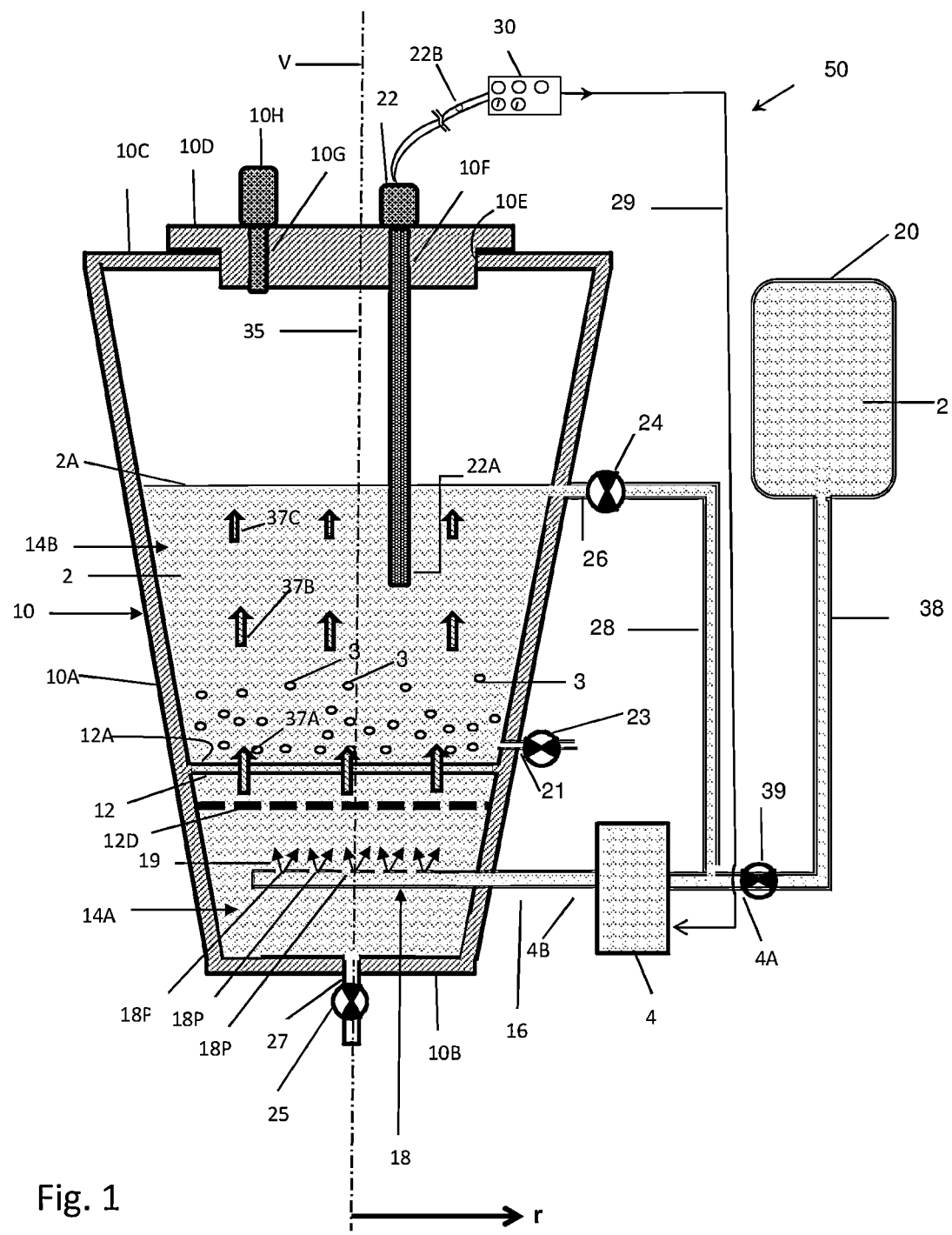
FIG. 1 is a schematic part cross-sectional view illustrating some embodiments of a bioreactor system disclosed herein, wherein the system comprises a bioreactor comprising a perforated barrier.

It will be appreciated that for simplicity and clarity of illustration, elements shown in the figures have not necessarily been drawn to scale. For example, the dimensions of some of the elements can be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the bioreactors described herein, and use thereof. In other instances, well-known methods, procedures, and components have not been described in detail so as not to obscure the bioreactors described herein and uses thereof.

The present application discloses a cell culturing processing and manipulating system including bioreactors and bioreactor systems designed for culturing of cells and microorganisms in changing densities and adaptive culture volumes starting from isolation to final formulation. The bioreactors disclosed herein are configured to continuously allow all the necessary steps of selecting, culturing, modifying, activating, expanding, washing, concentrating and formulating in one single unit. According to some embodiments, the bioreactors can be used in a batch mode, fed batch mode and perfusion mode and can be fully controlled in a closed, aseptic environment and can be implemented for a single use (to be disposed after one culturing cycle) as well as for multiple cycle uses.

Before explaining the various embodiments of the bioreactors and systems thereof as disclosed herein in detail, it is noted that the bioreactors and systems thereof disclosed, are not necessarily limited in its application to the details of construction and the arrangement of the components and/or methods set forth in the following description and/or illustrated in the drawings and/or the Examples. The bioreactors and systems thereof disclosed herein can encompass other embodiments or of being practiced or carried out in various ways.

The present application in some embodiments thereof, discloses a flow or a stream of a "medium", "liquid", "gas", "wash buffer", "solution" or "fluid". A skilled artisan would appreciate that these terms are alternatively used and having a characteristic of a substance that continually deforms (flows) under an applied pressure and/or an applied shear stress.

The present application in some embodiments thereof, discloses bioreactors for growing living cells or microorganisms, and methods thereof for growing cells or microorganisms in these bioreactors including all culturing steps from isolation to final formulation.

A skilled artisan would appreciate that the terms "cell" and "cells" may encompass any living cells. In some embodiments, cells that may be grown in a bioreactor disclosed herein comprise any prokaryotic or eukaryotic cell. In some embodiments, cells that may be grown in a bioreactor disclosed herein comprise unicellular and multicellular microorganisms, for example bacteria, archaebacteria, viruses, yeast cells, plant cells, or insect cells.

In some embodiments, eukaryotic cells comprise plant cells, insect cells, animal cells, or fungi. In some embodiments, cells comprise tissue culture cells, primary cells, or reproductive cells. In some embodiments, tissue culture cells or primary cells comprise stem cells, adult cells, transdifferentiated cells, dedifferentiated cells, or differentiated cells. In some embodiments, animal cells comprise mammalian cells. For example, mammalian cells may comprise cells originating from a baboon, buffalo, cat, chicken, cow, dog, goat, guinea pig, hamster, horse, human, monkey, mouse, pig, quail, or rabbit. In some embodiments, mammalian cells comprise primary cells comprising stem cells, embryonic cells, adult cells, transdifferentiated cells, dedifferentiated cells, or differentiated cells. In some embodiments, mammalian cells comprise tissue culture cells comprising stem cells, embryonic cells, adult cells, transdifferentiated cells, dedifferentiated cells, or differentiated cells.

In some embodiments, the cell types compatible with growth in a bioreactor disclosed herein include stem cells, Acinar cells, Adipocytes, Alveolar cells, Ameloblasts, Annulus Fibrosus Cells, Arachnoidal cells, Astrocytes, Blastoderms, Calvarial Cells, Cancerous cells (Adenocarcinomas, Fibrosarcomas, Glioblastomas, Hepatomas, Melanomas, Myeloid Leukemias, Neuroblastomas, Osteosarcomas, Sarcomas) Cardiomyocytes, Chondrocytes, Chordoma Cells, Chromaffin Cells, Cumulus Cells, Endothelial cells, Endothelial-like cells, Ensheathing cells, Epithelial cells, Fibroblasts, Fibroblast-like cells, Germ cells, Hepatocytes, Hybridomas, Insulin producing cells, Intersticial Cells, Islets, Keatinocytes, Lymphocytic cells, Macrophages, Mast cells, Melanocytes, Meniscus Cells, Mesangial cells, Mesenchymal Precursor Cells, Monocytes, Mononuclear Cells, Myeloblasts, Myoblasts, Myofibroblasts, Neuronal cells, Nucleus cells, Odontoblasts, Oocytes, Osteoblasts, Osteoblast-like cells, Osteoclasts, Osteoclast precursor cells. Oval Cells, Papilla cells. Parenchymal cells, Pericytes, Peridontal Ligament Cells, Periosteal cells, Platelets, Pneumocytes, Preadipocytes, Proepicardium cells, Renal cells, Salisphere cells, Schwann cells, Secretory cells, Smooth Muscle cells, Sperm cells, Stellate Cells. Stem Cells, Stem Cell-like cells, Stertoli Cells, Stromal cells, Synovial cells, Synoviocytes, T Cells, Tenocytes, T-lymphoblasts, Trophoblasts, Natural killer cells, dendritic cells, Urothelial cells, Vitreous cells, and the like; the cells originating from, for example and without limitation, any of the following tissues: Adipose Tissue, Adrenal gland, Amniotic fluid, Amniotic sac, Aorta, Artery (Carotid, Coronary, Pulmonary), Bile Duct, Bladder, Blood, Bone, Bone Marrow, Brain (including Cerebral Cortex), Breast, Bronchi, Cartilage, Cervix, Chorionic Villi, Colon, Conjunctiva, Connective Tissue, Cornea, Dental Pulp, Duodenum, Dura Mater, Ear, Endometriotic cyst, Endometrium, Esophagus, Eye, Foreskin, Gallbladder, Ganglia, Gingiva, Head/Neck, Heart, Heart Valve, Hippocampus, Iliac, Intervertebral Disc, Joint, Jugular vein, Kidney, Knee, Lacrimal Gland, Ligament, Liver, Lung, Lymph node, Mammary gland, Mandible, Meninges, Mesoderm, Microvasculature, Mucosa, Muscle-derived (MD), Myeloid Lukemia, Myeloma, Nasal, Nasopharyngeal, Nerve, Nucleus Pulposus, Oral Mucosa, Ovary, Pancreas, Parotid Gland, Penis, Placenta, Prostate, Renal, Respiratory Tract, Retina, Salivary Gland, Saphenous Vein, Sciatic Nerve, Skeletal Muscle, Skin, Small Intestine, Sphincter, Spine, Spleen, Stomach, Synovium, Teeth, Tendon, Testes, Thyroid, Tonsil, Trachea, Umbilical Artery, Umbilical Cord, Umbilical Cord Blood, Umbilical Cord Vein, Umbilical Cord (Wartons Jelly), Urinary tract, Uterus, Vasculature, Ventricle, Vocal folds and cells, or any combination thereof. In some embodiments, the cells grown in a bioreactor disclosed herein may comprise a combination of different cell types. As used herein, in some embodiments the terms "cells" and "microorganisms" may be used interchangeably having all the same meanings and qualities.

In some embodiments, the products of the cells or microorganisms grown in a bioreactor disclosed herein are collected, for example proteins, peptides, antibiotics or amino acids. In some embodiments, any product of a cell or microorganism grown in a large-scale manner in a bioreactor disclosed herein and synthesized by the cell or microorganism, can be collected.

Figure 2:
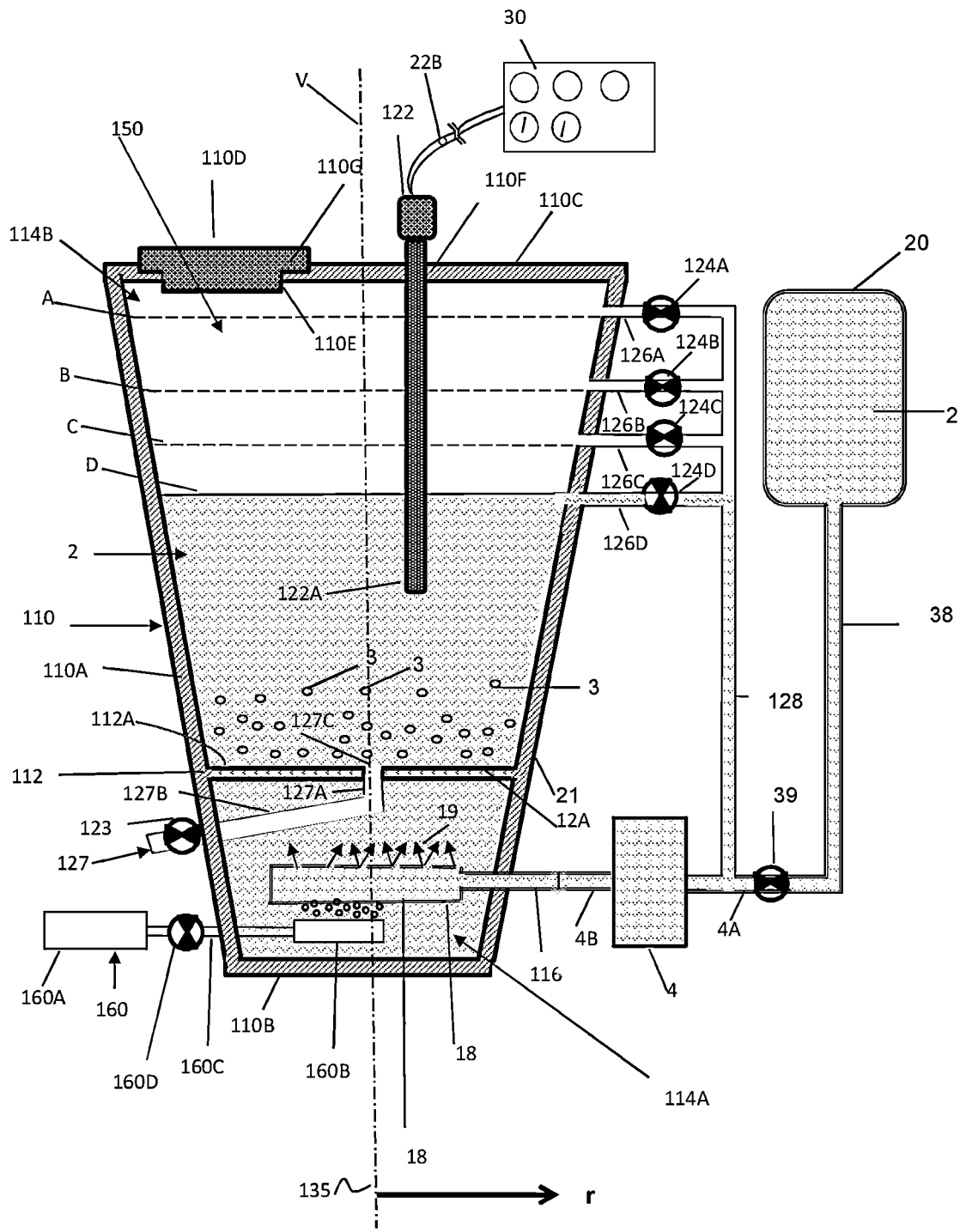
FIG. 2 is a schematic part cross-sectional view illustrating some embodiments of a bioreactor system disclosed herein comprising a bioreactor with multiple fluid outlet ports for controllably adjusting the level of the growth medium in the bioreactor.
Figure 3:
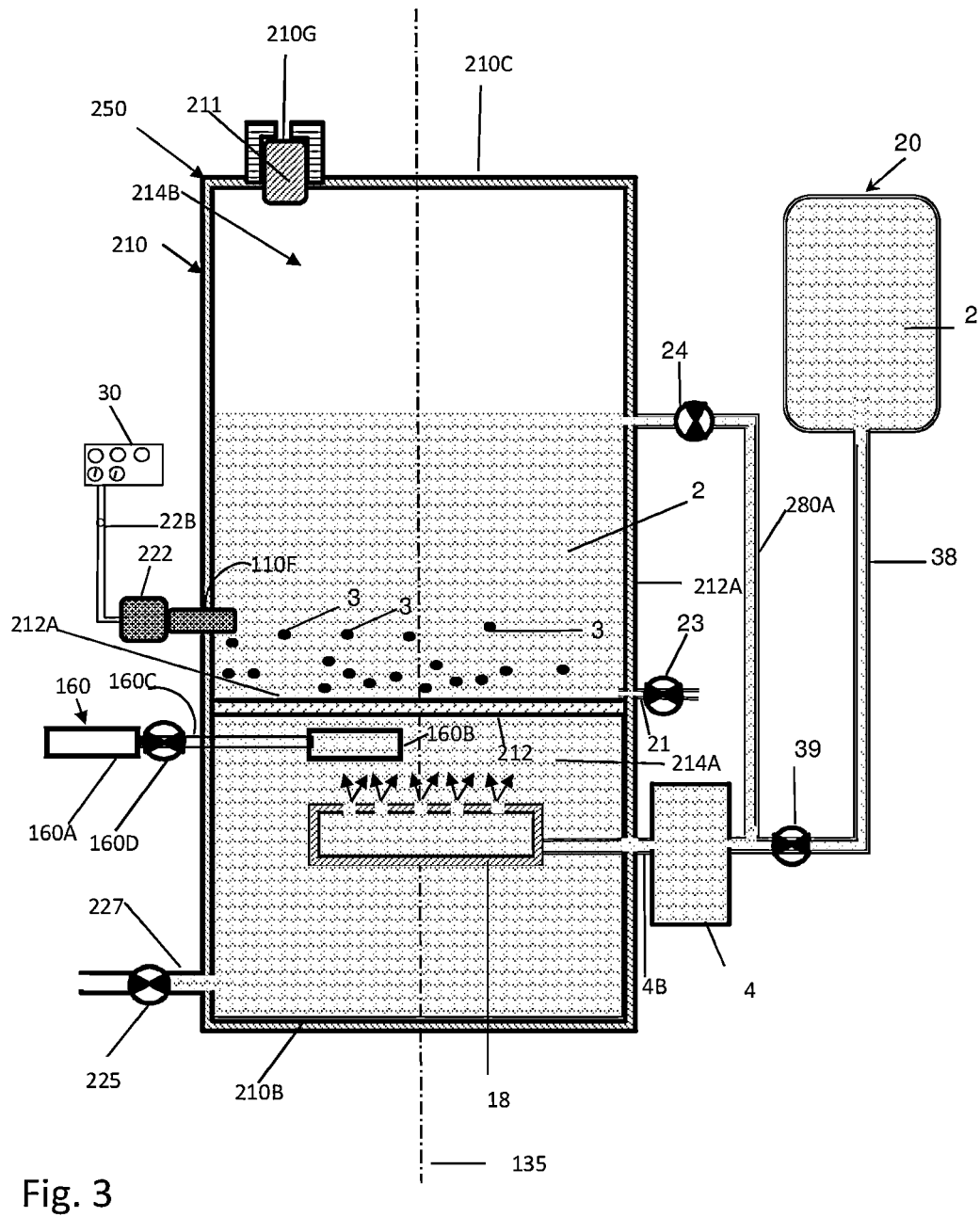
FIG. 3 is a schematic part cross-sectional view illustrating some embodiments of a bioreactor system disclosed herein comprising a bioreactor having a cylindrical shape including a perforated barrier.
Figure 4A:
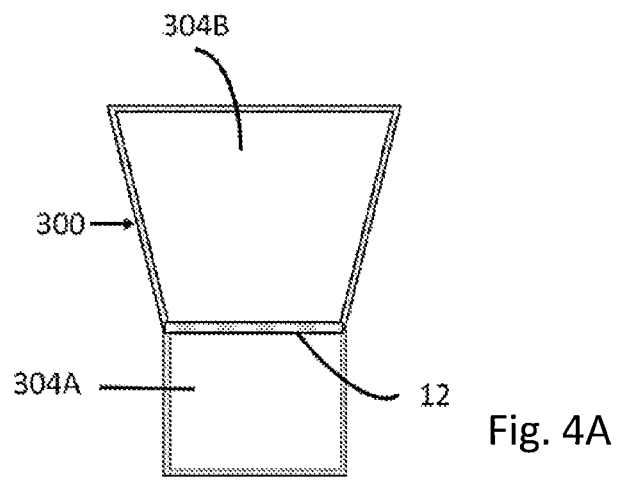
FIGS. 4A-4I are schematic cross-sectional views illustrating some embodiments of shapes of bioreactors comprising a perforated barrier (12)
Figure 4B:
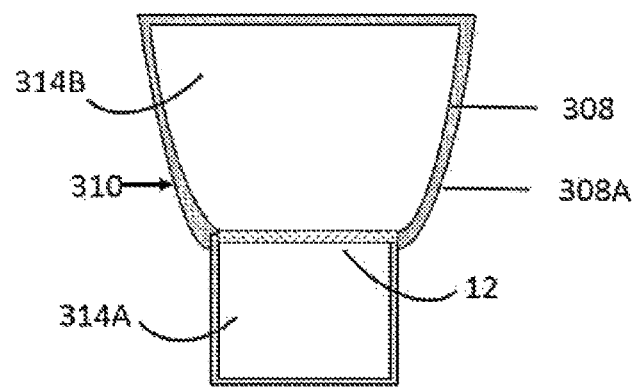
Figure 4C:
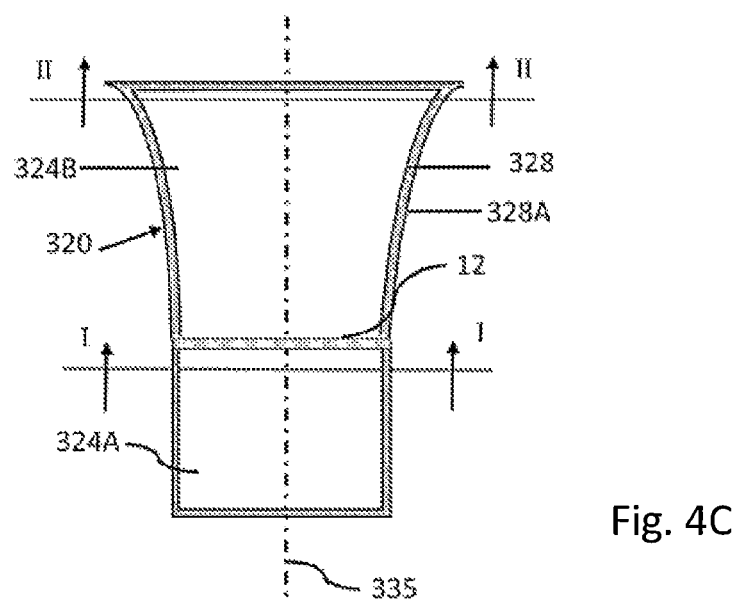
Figure 4D:
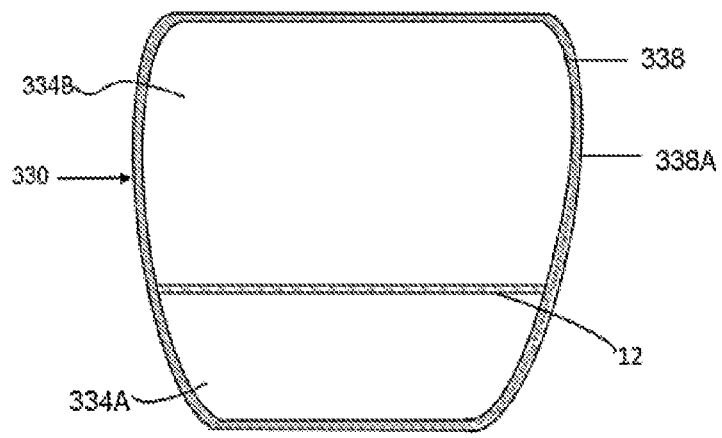
Figure 4E:
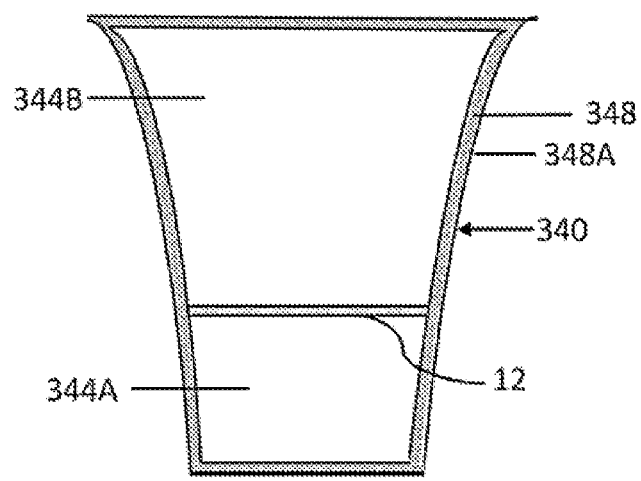
Figure 4F:
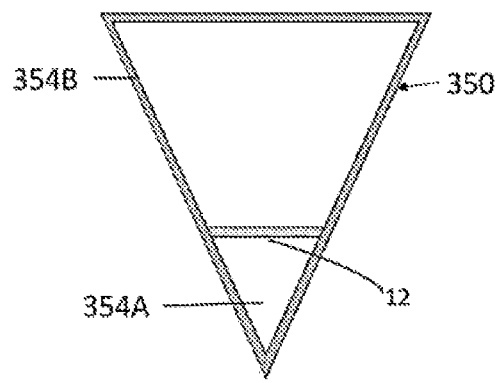
Figure 4G:
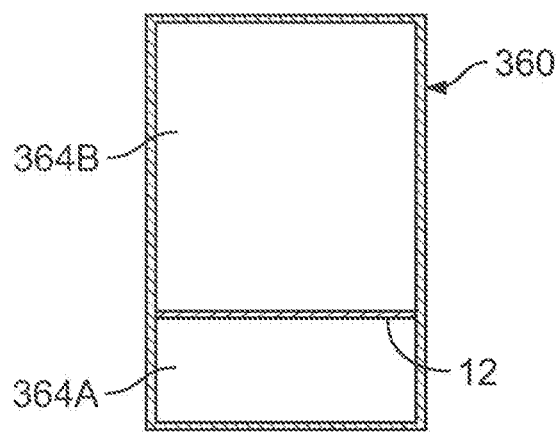
Figure 4H:
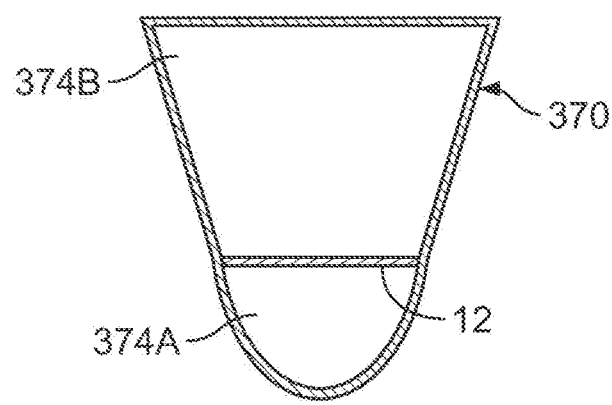
Figure 4I:
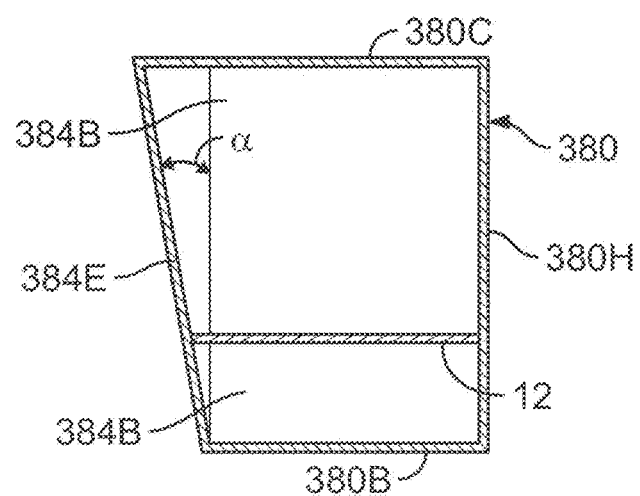
Figure 4J:
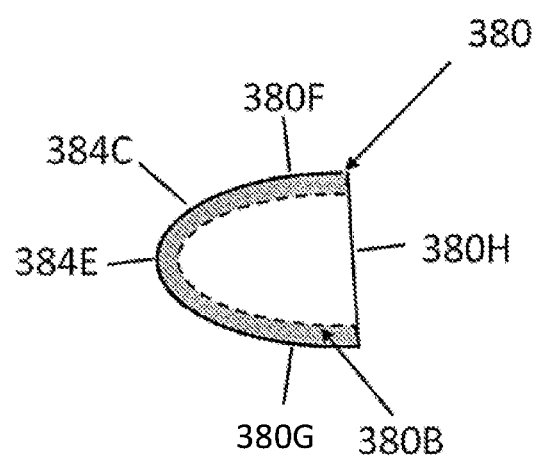
FIG. 4J is a schematic top view of the bioreactor (380) illustrated in FIG. 4I.
Figure 6A:
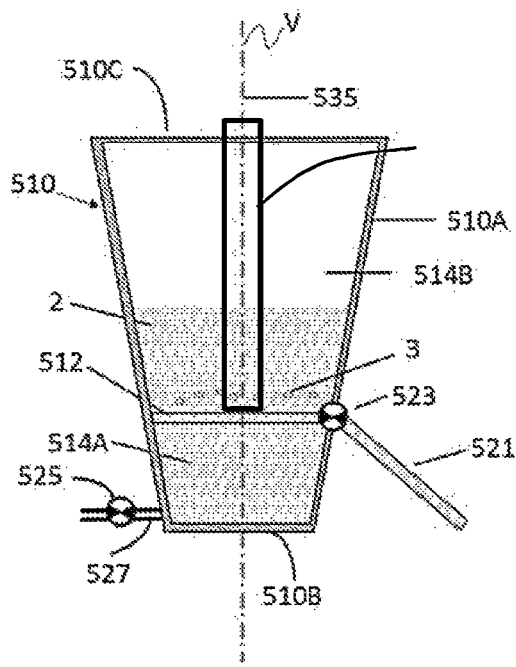
FIGS. 6A and 6B are schematic part cross-sectional views illustrating two embodiments of possible positional states of a tiltable bioreactor (510)
Figure 6B:
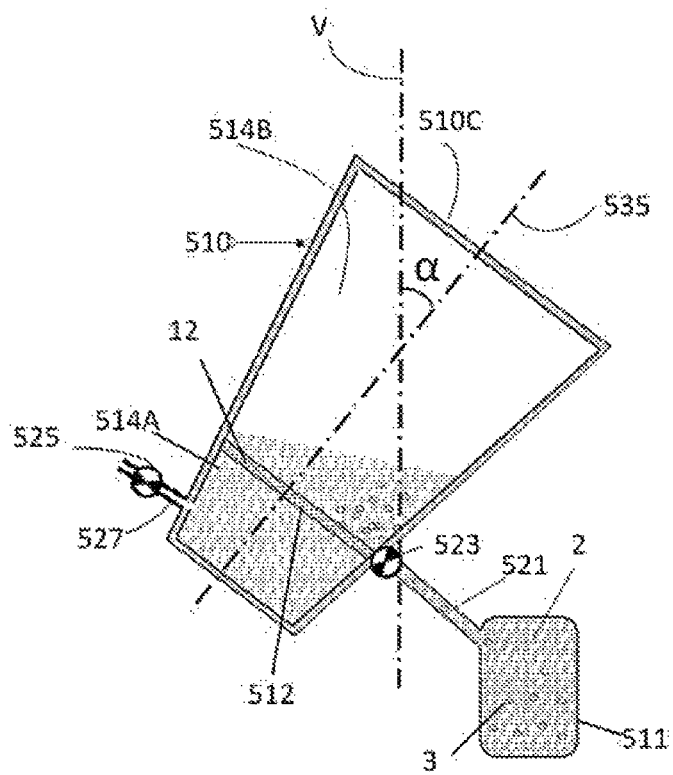
Figure 6C:
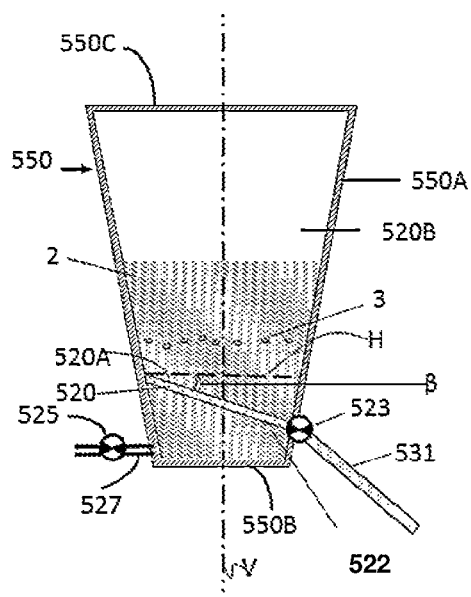
FIGS. 6C and 6D are schematic part cross-sectional views illustrating two embodiments of a bioreactor (550) having a fixed slanted perforated barrier.
Figure 6D:
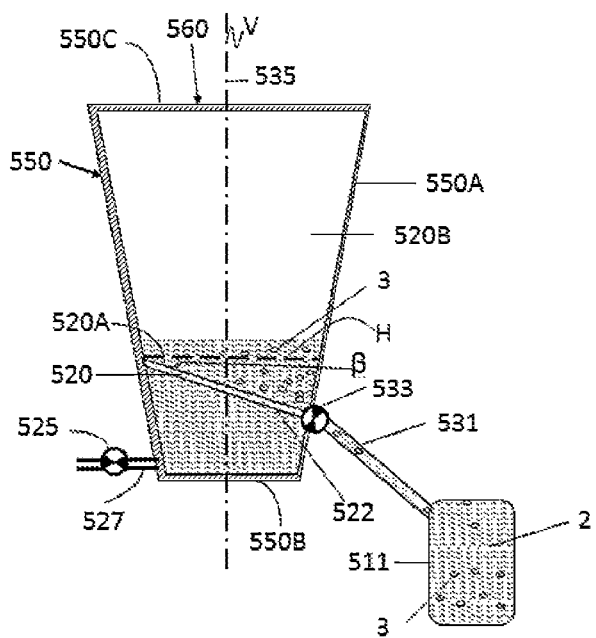
Figure 7:
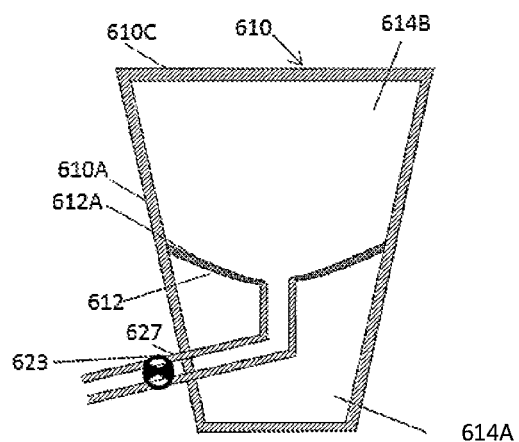
FIGS. 7-9 are schematic part cross-sectional views illustrating three different embodiments of bioreactors (610, 710, and 810, respectively) including three different types of non-planar (not flat) perforated barriers (612, 712, and 812, respectively)

The bioreactors disclosed in the present application, non-limiting of which are presented in FIG. 1 (10), FIG. 2 (110), FIG. 3 (210), FIG. 4A (300), FIG. 4B (310), FIG. 4C (320), FIG. 4D (330), FIG. 4E (340), FIG. 4F (350), FIG. 4G (360), FIG. 4H (370), FIG. 4I (380), FIGS. 6A and 6B (510), FIGS. 6C and 6D (550). FIG. 7 (610), FIG. 8 (710), FIG. 9 (810), FIGS. 10A and 10B (910), FIGS. 11A and 11B (1010), FIGS. 12A and 12B (1110), and FIG. 14A, can be shaped like a hollow vessel including a perforated barrier that divides the internal volume or space within the vessel into a first (lower) chamber and a second (upper) chamber disposed above the first chamber.

According to some embodiments, a bioreactor described herein for growing cells or microorganisms therein, the bioreactor comprising:
 a closed vessel enclosing a space therein;
 a barrier having a plurality of perforations therein, the barrier is sealingly disposed within the space configured to divide the space into a first chamber and a second chamber, wherein the second chamber is configured to accommodate the growing cells or microorganisms therein, and wherein a diameter of the perforations is configured to allow a fluid flow solely between the first chamber and the second chamber and vice versa,
 one or more fluid inlet ports for introducing the fluid into the first chamber; and
 one or more fluid outlet ports for allowing the fluid to exit from the second chamber.

According to some embodiments, the bioreactor vessel can be constructed of at least two parts. And according to some embodiments, the barrier can be attached between the two parts. According to some embodiments, more perforated barriers can be provided, in some cases between the different parts of the vessel. According to some embodiments, the barrier is disposed in contact with walls of the vessel (as demonstrated in FIGS. 1-4, 6-13, 15-16).

According to some embodiments, the first chamber is a lower chamber and the second chamber is an upper chamber and wherein the fluid flow is an upstream flow from the lower chamber towards the upper chamber (against gravity direction).

Without being limiting, in some embodiments, a bioreactor comprises a chamber comprising a widening shape, for example a conical frustum shape, or a portion thereof, which is configured to lead to reduction of velocity of a fluid. In some embodiments, a bioreactor comprises a chamber of two parts divided by a perforated barrier, wherein the barrier allows a constant fluid flow, for example but not limited to a fluid growth media, and wherein the cells are retained in the second (upper) chamber. In some embodiments, a bioreactor comprises reduced velocity of flow of a fluid in the second (upper) chamber and a uniform and gentle flow of a fluid throughout the vessel. In some embodiments, the gentle and uniform flow combined with the reduced velocity in the second (upper) chamber results in a balance between the mass of cells (cell mass) and the velocity of the fluid resulting in a steady mass of cells known as a "floating cake". In some embodiments, a floating cake of cells localized to the lower portion of the second (upper) chamber.

In some embodiments, use of a bioreactor described herein results in a constant fluid flow. In some embodiments, use of a bioreactor results in a constant flow of growth media and cell feeding during the culturing process. In some embodiments, a fluid, for example a growth media, can be exchanged during culturing, wherein very small volumes and/or very large volumes provide the for adaptive and optimal cell feeding. In some embodiments, use of a bioreactor described herein comprises cell washing and harvesting to a selected media in a very gentle and efficient manner without the need to open the bioreactor chamber. In some embodiments, use of a bioreactor described herein provides for optimal and adaptive culturing, wherein manipulation of cells or microorganisms is performed in a closed system, wherein the manipulation can be automated, and wherein cells experience minimal sheer force. In some embodiments, use of a bioreactor described herein supports high density growth of cells or microorganisms. In some embodiments, the density achieved, by the bioreactors disclosed herein, can be greater than 10-fold that observed using standard culturing conditions.

A skilled artisan would appreciate that the term "perforated barrier" may be used interchangeable with the term "filter" or "membrane" or "perforated plate" having all the same qualities and meanings.

In some embodiments, the perforated barrier comprises a plurality of perforations therein that is configured to allow bidirectional flow of a liquid, for example a growth media through the perforations of the perforated barrier such that liquid can flow from the first chamber to the second chamber and also from the second chamber to the first chamber.

A skilled artisan would appreciate that the term "first chamber" as used herein, may in some embodiments be used interchangeable with the term "lower chamber" having all the same meanings and qualities thereof. A skilled artisan would appreciate that the term "second chamber" as used herein, may in some embodiments be used interchangeable with the term "upper chamber" having all the same meanings and qualities thereof. In some embodiments, cells are cultured in the second chamber of bioreactor vessel.

In some embodiments, the perforated barrier is configured to allow bidirectional flow of liquid including additional factors through the perforations of the perforated barrier such that liquid and additional factor or factors can flow from the first chamber to the second chamber and from the second chamber to the first chamber. In some embodiments, the perforation diameter is configured to allow liquid flow solely from the first chamber to the second chamber and from the second chamber to the first chamber. In some embodiments, the perforation diameter is configured to allow liquid including a factor or factors to flow solely from the first chamber to the second chamber and from the second chamber to the first chamber. In some embodiments, the factor or factors does not include cells or microorganisms. In some embodiments, the perforated barrier comprising a plurality of perforations, which do not allow cells or microorganisms grown in the vessel of the bioreactor to pass through the perforated barrier.

A skilled artisan would appreciate that flow may encompass flow of a liquid fluid comprising a growth media, a washing solution, a nutrient solution, a selection solution, an enzyme mixture solution, a collection solution, a final formulation solution, a storage solution, or any combination thereof. In some embodiments, a liquid comprises a growth media, a washing solution, a nutrient solution, a collection solution, a harvesting solution, a storage solution, or any combination thereof. In some embodiments, a liquid comprises additional factors, wherein non-limiting examples of factors that may be added include nutrients, gasses, activation factors, induction factors, antibiotics, antifungal agents, and salts. In some embodiments, any factor beneficial for the growth and collection of cells or microorganisms in bioreactor systems described herein may be added to a liquid. In some embodiments, a factor dissolves within the liquid, wherein the liquid represents a solvent and the factor a solute to form a solution. In some embodiments, a factor remains as a particulate within the liquid.

A skilled artisan would appreciate that the term "plurality" may encompass the number of perforations (pores) in a perforated barrier. In some embodiments, the plurality of perforations is determined based on a needed rate of exchange of media or other liquid flowing from a first chamber to a second chamber, or from a second chamber to a first chamber. In some embodiments, the plurality of perforations is determined based on the flow rate of media or other liquid flowing from a first chamber to a second chamber, or from a second chamber to a first chamber. In some embodiments, the plurality of perforations is determined based on the pattern of flow of media or other liquid flowing from a first chamber to a second chamber, or from a second chamber to a first chamber.

In some embodiments, the arrangement of perforations within a perforated barrier is configured to affect the pattern of flow of a media or other liquid flowing from a first chamber to a second chamber, or from a second chamber to a first chamber. In some embodiments, a perforated barrier comprises an evenly spaced plurality of perforations. In some embodiments, a perforated barrier comprises an uneven spacing of a plurality of perforations.

In some embodiments, the mean perforation diameter or effective mean diameter of the perforations in the perforated barrier is selected such that it does not allow cells or microorganisms grown in the bioreactor to pass through the perforated barrier. For example, in some embodiments, determining of the size of a perforation diameter comprises measuring a cell or microorganism size and determining a cell or microorganism shape, choosing a perforation diameter (perforation pore size) that would prevent the cell or microorganism from passing through a perforated barrier having the chosen pore size.

According to some related embodiments, the mean perforation diameter or effective mean diameter of the perforations in the perforated barrier is selected to be smaller than: 120 micrometer, or 100 micrometer or, 75 micrometer, or 50 micrometer, or 25 micrometer, or 15 micrometer. According to some related embodiments, the mean perforation diameter or effective mean diameter of the perforations in the perforated barrier is selected to be larger than: 0.1 micrometer, or 0.2 micrometer, or 0.3 micro meter or, 0.45 micrometer, or 0.75 micrometer or, 1.0 micrometer. According to some related embodiments, the mean perforation diameter or effective mean diameter of the perforations in the perforated barrier is selected between 0.1 micrometer and 120 micrometer. According to some related embodiments, the mean perforation diameter or the effective mean diameter of the perforations in the perforated barrier does not allow cells or microorganisms to pass from one chamber to a second chamber. For example, the mean perforation diameter or the effective mean diameter of the perforations in the perforated barrier is selected so that cells or microorganisms grown in an upper chamber may not pass into the lower chamber.

In some embodiments, the cell or microorganism have a spherical shape, accordingly the diameter of the cell or microorganism is used in determining perforation size. In some embodiments, the cell or microorganism may not have a spherical shape. In some embodiments, a cell or a microorganism may comprise a non-symmetrical shape, for example but in no way limiting a rod shape. Wherein a cell or a microorganism has a non-symmetrical shape, measurement for determining pore size would be based on the smallest diameter presented by a cell. In some embodiments, a cell may have the capacity to change shapes. Wherein a cell or a microorganism has the capacity to change shape, measurement for determining pore size would be based on the smallest diameter presented by the cell or microorganism that would allow passage of a cell or microorganism through a pore. In some embodiments, a cell or a microorganism may be deformable. Wherein a cell or a microorganism is deformable, cell size determination takes into account the diameter of the deformed cell or microorganism.

In some embodiments, a plurality of perforations comprises perforations of all the same size. In some embodiments, a plurality of perforation comprises perforations that am not all the same size. In some embodiments, perforations of different sizes comprise a random distribution. In some embodiments, the distribution of perforations of different sizes is determined based on fluid flow patterns from the flow of a liquid from a first chamber to the second chamber and from the second chamber to the first chamber.

In some embodiments, the shape of the perforations is symmetrical. In some embodiments, the shape of the perforations is non-symmetrical. In some embodiments, the shape of the perforation comprises a circular shape, an irregular in shape, an elliptical shape, or a polygonal. In some embodiment, a plurality of perforations comprises perforations all of the same shape. In some embodiment, a plurality of perforations comprises perforations of different shapes.

In some embodiments, the mean perforation diameter or effective mean diameter of the perforations in the perforated barrier is determined by selecting a diameter configured to allow the flow of a liquid from a first chamber to the second chamber and also from the second chamber to the first chamber, and does not allow cells or microorganisms grown in the bioreactor to pass through the perforated barrier. In some embodiments, the mean perforation diameter or effective mean diameter of the perforations in the perforated barrier is determined by selecting a diameter that allows for the flow of a liquid comprising additional factors from a first chamber to the second chamber and also from the second chamber to the first chamber, and does not allow cells or microorganisms grown in the bioreactor to pass through the perforated barrier. In some embodiments, the mean perforation diameter or effective mean diameter of the perforations in the perforated barrier is determined by selecting a diameter that allows for the flow of a liquid comprising additional factors and products produced from the cells or microorganisms from a first chamber to the second chamber and also from the second chamber to the first chamber, and does not allow cells or microorganisms grown in the bioreactor to pass through the perforated barrier.

In some embodiments, the perforation diameter (pore size) or effective mean diameter comprises about 0.1 to 40 micrometer. In some embodiments, the perforation diameter (pore size) or effective mean diameter comprises about 0.2 to 10 micrometer. In some embodiments, the perforation diameter (pore size) or effective mean diameter comprises about 10 to 40 micrometer. In some embodiments, the perforation diameter (pore size) or effective mean diameter is larger than 40 micrometers. In some embodiments, the perforation diameter (pore size) or effective mean diameter comprises about 40 to 60 micrometer. In some embodiments, the perforation diameter (pore size) or effective mean diameter comprises about 60 to 100 micrometer.

In some embodiments, the perforation diameter (pore size) or effective mean diameter is configured to prevent cells or microorganisms, to flow through the pore. In some embodiments, the perforation diameter or effective mean diameter is configured to prevent cells or microorganisms bound to beads to flow through the pore. In some embodiments, the pore diameter, of the perforations of a perforated barrier having a plurality of perforations therein, is configured to allow solely liquid flow from the first chamber to the second chamber and from the second chamber to the first chamber. In some embodiments the liquid can comprise solutes and/or added factors. In some embodiments, the pore diameter of the perforations of a perforated barrier having a plurality of perforations therein, is configured to allow solely liquid flow from the first chamber to the second chamber and from the second chamber to the first chamber, wherein the pore diameter is configure to not allow the passage of cells or microorganisms from the first chamber to the second chamber and from the second chamber to the first chamber.

In some embodiments, the perforated barrier is configured and useful, for example, in confining the grown cells to the second chamber within the reactor and in harvesting the cells. According to some embodiments, the present application also discloses bioreactor systems including the bioreactors and methods for growing cells or microorganisms in the bioreactors and bioreactor systems from isolation to final formulation.

In some embodiments, a bioreactor comprises an additional lower perforated barrier 12D below the perforated barrier 12 (which is present at the bottom of the upper chamber); see for example FIG. 1 (12) wherein the perforated barrier 12 comprises the bottom of the upper chamber. In some embodiments, the additional lower perforated barrier 12D is located between the bottom surface of the vessel (at the lower chamber) and the perforated barrier 12 (which is forming the bottom surface of the upper chamber); for example between 10B and 12 of FIG. 1. In some embodiments, the upstream flow of liquid from a lower chamber to an upper chamber passes through the two perforated barriers 12 and 12D. The additional lower perforated barrier 12D is configured to assist in aligning the flow of a liquid (straitening, providing linearity and uniform flow thereto) before it reaches the perforated barrier 12 that comprises the bottom of the upper chamber. This arrangement is configured to improve the linearity (and uniformity) of a liquid's flow. According to some embodiments, aligning the stream comprises providing an approximately even longitudinal flow rate along different radial locations of the perforated barrier [$v(r_1) \approx v\ r_2)$], or in other words the flow rate is substantially equal at every distance of the geometrical center of the perforated barrier. According to some embodiments the lower perforated barrier is sealingly attached to the walls of the lower chamber, and wherein its pores size is configured the prevent passage of cells or microorganism. According to some embodiments, both the perforated barrier 12 and the lower perforated barrier 12D are configured to align the liquid flow rate. According to some related embodiments, the mean perforation diameter or effective mean diameter of the perforations in the lower perforated barrier 12D is selected between 0.1 micrometer and 1 millimeter.

According to some embodiments, the lower perforated barrier 12D is configured to control the fluid velocity. A non limiting example for such a velocity controlling barrier 1600 is detailed in FIG. 16. As demonstrated in FIG. 16, the pores 1601 of a velocity controlling perforated barrier 1600 can comprise conical shapes; conical shape of the pores can be similar or different between the different pores, some pores can be similar and some can be different. According to some embodiments, the wider base of the conical pores is located at the bottom side of the barrier; such a configuration can provide the flow with an increasing flow rate towards the upper side of the barrier. According to some embodiments, pore/s 1602 closer to the center of the barrier can have a wider cone, or a wider opening at the upper side of the barrier, than of the peripheral pores 1601; such a configuration can provide an approximately even longitudinal flow rate along the different radial locations [$v(r_1) \approx v(r_2)$] of the perforated barrier 1600. According to such embodiments, a fluid impeller may not be required.

In some embodiments, the presences of the additional lower perforated barrier 12D is configured to trap air bubbles, air clusters, and debris which would otherwise clog and block flow through perforations of the upper perforated barrier 12 and interfere with the linearity and uniformity of flow.

Figure 15A:
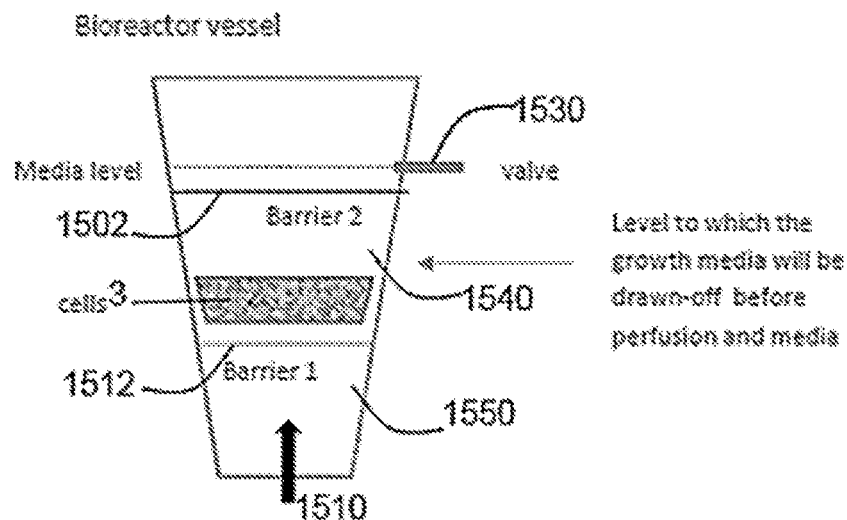
FIGS. 15A-15D present embodiments of processing of cells grown in a bioreactor.

In some embodiments, a bioreactor comprises an additional screening perforated barrier 1502 above the perforated barrier (first perforated barrier) 1512 (which is present at the bottom of the upper chamber), the screening perforated barrier is disposed sealingly to the walls of the upper chamber. FIG. 15A demonstrates the first perforated barrier 1512 and the additional screening perforated barrier 1502, which is positioned above the level of the cells mass 3. According to some embodiments, the additional screening perforated barrier 1502 is configured to prevent cells or microorganism passage for example to prevent the cells from leaving the bioreactor. In some embodiments, the bioreactor vessel is in an inverted position (See also Example 3 below) the flow of liquid is downstream 1520 (approximately with gravity direction) from an upper (the second 1540) chamber to a lower (the first 1550) chamber. This configuration is configured in some embodiments to be used during washing of cells or exchange of media or liquid solutions allowing wider surface area barrier, which enables to reduce a clogging of the barrier by the cell mass.

According to related embodiments, the bioreactor comprises, three perforated barriers:
- a primary perforated barrier 1512 (FIG. 15A), configured to separate between the upper and the lower chambers (1540,1550) of the bioreactor's vessel and to prevent passage of cells and microorganism there between;
- an upper perforated barrier 1502 (FIG. 15A), located in the upper chamber 1540 above cell mass 3 configured to prevent passage of cells and microorganism; therefore cell mass is kept between the primary and the upper perforated barriers (1512,1502) and;
- a lower perforated barrier 12D (FIG. 1), located in the first chamber 14A below primary perforated barrier 12, configured to align and/or control the fluid flow before reaching to the primary perforated barrier 12.

According to some related embodiments, the primary and the upper perforated barriers (1512, 1502, FIG. 15A) comprise similar pores size configured to prevent passage of cells or microorganisms.

According to some embodiments, the size of the pores of the lower perforated barrier (12D, FIG. 1) can be similar to—or can be different than—the size of the pores of the primary and the upper barriers (1512,1502, FIG. 15A).

One skilled in the art would appreciate that the range, shape, and distribution of pores may be similar or different between the different perforated barriers. In some embodiments, the diameter or effective diameter of the perforations (pores) of an additional perforated barrier comprise different sizes of pores than is present in the perforated barrier that separates the first and second chambers. In some embodiments, the diameter or effective diameter of the perforations (pores) of an additional perforated barrier comprise similar sizes of pores than perforated barrier that separates the first and second chambers. In some embodiments, the shape of the perforations (pores) of an additional perforated barrier comprises different shapes of pores than is present in the perforated barrier that separates the first and second chambers. In some embodiments, the shape of the perforations (pores) of an additional perforated barrier comprises similar shapes of pores than the perforated barrier that separates the first and second chambers. In some embodiments, the distribution of the perforations (pores) of an additional perforated barrier comprises different distribution of pores than is present in the perforated barrier that separates the first and second chambers. In some embodiments, the distribution of the perforations (pores) of an additional perforated barrier comprises similar distribution of pores than the perforated barrier that separates the first and second chambers.

In some embodiments, a bioreactor comprises an additional barrier with the second chamber above the cells and an additional barrier within the first chamber below the barrier that separates the first and second chambers.

One skilled in the art would appreciate that the surface area of an additional perforated barrier can be greater than or less than the surface area of the barrier that separates the first chamber from the second chamber. In some embodiments, an additional perforated barrier has a larger surface area than the surface area of the barrier that separates the first chamber from the second chamber. In some embodiments, an additional perforated barrier has a smaller surface area than the surface area of the barrier that separates the first chamber from the second chamber.

The disclosed bioreactors and bioreactor systems allows growing, processing and formulating the cells or other microorganisms in one closed single or multiple use system minimizing the risk of contamination and allowing efficient processing. According to some embodiments, bioreactors disclosed herein are configured to allow growing cells or other microorganisms to a desired concentration. In one embodiment, bioreactors disclosed herein provide a sterile environment. In one embodiment, bioreactor systems disclosed herein provide a sterile environment. Furthermore, as the cells or microorganisms are cultured and propagated they require more media and nutrients and larger culturing volumes. Some embodiments of the bioreactors described hereinafter include adaptive controlled volume changes (variable bioreactor volume) and media refreshment without the need to transfer the cells or microorganisms to a larger container.

In some embodiments, the bioreactors of the present application are configured to be used for growing non-adherent cells, which are suspended in the growth medium. In some embodiments, the bioreactors disclosed herein are configured to be used for growing adherent cells by including or adding a suitable cell supporting matrix into the second chamber of the bioreactor. The cell supporting matrix can be any type of cell supporting matrix known in the art to which the cells can adhere. If such a cell supporting matrix is being used in the bioreactor, it may be necessary to detach the cells from the cell supporting matrix by using detachment methods known in the art. As used herein, in some embodiments, the terms "cell supporting matrix" and "cell carrier matrix" and conjugates thereof may be used interchangeably having all the same meanings and qualities.

The bioreactors of the present application are configured to have a fixed volume or a variable volume. A skilled artisan would appreciate that in some embodiments, the terms "bioreactor" and "vessel" may be used interchangeably having all the same meanings and qualities. In embodiments wherein the bioreactor comprises a fixed volume, the rate of flow of a liquid, for example a growth medium can be controlled but the level and volume of the liquid, for example a growth medium in the bioreactor is substantially fixed. In embodiments wherein the bioreactor comprises a variable volume, the rate of flow of the liquid, for example a growth medium can be controlled and the level and volume of growth medium in the bioreactor can be variable. In some embodiments, variable the liquid levels, for example growth medium levels can be achieved by using multiple fluid outlet ports opening into the second chamber of the bioreactor at various different heights along the length of the walls of the bioreactor. A non-limiting example of this is presented in FIG. 2.

In some embodiments, the working volume of media is low, wherein cells are grown to high density cultures. In some embodiments, wherein the working volume is low, the rate of flow is also low or no flow at all. In some embodiments, the flow rate is low. In some embodiments, there is no flow from a first chamber to the second or from the second chamber to the first. In some embodiments, there is no flow from a first chamber to the second and from the second chamber to the first. In some embodiments, wherein the working volume is low, the medium is optimized for high density growth of cells. In some embodiments, wherein the working volume is low, cell growth is optimized for higher yields and lower media needs than are achievable in other bioreactors.

In some embodiments, when a culture comprises a small number of cells, for example less than the maximal number of cells that can be cultured in a bioreactor described herein, the cells are cultured in a low volume of growth media, as cells proliferate and the number of cells increases the volume within the chamber comprising the cells can be increased. At a point a flow cycle can be implemented, wherein the flow of liquid, for example growth media, increases as the quantity of cells increases. In some embodiments, nutrients can be added to the liquid, e.g., a growth media based on cell growth needs. In some embodiments, culturing cells in a bioreactor described herein maintains cells within a cell density range by adjusting the volume of liquid, e.g., growth media, within the bioreactor. In some embodiments, use of a flow cycle as described herein results in lower growth media needs for culturing an equivalent number of cells. In some embodiments, a flow cycle is used in a bioreactor described herein, wherein the supply of a growth media is regulated based on cells' needs. In other words, cells are fed only as needed. In some embodiments, the flow cycle controls the proliferation rate of cells.

According to some embodiments, each of the multiple outlet ports are configured to have a valve therein and configured be connected and disconnected fluidically to a common manifold feeding a pump. The level of a liquid, e.g., a growth medium in the bioreactor of such embodiments can be varied by suitably opening the valve of a selected fluid outlet port and closing all the valves of the remaining fluid outlet ports. According to some embodiments, controlling the volume of a liquid, e.g., a growth medium in the bioreactor advantageously allows expanding the culture as the cells continue to proliferate without opening the bioreactor and without the need of using methods used in other bioreactor systems, such as, for example cell passaging and dish/container replacement.

In some embodiments, the bioreactors are configured to include a fluid impeller or fluid disperser disposed in the first (lower) chamber of the bioreactor's vessel. In some embodiments, the bioreactor is configured to include an oxygenating system for oxygenating the growth medium.

Bubbles may in certain embodiments be created by the oxygenating system. Bubbles in a lower chamber may in some embodiments, have a negative impact on a bioreactor, as the bubbles may stick to a perforated barrier and interfere with the flow of liquid from one chamber to the next chamber. Additionally, nano bubbles that pass through the perforations of the barrier tend to lift cells up, which may interfere with the high density growth of a floating cell cake.

According to some embodiments, the lower perforated 12D (FIG. 1) is configured to prevent passage of bubbles created or formed in the lower chamber from reaching and blocking the perforated barrier 12; bubbles created for example by the oxygenating system. According to some embodiments, bubbles with an approximate diameter of several nanometers do pass the lower perforated barrier 12D and the perforated barrier 12 and assist in lifting the cells or microorganism up the liquid's flow.

According to some embodiments, the bioreactors disclosed herein are configured to have various different shapes and at least the portions of the walls of the bioreactors, which define the second chamber is configured to be straight (vertical) or configured to be slanted at an angle to the vertical (or slanted with respect to a longitudinal axis of the bioreactor). In some embodiments, some of the walls surrounding the second chambers are configured to be vertical and some of the walls are configured to be slanted. Non-limiting examples of shapes of the bioreactor vessel are presented in FIG. 4A (304A and 304B), FIG. 4B (314A and 314B), FIG. 4C (324A and 324B), FIG. 4D (334A and 334B), FIG. 4E (344A and 344B), FIG. 4F (354A and 354B), FIG. 4G (364A and 364B), FIG. 4H (374A and 374B), FIG. 4I (384A and 30B).

The upward increasing transversal cross-sectional area of the second chamber in such embodiments is configured to allow a fluid velocity gradient to be established along the vertical direction (along the longitudinal axis of the bioreactor), such that the growth medium flow velocity decreases with increasing transversal cross-sectional area. According to some embodiments, this flow velocity gradient combined with the gravitational force acting on the cells suspended in the growth medium assists in suspending the cells at some desired region within the volume of growth medium contained in the second chamber. In some embodiments, regulation of flow rates of medium maintains cells in a desired position within a bioreactor. In some embodiments, regulation of flow rates of medium maintains cells in a desired position within a bioreactor. In some embodiments, regulation of flow rates in relation to the radius of the bioreactor, or chamber thereof, of medium maintains cells in a desired position within a bioreactor.

In some embodiments, the desired position is lower than the exit port. For example see FIG. 1, if cells suspended within a liquid rise within the upper chamber at a flow rate of 1 mm per min (middle set of arrows 37B), in the lower part there can be for example a flow rate of 3 mm per min (arrows at the level of the barrier 37A), in the middle a flow rate of 1 mm per min (37B), and a few cm above were the media exits the chamber via a port/valve the flow rate can be 0.2 mm per min (would be above upper set of arrows 37C and above the level of the exit port 26). In some embodiments, the position of the cells is determined by the flow rate. In some embodiments, the position of the cells is lower than the exit port. A position for cells lower than the exit port can be desired when washing cells, when removing subpopulations of cells, when exchanging a liquid, when adding factors, or any combination thereof.

A skilled artisan would appreciate that a cell population may comprise cells of different sizes, charge, and mass. In some embodiments, cells can be separated within different positions within a bioreactor disclosed herein, based on cell characteristics including size, charge, and mass. In some embodiments, cells are maintained within different positions within a bioreactor disclosed herein based on cell characteristics including size, charge, and mass.

A skilled artisan would appreciate that cell size varies based on the type of cell. For example a red blood cell is about 6-8 mm in diameter, a T-lymphocyte is about 9-12 mm in diameter, a mesenchymal stem cell (MSC) is about 15-21 mm in diameter, and a macrophage is about 50 mm in diameter. The volume between cells can be dramatically different as well. In some embodiments, a bioreactor system disclosed herein is configured to be used to separate blood cells by regulating the flow rate.

In some embodiments, the flow rate comprises a range of about 0.01 mm per minute to 50 mm per minute. In some embodiment, the flow rate comprises a range of about 0.01 mm/min to 0.1 mm/min. In some embodiment, the flow rate comprises a range of about 0.1 mm/min to 1.0 mm/min. In some embodiment, the flow rate comprises a range of about 1.0 mm/min to 2.0 mm/min. In some embodiment, the flow rate comprises a range of about 2.0 mm/min to 3.0 mm/min. In some embodiment, the flow rate comprises a range of about 3.0 mm/min to 4.0 mm/min. In some embodiment, the flow rate comprises a range of about 4.0 mm/min to 5.0 mm/min. In some embodiment, the flow rate comprises a range of about 5.0 mm/min to 10.0 mm/min. In some embodiment, the flow rate comprises a range of about 10 mm/min to 15 mm/min. In some embodiment, the flow rate comprises a range of about 15 mm/min to 20 mm/min. In some embodiment, in the flow rate comprises a range of about 20 mm/min to 25 mm/min. In some embodiment, the flow rate comprises a range of about 25 mm/min to 30 mm/min. In some embodiment, the flow rate comprises a range of about 30 mm/min to 35 mm/min. In some embodiment, the flow rate comprises a range of about 35 mm/min to 40 mm/min. In some embodiment, the flow rate comprises a range of about 40 mm/min to 45 mm/min. In some embodiment, the flow rate comprises a range of about 45 mm/min to 50 mm/min.

In some embodiments, the flow rate within a bioreactor is different in different positions within the bioreactor (See for example FIG. 1 and the accompanying explanation thereof below, and the representative flow rate arrows 37A, 37B, and 37C, or FIG. 13 and representative flow rate arrows 37A and 37C).

In some embodiments, the size, charge, and/or mass of a population of cells can be artificially changed. For example, in some embodiments, cells can be cultured with beads, wherein the cells bind to the beads resulting in cell-bead complexes having a higher mass and different shape then the cells not attached to beads. In some embodiments, 100% of cells are bound to a bead. In some embodiments, a sub-set of cells are bound to a bead. In some embodiments, at least 90% of cells, 80% of cells, 70% of cells, 60% of cells, 50% of cells, 40% of cells, 30% of cells, 20% of cells, or 10% of cells are bound to a bead. In some embodiments, less than 10% of cells are bound to a bead.

In some embodiments, cells bound to beads are excluded from collection of the final cell population. In some embodiments, cells bound to beads are the cells desired to be collected as the final cell population. For example, in one embodiment, following addition of beads, wherein a subpopulation of cells binds to the beads in a specific fashion, increasing the flow rate will result in the cells not bound to beads rising at an increased rate compared with the cells bound to the beads, so these non-bound cells can exit the vessel chamber from an exit port wherein the bound cells remain in a position lower than the exit port. In some embodiments, the non-bound cells are collected upon exiting the bioreactor chamber. In some embodiments, the non-bound cells are disposed of upon exiting the bioreactor chamber and the bound cells are harvested.

In some embodiments, the surface of beads can comprise an antibody, a receptor ligand, a carbohydrate binding molecule, a lectin, or a component of a binding pair for example biotin. In some embodiments, the surface of beads comprises a positive surface charge. In some embodiments, binding between beads and cells or a subpopulation thereof is reversible. In some embodiments, binding between beads and cells or a subpopulation thereof is irreversible.

In some embodiments, bioreactors are configured to include one or more harvesting ports that are configured to open into the second chamber at the vicinity of the perforated barrier, or, alternatively, are configured to open at the upper surface of the perforated barrier. Non-limiting examples of harvesting ports that are configured to open into the second chamber or at the upper surface of the perforated barrier are presented in FIG. 1 (21), FIG. 2 (127), FIG. 6A and FIG. 6B (521), FIGS. 6C and 6D (531), FIGS. 7 (627), FIG. 8 (727), FIG. 9 (827), FIGS. 10A and 10B (927), FIGS. 11A and 11B (927), and FIGS. 12A and 12B (1127).

In accordance with some embodiments, the entire reactor or perforated barrier are configured to be tiltable at an angle to the vertical to assist the harvesting of the cells. In some embodiments, harvesting of the cells, microorganisms, or products thereof, grown in a bioreactor disclosed herein comprises sterile harvesting of the cells, microorganisms, or products thereof. Non-limiting examples of perforated barriers are presented in FIG. 1(12), FIG. 7 (612), FIG. 8 (712), FIG. 9 (812). FIGS. 10A and 10B (912), FIGS. 11A and 11B (1012), and FIGS. 12A and 12B (1112).

In accordance with some embodiments of the bioreactor, the perforated barrier is configured to be a fixed (non-movable) barrier. In some embodiments, a fixed perforated barrier is sealingly attached to the vessel walls. In accordance with some other embodiments, the perforated barrier is configured to be a movable and/or tiltable perforated barrier. In accordance with some embodiments of the bioreactor fixed perforated barriers is configured to be a flat perforated barrier, a flat perforated barrier inclined at an angle to a longitudinal axis of the bioreactor, a concave perforated barrier with a concave upper surface facing the top of the bioreactor, a tapering perforated barrier, or a conical perforated barrier, or any combination thereof.

In accordance with some embodiments of the bioreactor, the movable perforated barriers are configured to be a movable perforated barrier sealingly attached to the vessel walls of the bioreactor by a flexible and/or stretchable member. The flexible and/or stretchable member is scalingly attached to a perimeter of the perforated barrier and sealingly attached to the vessel wall. In accordance with some embodiments of the bioreactor, the movable perforated barrier is configured to be a deformable and/or flexible perforated barrier, or a convex buckling perforated barrier with a convex upper surface facing the top of the bioreactor.

A skilled artisan would appreciate that the term "sealingly" and different grammatical forms thereof, refers to an attachment between the barrier and the vessel wall wherein there is no flow through the barrier of any kind of material unless through perforations.

In some embodiments, bioreactor systems including the bioreactors of the present application are configured to also include temperature control systems, pumps for circulating the growth medium, one or more fluid reservoirs connectable to the bioreactor for introducing volumes of growth medium and/or additives and/or substances required for maintaining the level of nutrients and/or any other materials necessary for cell growth.

Other substances required for any steps of growing and/or maintaining, washing, and/or proliferating and/or differentiating and/or activating and/or detaching the cells for harvesting can also be added through such fluid reservoirs, including various enzymes, growth factors, activating factors, differentiating factors, washing buffers, pH adjustments, dissolved Oxygen adjustments, Nutrients or any other necessary substances or compounds. In some embodiments, living cells can also be added for co-culturing with or activating the cells within the bioreactor. In some embodiments, other substances required for inducing and/or maintaining induction of a cell product or microorganism product can also be added to medium within the bioreactor.

In some embodiments, bioreactor systems disclosed herein are configured to also include a controller for controlling the operation of the bioreactor, for opening and/or closing various different valves of the bioreactor, for controlling the flow of growth medium or other fluids through the bioreactor by controlling the pump and/or various different valves. As used herein, one skilled in the art would appreciate that the term "flow velocity" may be used interchangeable with "flow rate" having all the same meanings and qualities. As used herein, one skilled in the art would appreciate that the term "perforations" may be used interchangeable with "pores" having all the same meanings and qualities.

In some embodiments, the flow rate directly or indirectly influences the density of cells cultured in a bioreactor disclosed herein. In some embodiments, a low flow rate is used to culture very high density cell cultures.

In some embodiments, bioreactor systems and bioreactors disclosed herein are configured to also include one or more sensors suitably connected to the controller for monitoring and/or regulating various physical and/or chemical parameters within the growth medium (such as, for example, temperature, pH, glucose concentration, dissolved oxygen concentration the concentration of dissolved carbon dioxide or of $HCO_3$ ions, the concentration of lactate, and ionic strength) in the growth medium, all can be sensed monitored and controlled in the bioreactor and/or bioreactor headspace and/or in a fluid reservoir connectable to the bioreactor and/or at the various inlets or outlet ports. In some embodiments, sensors are configured to detect a product synthesized by a cell or microorganism grown in the bioreactor. In some embodiments, control of some of the features above may require mixing of the growth medium, the mixing can be provided at the fluid reservoir.

Unless otherwise defined, all technical and/or scientific terms used herein have the same meaning as commonly understood by one of ordinary skill in the art to which the bioreactors and systems thereof pertains. FIGS. 1-16 and the accompanying description thereof, provide numerous embodiments of bioreactors and systems thereof. A skilled artisan would recognize that other methods and materials similar or equivalent to those described herein can be used in the practice or testing of embodiments disclosed herein. In addition, the materials, methods, and examples are illustrative only and are not intended to be necessarily limiting.

Implementation of the method and/or system of embodiments of the bioreactor and systems thereof disclosed herein can involve performing or completing selected tasks manually, automatically, or a combination thereof. Moreover, according to actual instrumentation and equipment of embodiments of the method and/or system disclosed herein, several selected tasks could be implemented by hardware, by software or by firmware or by a combination thereof using an operating system.

For example, hardware for performing selected tasks according to some embodiments could be implemented as a chip or a circuit. As software, selected tasks according to some embodiments could be implemented as a plurality of software instructions being executed by a computer using any suitable operating system.

In one embodiment, one or more tasks according to the methods and/or systems as described herein, can be performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Reference is now made to FIG. 1, which is a schematic part cross-sectional diagram illustrating a bioreactor system including a bioreactor having a perforated barrier, in accordance with some embodiments of the bioreactors of the present application. According to some embodiments, the bioreactor system 50 includes a bioreactor 10, a pump 4, a controller 30 and a growth medium reservoir 20.

The pump 4 can be any type of fluid pump known in the art and capable of receiving a fluid such as a growth medium received at the pump's inlet port and pumping it through an outlet port thereof at a controllable pumping rate without compromising the sterility of the growth medium. For example, the pump 4 can be a variable flow rate peristaltic pump, such as, for example, a model 530 process pump commercially available from Watson-Marlow fluid technology group (UK) or any other suitable type of pump known in the art.

The bioreactor 10 has a bioreactor wall 10A having a bottom part 10B and a top part 10C. In the embodiment of the bioreactor presented in FIG. 1, the bioreactor 10 comprises a top part 10C that has a threaded opening 10E into which a threaded cover 10D is sealingly threaded. The cover 10D is configured to also (optionally) have one or more openings therein such as for example, the opening 10F into, which a sensor unit 22 is configured to be sealingly inserted into the volume enclosed within the walls 10A of the bioreactor 10. According to some embodiments, the threaded opening 10G is configured to be sealed by a threaded sealing cap 10H when not in use. The bioreactor cover 10D is configured to (optionally) include several additional sealable openings (not shown in FIG. 1), which are configured to be used for inserting therein additional sensors (not shown in FIG. 1), or other needed devices such as, for example, a heating unit (not shown) an oxygenating unit (not shown), a thermometer (not shown) or any other device needed for operating the bioreactor 10 and/or monitoring the contents of the bioreactor 10 and/or ports allowing sampling and introduction of materials to the content of bioreactor 10.

According to some embodiments, the bioreactor 10 can be made from any suitable biocompatible material known in the art, such as a suitably biocompatible plastic or polymer based material. In some embodiments, the reactor 10 is made from a transparent material to enable an operator to see the contents of the bioreactor 10. In some embodiments, non-limiting examples of materials that can be used in the construction of the bioreactor 10 include but are not limited to, polystyrene, stainless steel, polyetheretherketone (PEEK), polysulfone, and various types of polytetrafluoroethylene (PTFE) plastics, for example Rulon®. In some embodiments, materials for use in the construction of a bioreactor described herein are selected based on their low coefficient of friction, excellent abrasion resistance, Gamma radiation sterilization, wide range of operating temperatures, or chemical inertness, or any combination thereof.

The bioreactor 10 further comprises a perforated barrier 12 sealingly attached to the walls 10A of the bioreactor 10. The perforated barrier 12 divides the volume enclosed within the bioreactor 10 into a first (lower) chamber 14A and a second (upper) chamber 14B. The perforated barrier 12 is made from a material which has multiple perforations therein. The average diameter of the perforations formed in the perforated barrier 12 is selected such that the cells 3 (or microorganisms) suspended in a growth medium 2 cannot penetrate into the perforations of the perforated barrier 12, while the growth medium 2 can flow into and through the perforations. The perforated barrier 12 operates as a cell (or microorganism) barrier while allowing the growth medium 2 to flow and pass there through. According to some embodiments the construction of the perforated barrier 12 is also configured to align a medium flow. According to some embodiments, the alignment comprises improving the linearity and uniformity of a medium flow towards the cell mass 3 and throughout the upper chamber.

The perforated barrier 12 can be made from any suitable perforated biocompatible material, such as, for example, a suitable biocompatible plastic or polymer based material having a selected perforation average perforation (or pore) diameter. The thickness and strength of the perforated barrier 12 and the type of perforated material selected for the perforated barrier 12 can depend, for example, on the average size of the cells or microorganisms to be grown in the bioreactor 12, the desired rate of flow of the growth medium 2 through the bioreactor, the maximal allowable level of pressure of the growth medium within the first chamber 14A, or the method of harvesting cells or microorganisms as implemented in the design of the bioreactor, or any combination thereof. For example, if the perforated barrier needs to be flexible as explained in detail hereinafter (See for example FIGS. 7-8), a thinner perforated barrier can be selected for use. In some embodiments, the types of materials from which the perforated barriers can be made can include but are not limited to cellulose nitrate, cellulose acetate, polytetrafluorethylene (FTFE), hydrophobic FIFE, hydrophilic FTFE, aliphatic or semi-aromaticpolyamides— for example Nylon®, polycarbonate, polysulfone, polyethylene, polyethersoulfone, polyvinylidene, stainless steel, and regenerated cellulose.

In some embodiments, the thickness of the perforated barrier 12 can be in the range of 0.5-5.0 millimeter. In other embodiments, thinner perforated barriers can be used depending on the application, the mechanical properties of the material from which the perforated barrier is made, total surface area and shape of the perforated barrier and other considerations. In other embodiments, thicker perforated barriers can be used depending on the application, the mechanical properties of the material from which the perforated barrier is made, total surface area and shape of the perforated barrier and other considerations.

The bioreactor 10 has a fluid inlet port 16 through which growth medium 2 can be pumped into the first chamber 14A. The fluid inlet port 16 is configured to receive the growth medium 2 under pressure from the pump 4 of the bioreactor system 50. The growth medium entering the fluid inlet port 16 can pass into a fluid impeller 18 disposed within the first chamber 14A. The (optional) fluid impeller 18 is configured to be a hollow disc-like perforated member having multiple passages 18P therein.

The fluid impeller 18 is configured to receive growth medium 2 from the inlet port 16 and disperse the growth medium 2 through the multiple perforations 18P in multiple jets 19 of growth medium to enhance the mixing of the growth medium 2 entering the inlet port 16 with the growth medium 2 disposed within the chamber 14A. It is noted to that the specific structure of fluid impeller 18 illustrated in FIG. 1 is one embodiment of a fluid impeller and not obligatory. Many other different types of fluid impellers/dispersers having various different shapes, structures, dimensions and using passages and/or nozzles can be used, as is well known in the art including impeller types such as a pinch blade or marine type.

According to some embodiments, in operation of the system 50, cells (or microorganisms) are suspended in a growth medium and placed within the second (upper) chamber 14B of the bioreactor 10 by inserting the suspended cells through the opening 10E or through the opening 10G of the cover 10D (which can then be sealed with the cap 10H). Alternatively, the cell suspension can be inserted into the second (upper) chamber 14B through any other suitable port, such as for example, a harvesting port 21 opening into the second chamber 14B just above the surface 12A of the perforated barrier 12. The growth medium 2 injected into the chamber 14B by the fluid impeller 18 increases the pressure of the growth medium 2 in the first chamber 14A and causes the growth medium 2 to flow through the perforations of the perforated member 12 into the second chamber 14B effectively perfusing the cells mass 3 suspended in the growth medium 2 held within the second chamber 14B. The growth medium 2 rises within the second chamber 14B and reaches the level of a fluid outlet 26, where it is drained out of the bioreactor 10 and carried by a conduit 28 to the pump 4 where it is recirculated into the bioreactor 12 through the inlet port 16.

In some embodiments, the bioreactor 10 has a generally frustoconical shape. The diameter of the bottom part 10B is smaller than the diameter of the top part 10C and the walls 10A are sloped. Due to the frustoconical shape of the bioreactor, the diameter of the bioreactor increases as the growth medium moves upwards (towards the top part 10D) within the bioreactor.

As the pump 4 pushes the growth medium into the inlet port 16 at a constant flow rate, the flow velocity (fluid velocity) of the growth medium 2 adjacent the surface 12A of the perforated barrier 12 is higher than the flow speed of the growth medium near the top part 10D, effectively resulting in establishing a fluid flow velocity gradient along the longitudinal axis 35 of the bioreactor 10. The flow velocity gradient is schematically indicated by the length and thickness of the solid arrows 37A, 37B and 37C. The flow velocity represented by the arrow 37A is greater than the flow velocity represented by the arrow 37B and the flow velocity represented by the arrow 37B is greater than the flow velocity represented by the arrow 37C.

The suspended cells 3 are carried upwards by the upward moving flow of the growth medium 2, which counteracts the tendency of the cells 3 (which have a higher specific gravity than the specific gravity of the growth medium 2) to move downwards and to settle on the surface 12A due to the force of gravity acting on the cells 3. The flow rate of the growth medium can therefore be controlled and adjusted to result in an adequate suspension of the cells within the volume of the growth medium 2 contained in the second chamber 14B avoiding the settling of the cells 3 on the surface 12A of the perforated barrier 12, while leaving most of the cells 3 suspended in the growth medium 2 at a region within the chamber 14B, which is adequately lower than the upper surface 2A of the growth medium 2 so as to minimize or adequately reduce the number of cells entering the fluid outlet port 26 (which greatly reduces loss of cells 3). According to some embodiments the outlet port 26 comprises a perforated barrier or filter (not shown), configured to prevent the cells or microorganisms from leaving the bioreactor. In some embodiments, the flow rate of the growth medium 2 through the second chamber 14B is low enough to avoid substantial shear forces which can be detrimental to the cells 3.

When the proper flow rate of the growth medium 2 through the bioreactor 10 is established, the pump 4 circulates the growth medium 2 through the volume of the bioreactor 10 by pumping any growth medium 2 exiting the fluid outlet port 26 back into the bioreactor through the fluid inlet port 16 in a closed loop. During the cell growth, when there arises a need to add new nutrients to the growth medium 2 (to compensate for depletion thereof by absorption into cells) or to add activating substances or any other additive or substance into the growth medium 2, this can be done by flowing some fresh growth medium 2 from the medium reservoir 20 of the system 50 by way of a media tube (38).

The medium reservoir 20 is configured to be connected to an inlet port 4A of the pump 4 by a suitable hollow conduit 38. A suitable controllable valve (or stopcock) 39 is configured to be attached between the conduit 38 and the pump inlet 4A, such that the flow of growth medium from the fluid reservoir 20 into the pump inlet port 4A can be controlled. The valve 39 is configured to be controllably closed to stop feeding fluid from fluid reservoir 20 into the pump inlet port 4A or is configured to be opened to enable feeding fluid from fluid reservoir 20 into the pump inlet port 4A allowing media refreshment and high density cell culturing.

In some embodiments, regulation of flow rates correlates with the density of cells being grown and propagated. In some embodiments, very low flow rates provide for high density culturing of cells in the bioreactors disclosed herein. In some embodiments, the working volume of media in which the cells are grown is low, as is the flow rate allowing for the maintenance of high density culturing of cells. This low working volume and low flow rate, can in certain embodiments, lead to higher yields and lower media needs. In some embodiments, the bioreactors disclosed herein and methods of use thereof, are advantageous compared with other bioreactors known in the art due to their ability achieve and maintain high density cultures of cells or organisms, which results in higher yield and lower media needs. In some embodiments, a bioreactor disclosed herein comprises a smaller physical footprint minimizing the bioreactor size, and thereby reducing media use.

According to some embodiments, the bioreactor 10 is configured to also (optionally) include an additional outlet port 27 opening at the bottom part 10B of the bioreactor. The outlet port 27 includes a valve (or stopcock) 25 that is configured to allow draining an amount of the growth medium 2 from the first chamber 14A of the bioreactor 10 if necessary. For example, if an amount of new growth medium 2 is added to the bioreactor 10 from the fluid reservoir 20, a similar amount of growth medium can be bled out of the bioreactor 10 to restore the level of growth medium 2 within the second chamber 14B.

According to some embodiments, growth medium 2 can also be bled out of the bioreactor 10 through the outlet port 25 when it is desired to reduce the total volume of the growth medium 2 within the second chamber 14B in order to concentrate the cells 3 for cell harvesting. When such a cell concentrating is performed, the smaller volume of the growth medium 2 remaining in the lower part of the second chamber 14B has a higher cell court (in cells/ml of growth medium) since the cells 3 cannot pass the perforated barrier 12 and are therefore concentrating. The concentrated suspension of cells 3 remaining in the chamber 14B can then be harvested through the harvesting port 21 which is configured to include a valve (or stopcock) 23 as illustrated in FIG. 1.

In some embodiments, in order to prevent clogging the perforated barrier 12 most the growth medium can be drained via at least one of the outlet ports 126A-126D (detailed in the following), and only a minimal volume of the growth medium may be drained via outlet port 25.

It is noted that while any desired additives and/or substances can be introduced into the bioreactor 10 by introducing such substances and/or additives into the growth medium 2 held within the fluid reservoir 20 and allowing a volume of the growth medium 2 including such substances and/or additives to flow into the chamber 14A, as disclosed hereinabove, it can also be possible to directly introduce such substances and/or additives into the bioreactor by introducing a relatively small volume of fluid or growth medium including a suitably high concentration of the substances and/or additives into the bioreactor 10 through any suitable opening or inlet port of the bioreactor 10 and allowing the added small volume to mix with the volume of growth medium 2 circulating within the reactor to reach the desired concentration. For example, such small volumes of fluid or growth medium including additives and/or substances can be introduced though the opening 10G by temporarily removing the cap 10H and resealing the opening 10G.

In some other embodiments, the cap 10H is configured to include a penetrable sealing diaphragm (not shown in detail in FIG. 1) made from rubber, latex or any other suitable sealing material as is known in the art and commonly used in bottles containing injectable liquid formulations and the small volume of fluid with substances and/or additives can be loaded within a sterile syringe having a sterilized needle and where the needle is configured to be pushed into the sealing diaphragm of the cap until it penetrates the sealing diaphragm, the contents of the syringe can then be injected into the growth medium 2 within the second chamber 14B, and the needle of the injector can be withdrawn from the sealing membrane as is known in the art. This method can advantageously reduce the risk of contamination of the growth medium by any undesirable microorganisms. Additionally, cap 10H is configured to have a deep tube touching the growth medium 2 with a one way seal allowing media sampling in a sterile way.

In some other embodiments, the cap 10H is configured to include a filter (not shown in FIG. 1). The cap's filter is configured to allow a flow of air to the headspace (space between the bioreactor top 10C and the media's surface) or for reduction pressure from the headspace.

According to some embodiments, the bioreactor system 50 is configured to use the controller 30 and the sensor unit 22 for monitoring the operation of the system. The sensor unit 22 is configured to include a sensor or multiple sensors (the individual sensors are not shown in detail in FIG. 1 for the sake of clarity of illustration), which can be disposed in several locations for example: via the end part 22A of the sensor unit 22 that is immersed in the growth medium 2, or via at least one of the outlet ports (126A-126D), or via harvesting port (21), or via inlet port (116), or via outlet port (27) or via side wall (10A) or any combination thereof. The sensor(s) of the sensor unit 22 can be used to determine the concentration of several chemical species within the growth medium 2, such as, for example, the concentration of $H^+$ ions (to determine the pH of the growth medium 2), the concentration of dissolved oxygen in the growth medium 2, the concentration of dissolved carbon dioxide in the growth medium 2 or of $HCO_3^-$ ions in the growth medium 2, the concentration of glucose, the concentration of lactate, and ionic strength. Such sensor or sensors can be single use sensors using optic sensing without the need to penetrate the wall or can be located on 10A touching the liquid. According to some embodiments, the sensors of the sensor unit 22 are configured to also be sensors for sensing physical parameters of the growth medium 2, such as but not limited to, the temperature and/or the turbidity and/or the optical density of the growth medium 2, and/or any other desired physical parameter of the growth medium 2 such as, conductivity, capacitance, pressure, flow rates, viscosity, turbidity and others.

According to some embodiments, the signal(s) from the sensor unit 22 representing any of the chemical and/or physical parameters sensed by the sensors can be fed into the controller 30 by suitable electrical conductors (or conductor pairs) 22B. The controller 30 is configured to process such sensor signals to determine of the values of the sensed parameters as is well known in the art.

According to some embodiments, the controller 30 is configured to be or configured to include one or more processing devices such as, for example, a microprocessor or a microcontroller or a digital signal processor, a personal computer or any other suitable means for processing received signals and any type of memory device known in the art for storing any computed data therein for the purpose of off-line or on-line presentation of all determined sensor data and the history of operation of the bioreactor (including, but not limited to, the rate of flow of growth medium 2 through the bioreactor 10, the time of introducing and the volume of growth medium from the fluid reservoir 20, the time of introducing and the volume and concentration of any other added substance or additive during the operation of the system 50).

According to some embodiments, the controller 30 is configured to also include any display device known in the art for displaying processed results and the values of any sensed parameters to an operator or user of the system 50. The controller 30 is configured to also include one or more user interface device (such as, but not limited to a mouse, a light pen, a pointing device, a keyboard, a touch sensitive screen, or any other input device known in the art) which is configured to be used by the user or operator of the system 50 for inputting data and/or suitable commands into the controller 30. For example, the user can control the rate of flow of the growth medium 2 through the bioreactor 10 by entering suitable commands into the controller 30 resulting in suitable control signals being sent by the controller 30 to the pump 4 through a communication line 29 connecting the controller and the pump 4.

In some embodiments of the systems of the present application, the valves 23, 24, 25, and 39 of the system 50 are configured to be manual valves or stopcocks, which can be manually closed or opened. In some other embodiments, one or more of the valves 23, 24, 25, and 39 are configured to be electrically operated valves that can be operated by receiving appropriate command signals from the controller 30.

For example, any of the valves 23, 24, 25, and 39 can be electrically operable solenoid based valves which can be opened and/or closed controllably and/or automatically by applying suitable voltage or current signals to the solenoids by the controller 30. It is noted that for the sake of clarity of illustration any electrical wires connected between the controller 30 and any of the valves 23, 24, 25, and 39 are not shown in FIG. 1. However, such optional connections are shown in the schematic diagram of FIG. 5.

It is noted that while in the bioreactor system 50 the level of the upper surface 2A of growth medium 2 in the second chamber 14B is fixed, this is not obligatory and in some embodiments of the bioreactor systems, the level (height) of the growth medium in the bioreactor can be controllably changed.

Reference is now made to FIG. 2, which is a schematic part cross-sectional diagram illustrating a bioreactor system having a bioreactor with multiple fluid outlet ports for controllably adjusting the level of the growth medium in the bioreactor, in accordance with some embodiments of the bioreactors of the present application.

According to some embodiments, the bioreactor system 150 includes a bioreactor 110, the controller 30 as disclosed in detail hereinabove, the pump 4 as disclosed in detail hereinabove and the fluid reservoir 20 as disclosed in detail hereinabove. The bioreactor system 150 is configured to also include an oxygenating system 160. The bioreactor 110 can be made from any of the materials disclosed in detail hereinabove for the bioreactor 110. The bioreactor 110 has a bioreactor wall 110A, a bottom part 110B and a bioreactor top part 110C. According to some embodiments, the top part 110C is configured to have a threaded opening 110F therein for sealingly inserting there through a threaded sensor unit 122. A top opening in the top of the bioreactor 110D can be effectively closed using a cap 110E, wherein the seal of the opening in the head plate of the bioreactor is represented by 110G.

According to some embodiments, the sensor unit 122 is configured to include any number of sensors (not shown individually in FIG. 2 for the sake of clarity of illustration) attached to or included in the end 122A of the sensor unit 122 for sensing any desired chemical or physical property of the growth medium 2 within, which the end 122A of the sensor unit 122 can be immersed. It is noted that the position of the end 122A can be changed by threading the sensor unit 122 up or down within the threaded opening 110F such that the end 122A can be immersed in the growth medium 2 at any level of the growth medium 2 within the bioreactor 110.

A perforated barrier 112 is sealingly attached to the wall 110A of the bioreactor 110 such that the perforated barrier 112 divides the internal volume of the bioreactor 110 into a first (lower) chamber 114A and a second (upper) chamber 114B, as disclosed in detail hereinabove for the bioreactor 10 and the perforated barrier 12 of the bioreactor system 150. According to some embodiments, the perforated barrier 112 can be made from similar material(s) and can have similar perforation mean sizes as disclosed in detail hereinabove for the perforated barrier 12.

However, according to some embodiments, while the bioreactor 10 (of FIG. 1) has a single fluid outlet port 26 in the second chamber 14B, the bioreactor 110 has plurality of different fluid outlet ports at different heights and corresponding valves, for example four different fluid outlet ports 126A, 126B, 126C and 126D in the second chamber 114B. The outlet ports 126A, 126B, 126C and 126D are disposed along the length of the second chamber 114B at different positions and each of the fluid outlet ports outlet ports 126A, 126B, 126C and 126D has a corresponding valve 124A, 124B, 124C and 124D (respectively) attached thereto. The valves 124A, 124B, 124C and 124D are fluidically connected to a common fluid manifold 128 which is fluidically connected to the pump 4. The arrangement of the four valves 124A, 124B, 124C and 124D at different positions allows the level of the growth medium 2 to be selected from four different levels schematically represented in FIG. 2 by the dashed lines A, B, and C and the line D.

In some embodiments, if the valve 124D is opened and the valves 124A, 124B, 124C are closed (as illustrated in FIG. 2), the growth medium 2 reaches the level represented by the solid line D and the growth medium 2 leaving the second chamber 114B through the fluid outlet port 126D enters the manifold 128 and is re-circulated into the bioreactor 110 by the pump 4 pumping the growth medium 2 through the pump outlet 4B into the fluid inlet port 116 and through the perforations 19 the fluid impeller 18.

In some embodiments, if it is desired to increase the level of growth medium 2 in the second chamber 114B, the valves 126A, 126B and 126D can be closed and the valve 126C can be opened while the valve 39 can be opened for a period of time allowing an amount of growth medium 2 from the reservoir 20 to be pumped by the pump 4 into the first chamber 114A until the level of the growth medium 2 to reach the level represented by the dashed line C at which time the valve 39 can be closed and the growth medium 2 leaves the second chamber through the fluid outlet port 126C.

Similarly, in some embodiments if it is desired to further increase the level of growth medium 2 in the second chamber 114B, the valves 126A. 126C and 126D can be closed and the valve 126B can be opened while the valve 39 can be opened for a period of time allowing an additional amount of growth medium 2 from the reservoir 20 to be pumped by the pump 4 into the first chamber 114A until the level of the growth medium 2 to reach the level represented by the dashed line B at which time the valve 39 can be closed and the growth medium 2 leaves the second chamber through the fluid outlet port 126B.

Furthermore, if it is desired to even further increase the level of growth medium in the second chamber 114B, the valves, 126B, 126C and 126D, according to some embodiments, can be closed and the valve 126A opened while the valve 39 can be opened for a period of time allowing an additional amount of growth medium 2 from the reservoir 20 to be pumped by the pump 4 into the first chamber 114A until the level of the growth medium 2 reaches the level represented by the dashed line A, at which time the valve 39 can be closed and the growth medium 2 leaves the second chamber through the fluid outlet port 126A.

It will be appreciated by those skilled in the art that while the bioreactor 110 includes four fluid outlet ports 126A, 126B, 126C and 126D levels allowing four different levels, this is not obligatory of the growth medium 2 to be achieved during closed loop perfusion (recirculation) of the growth medium 2, this is by no means intended to be obligatory. Rather, in some embodiments of the bioreactors of the present applications, the number of the outlet ports (and the corresponding valves attached thereto) opening into the second chamber of the bioreactor can be varied as desired and can be smaller or larger than four (with suitable modification of the manifold 128 to accommodate the required number of valves), in such a way as to allow any desired practical number of growth medium 2 levels to be achieved in the second chamber of the bioreactor by suitable opening and closing of the valves as disclosed in detail hereinabove.

An advantage of being able to set different levels of growth medium 2 within the second chamber of the bioreactor is that it can allow the increasing or decreasing of the total volume of growth medium 2 in the second chamber 114B in order to increase (or decrease, respectively) the number of cells (or microorganisms) which can be grown within the bioreactor, if necessary. This mechanism allows culturing of cells in high density and adapting the refreshment of media and nutrients as the cell proliferate reducing or eliminating the need for passaging and dish/container replacement.

According to some embodiments, at least some of the plurality of different fluid outlet ports at the different heights and together with their corresponding valves are configured also as fluid inlets ports. In some embodiments, the plurality of different fluid outlet/inlet ports is configured to circulate out of the bioreactor a portion of the cells or microorganisms. In some embodiments, cells or microorganisms may be circulated out of the upper chamber of the bioreactor in order to process cells wherein the processed cells are then circulated back into the bioreactor (not shown). In some embodiments, cells may for example be selected by depleting or enriching of a specific cell type or genetically modified, for example but not limited to, to express a polypeptide or fragment thereof not previously expressed, or to increase or decrease expression of a polypeptide or fragment thereof. In some embodiments, processing comprising inducing cells to increase or decrease expression of a specific gene or gene variant. Methods of genetic modification and control of gene expression are well known in the art. In some embodiments, cells may be transformed (genetically modified) using any method known in the art. In some embodiments, cells may be processed wherein polypeptide expression is modified using any method known in the art. In a related embodiment, the outlet/inlet fluid ports and their corresponding valves are selected to circulate the cell mass, according to the cells mass current level (height).

It is noted that according to some embodiments, the frustoconical shape of the bioreactor 110 allows the establishment of a fluid velocity gradient along the length of the bioreactor 110 in order to gently float the cells mass 3 and keep most of the cells mass 3 suspended within a defined region of the growth medium 2 contained in the second chamber 114B to avoid cell accumulation on (and/or adhering) to the upper surface 112A of the perforated barrier 112 as well as to reduce cell loss by exiting through a fluid outlet port being used for recirculation of the growth medium 2.

According to some embodiments, the provided bioreactor comprises a vessel or at least an upper chamber with an inverted frustoconical shape configured to allow the cell (or microorganism) growing mass to float and elevate to a larger surface, due to the medium's upstream flow (against gravity direction) and the pressure equilibrium (mass gravity vs.

upstream liquid's flow). Further, due to constant volumetric-flow, a slower flow of the medium runs through the cell (or microorganism) mass at the upper and larger areas of the inverted frustoconical shape, which assist in concentrating the cells mass, and reduces shear forces applied by the medium's flow.

It is noted that like in the bioreactor 10 of FIG. 1, the vessel walls 110A are slanted at an angle with respect to a longitudinal axis 135 of the bioreactor 110 as can be seen in the part longitudinal cross section view of FIG. 2. According to some embodiments, the angle at which the vessel walls 110A are configured to be slanted with respect to the longitudinal axis 135 can be in the range of 0 to 175 degrees. However, higher or lower slant angles can also be used, depending, inter alia, on the particular application. It is noted that not all the walls of the bioreactors of the present application need be slanted and only some of the walls are configured to be slanted depending on the specific shape of the bioreactor (for example, see the bioreactor of FIG. 4I, herein after). Thus, the area of a transversal cross section of the bioreactor taken at a level represented by the dashed line A is larger than the area of a transversal cross section taken at a level D.

According to some embodiments, the transversal cross sectional area of the bioreactor 110 becomes larger as one moves upwards along the longitudinal axis 135 within the second chamber 114B results in the establishing of a fluid velocity gradient in the growth medium 2 such that the fluid velocity of the growth medium 2 gradually decreases as one moves upwards in the direction from the surface 112A towards the top part 110C.

This fluid velocity gradient assists in suspending most of the cells or microorganisms in a zone or region within the growth medium 2 of the second chamber 114B in which the force of gravity acting downwards on the cells 3 (or microorganisms) balances out the mean upward directed force exerted on the cells by the upward flowing growth medium 2 as is disclosed in detail hereinabove for the bioreactor 10. Thus, in the bioreactor 110, the controlling of the level (or height) of the growth medium 2 within the second chamber 114B together with controlling of the flow rate of the growth medium 2 (by controlling the pump flow rate) can advantageously allow finer control of the zone or region within which most of the cells are suspended within the second chamber 2. Additionally, the flow rate control allows minimizing the sheer forces introduced to the cells and maintains the ability to optimize and refresh media in correlation to the cells proliferation and density which could result in high cell density culturing.

According to some embodiments, the perforated barrier 112 of the bioreactor 110 is a flat (planar) barrier. According to some embodiments, a harvesting port 127 is configured to be used for harvesting cells from the bioreactor 110. According to some embodiments, the harvesting port 127 is shaped as a hollow member or tube that includes a first hollow part 127A and a second hollow pat 127B. The part 127A is sealingly attached to the perforated barrier 112 (in some embodiments at the center of the perforated barrier 112) and has an opening 127C which opens into the second chamber 114B at the upper surface 112A of the perforated barrier.

The second hollow part 127B is contiguous with the first hollow member 127A and bent at an angle thereto such that it passes through the vessel wall 110A of the first chamber 114A and is sealingly attached to the vessel walls 110A. The second part 127B exits the vessel walls 110A and extends outside the bioreactor 110. The second part 127B includes a valve (or a stopcock) 123 which is disposed within the portion of the second part 127B that extends outside of the bioreactor 110. When it is desired to harvest cells 3 from the bioreactor, this can be performed by concentrating the cells by reducing the level of the growth medium 2 within the second chamber 114B.

For example, the level of the growth medium 2 can be brought to the level represented by the line D, or, alternatively, to a level lower than the level D by draining additional growth medium from the first chamber through a suitable outlet port (not shown in FIG. 2) disposed in the bottom pat 110B of the bioreactor 110 (such as, for example, an outlet port similar to the outlet port 27 or ports 126A-126D illustrated in FIG. 1). After the cells 3 are concentrated, the suspension of cells 3 in the growth medium 2 can be harvested through the harvesting port 127 by opening the valve 123 and receiving the cell suspension in an appropriate collecting vessel (not shown).

According to some embodiments, the valves 126A, 126B, 126C, 126D, 39 and 123 can be manual valves (or stopcocks), but may, in accordance with some embodiments of the bioreactor 110, controllably and/or automatically operable as disclosed in detail hereinabove with respect to the valves 24, 23, 25 and 39 of FIG. 1. For example, any of the valves 126A, 126B, 126C, 126D, 39 and 123 are configured to be electrically operable solenoid valves which can be controlled to open and closed by the controller 30 of the bioreactor system 150 (it is noted that any lines connecting any of the valves 126A, 126B, 126C, 126D, 39 and 123 to the controller 30 if the valves are indeed implemented as solenoid based valves, are not shown in FIG. 2 for the sake of clarity of illustration. However, such schematic lines are shown in more detail in FIG. 5 hereinafter). According to some embodiments, the controller 20 is configured to be suitably connected through connecting wires 22B to a sensor unit 122 which is configured to include any number of sensors for sensing any chemical and/or physical properties of the growth medium 2 as disclosed in detail hereinabove for the sensor unit 22 of FIG. 1. It is noted that while the position of the end 22A of the sensor unit 22 can be fixed (since the level of the growth medium 2 in the second chamber 14B of the bioreactor 10 does not change significantly during perfusion, the sensor unit 122 is configured to be substantially longer than the sensor unit 22 and is configured to be implemented in such a way that the position of the end 122A of the sensor unit 122 can be changed, if necessary to accommodate any changes in the level of the surface of the growth medium 2 within the second chamber 114B.

For example, a substantial part of the length of the sensor unit 122 can be threaded and the opening 110F, into which the sensor unit 122 fits, can also be internally threaded to allow changing the position of the end 122A within the second chamber by suitably screwing the sensor 122 in or out as necessary. Alternatively, the surface of the sensor unit 122 can be smooth and the position of the end 122A of the sensor 122 can be varied by suitably sealingly pushing or pulling the sensor unit 122 within a suitable gasket (not shown in FIG. 2) sealingly disposed between the opening 110F and the sensor unit 122.

According to some embodiments, the oxygenating system 160 of the system 150 is configured to include an oxygen source 160A for supplying oxygen gas to the bioreactor 110, and a gas dispersing head 160 (optionally) disposed within the first chamber 114A. According to some embodiments, the oxygen source 160A is configured to be connected through a gas valve 160D to the gas dispersing head by a suitable hollow member 160C sealingly passing through the wall 110A of the bioreactor 110 such as, for example Suitable hollow flexible tubing. Alternatively, according to some embodiments, the oxygen source 160A is configured to be suitably connected through a suitable gas valve 160D to a fixed inlet formed as an integral part of the wall 110A to which the gas dispersing head can be suitably attached.

According to some embodiments, the gas valve 160D is configured to be a manually operated valve manually opened or closed by an operator. However, in some embodiments, the gas valve 160D may is configured to be an actuator controlled valve that can be suitably opened or closed by receiving suitable electrical command signals from the controller 30 (it is noted that any command lines connecting the controller 30 with the gas valve 160D are not shown in FIG. 2 for the sake of clarity of illustration. According to some embodiments, the oxygen source 160A can be a compressed oxygen tank as is known in the art, but can alternatively be any type of oxygen generator known in the art, such as but not limited to an electrolytic oxygen generator or any other source of gaseous oxygen known in the art. Alternatively, the oxygen source can be a source of any mixture of gases which contains a substantial amount of oxygen (such as, for example, air, a mixture of oxygen and nitrogen, a mixture of oxygen, nitrogen and carbon dioxide, or any other suitable mixture of gases suitable for the purpose of oxygenation of a growth medium as is known in the art.). According to some other embodiments, the oxygenation of the liquid medium is provided at the liquid's reservoir 20.

When the gas valve 160D is open, oxygen gas from the oxygen source 160A passes through the gas dispersing head 160B and is dispersed in the form of small oxygen containing bubbles that rise up within the first chamber 114A. The gas dispersing head 160B can be any type of head including perforations therein and capable of dispersing a gas passing there through a liquid (such as, for example the growth medium 2) in the form of small bubbles. For example, the gas dispersing head 160B can be a block of perforated ceramic material, a block of perforated stainless steel, a block of perforated titanium, or any other type of sterilizable dispersing head known in the art (such a gas dispersing head can be similar in construction and operation to the gas dispersing heads used to oxygenate the water in fish aquaria, as is well known in the art).

It is noted that while the oxygenating system 160 illustrated in FIG. 2 directly provides oxygen to the growth medium within the first (lower) chamber 114A of the bioreactor 110, this is in no way obligatory for practicing the bioreactor or bioreactor systems disclosed herein. For example, the oxygenating system 160 can provide oxygen to other different parts of the bioreactor system 150, such as, for example to the second chamber 114B or to the manifold 128, or to the fluid reservoir 20, or can provide oxygen to more than one part of the bioreactor system 150 (such as, for example, both to the first chamber 114A and to the fluid reservoir 20).

Alternatively, the oxygen level in the medium can be controlled by controlling the oxygen levels in the headspace between the bioreactor top 110C and the media D surface allowing oxidation by diffusion. This can be implemented by placing the oxygen dispersing head 160B in the desired part of the system or by providing several oxygen dispersing heads all suitable connected to the oxygen source 160A and disposed in any selected parts of the bioreactor system 150 for oxygenating any growth medium disposed in such parts. All such alternative oxygen supply methods are contemplated for use in some of the embodiments of the bioreactors and/or bioreactor systems as disclosed herein.

It is further noted that, since the sensors, for example the dissolved oxygen sensor, can be placed in the various inlets and outlets of the bioreactor (as mentioned above), the monitoring of the dissolved oxygen concentration within the growth medium is enabled at any time or process stage (either continuously, or at preset and/or programmable and/or predetermined time intervals). Accordingly, it enables to automate the oxygenation of the growth medium 2 in the bioreactor 110 by automatically regulating the rate of gas flow of oxygen (or oxygen containing gas mixture) through the dispersing head 160B (or heads if there is more than one such head in the system 150) to maintain a desired level of dissolved oxygen in the growth medium. According to some embodiments, the increasing of the medium's oxygen level, at the bioreactor vessel, can be provided by increasing the medium's oxygen level at the reservoir, and by increasing perfusion rate of the medium at the first chamber.

It is noted that the shape of the bioreactors of the present application are not limited to the frustoconical shape as illustrated in FIGS. 1-2. For example, the bioreactors are configured to have, inter alia, conical shape, a frustoconical shape, a tapering shape, a cylindrical shape, a polygonal prism shape, a tapering shape having an ellipsoidal transversal cross section, a tapering shape having a polygonal transversal cross section, a shape having a cylindrical part and a tapering part, and a shape having a conical or tapered part and a hemispherical part. However, other different bioreactor shapes can also be implemented in accordance with some embodiments of the bioreactor, depending, inter alia, on the specific application and on manufacturing considerations.

Several possible exemplary shapes of the bioreactors are schematically illustrated in FIG. 3 and FIGS. 4A-4I. Reference is now made to FIG. 3, which is a schematic part cross-sectional diagram illustrating a bioreactor system including a bioreactor having a cylindrical shape including a perforated barrier, in accordance with another embodiment of the bioreactors of the present application.

According to some embodiments, the bioreactor system 250 includes a bioreactor 210, the controller 30 as disclosed in detail hereinabove, the pump 4 as disclosed in detail hereinabove and the fluid reservoir 20 as disclosed in detail hereinabove. According to some embodiments, the bioreactor system 250 also includes the oxygenating system 160 as disclosed in detail hereinabove. The bioreactor 210 can be made from any of the materials disclosed in detail hereinabove for the bioreactors 10 and 110. The bioreactor 210 has vessel walls 210A, a bottom part 210B and a bioreactor top part 210C. The top part 210C may have an opening 210G therein and a self-sealing gasket 211 can be disposed within the opening for sealing the opening. The self-sealing gasket 211 can be sealably penetrated by a needle (not shown in FIG. 3) for introducing a suspension of cells or microorganisms in a growth medium, or any other fluid or solution containing any substance or additive into the bioreactor 210, as disclosed in detail hereinabove.

It is noted that the cells or microorganisms can also be introduced into the second chamber of the bioreactor through any suitable one way valve (not shown in FIG. 3) disposed in the walls or top of the bioreactor such that the one way valve allows the injecting of a cell suspension or a microorganism suspension there through and into the second chamber of the bioreactor without compromising the sterility of the bioreactor.

In accordance with one embodiment of the bioreactors, the one way valve can be a luer-lock like valve which can be shaped to accept the end of a standard syringe containing the cell or microorganism suspension. The use of such a one way valve can be advantageous because the orifice of the valve can be made sufficiently large to reduce the shearing forces affecting the cells when the suspension is injected into the bioreactor. It is noted that any of the bioreactors of the present application are configured to have any combination of such opening(s), self-sealing gasket(s) and one way valve(s).

According to some embodiments, the vessel walls 210A are configured to have an opening 210F for sealingly inserting there through a threaded sensor unit 222. The sensor unit 222 is configured to include any number of sensors (not shown individually in FIG. 3 for the sake of clarity of illustration) attached to or included in sensor unit 222 for sensing any desired chemical or physical property of the growth medium 2 as disclosed in detail hereinabove with respect to the sensor unit 122 in FIG. 2.

According to some embodiments, a perforated barrier 212 is sealingly attached to the vessel wall 210A of the bioreactor 210 such that the perforated barrier 212 divides the internal volume of the bioreactor 210 into a first (lower) chamber 214A and a second (upper) chamber 214B, as disclosed in detail hereinabove for the bioreactor 10 and the perforated barrier 12 of the bioreactor system 50 of FIG. 1. The perforated barrier 212 can be made from similar material(s) and can have similar perforation mean sizes as disclosed in detail hereinabove for the perforated barriers, for example 12 of FIG. 1. However, while the bioreactor 10 (of FIG. 1) has a single fluid outlet port 26 in the second chamber 14B, the bioreactor 210 can comprise several different fluid outlet ports (not shown) in the second chamber 214B, wherein the outlet ports comprise an individual outlet and valve (not shown).

According to some embodiments, the valves are fluidically connected to a common fluid manifold 280A which is fluidically connected to the pump 4. The arrangement of the four valves at different positions, as illustrated in FIG. 2, allows the level of the growth medium 2 to be selected from four different levels.

According to some embodiments, the number of the outlet ports (and the corresponding valves attached thereto) opening into the second chamber of the bioreactor can be varied (the number of outlet ports can be smaller or larger than 4, with suitable modification of the manifold 280 to accommodate the required number of valves) in such a way as to allow any desired practical number of growth medium 2 levels to be achieved in the second chamber of the bioreactor by suitable opening and closing of the valves as disclosed in detail hereinabove.

According to some embodiments, the oxygenating system 160 of the system 250 includes an oxygen source 160A for supplying oxygen gas to the bioreactor 110, and a gas dispersing head 160 (optionally) disposed within the first chamber 214A. The oxygen source 160A is configured to be connected through a gas valve 160D to the gas dispersing head by a suitable hollow member 160C sealingly passing through the wall 210A of the bioreactor 110 such as, for example Suitable hollow flexible tubing. Alternatively, the oxygen source 160A is configured to be suitably connected through a suitable gas valve 160D to a fixed inlet formed as an integral part of the wall 210A to which the gas dispersing head can be suitably attached. Additionally, the concentration of oxygen can also be controlled by controlling the oxygen concentration in the headspace between the top part 210C and liquid level D allowing oxygenation of the growth medium 2 via diffusion. In some embodiments, the pH may be adjusted. For example but not limited to controlling $CO_2$ concentration, the pH can be controlled by controlling the $CO_2$ concentration in the headspace via diffusion.

According to some embodiments, the gas valve 160D is configured to be a manually operated valve manually opened or closed by an operator. However, in some embodiments, the gas valve 160D is configured to be an actuator controlled valve that can be suitably opened or closed by receiving suitable electrical command signals from the controller 30 (it is noted that any command lines connecting the controller 30 with the gas valve 160D are not shown in FIG. 3 for the sake of clarity of illustration. According to some embodiments, the oxygen source 160A can be a compressed oxygen tank, as is known in the art, but can alternatively be any type of oxygen generator known in the art, such as but not limited to an electrolytic oxygen generator or any other source of gaseous oxygen known in the art.

Alternatively, the oxygen source can be a source of any mixture of gases which contains a substantial amount of oxygen (such as, for example, air, a mixture of oxygen and nitrogen, a mixture of oxygen, nitrogen and carbon dioxide, or any other suitable mixture of gases suitable for the purpose of oxygenation of a growth medium as is known in the art.) When the gas valve 160D is open, oxygen gas from the oxygen source 160A passes through the gas dispersing head 160B and is dispersed in the form of small oxygen containing bubbles that rise up within the first chamber 214A. The gas dispersing head 160B can be any type of head including perforations therein and capable of dispersing a gas passing through a liquid (such as, for example the growth medium 2) in the form of small bubbles.

For example, the gas dispersing head 160B can be a block of perforated ceramic material, a block of perforated stainless steel, a block of perforated titanium, or any other type of sterilizable dispersing head known in the art (such a gas dispersing head can be similar in construction and operation to the gas dispersing heads used to oxygenate the water in fish aquaria, as is well known in the art).

Reference is now made to FIGS. 4A-4I which are schematic cross-sectional diagrams illustrating several exemplary shapes of bioreactors including a perforated barrier in accordance with several embodiments of the bioreactors of the present application. It is noted that, for the sake of clarity of illustration, the schematic drawings of Mgs, 4A-4I illustrate only the general shape of the walls of the bioreactors and the perforated barrier included therein and do not show any details of any additional components of the bioreactors or bioreactor systems (such as, for example, various openings in the walls of the bioreactors, sensor units, fluid inlet ports, fluid outlet ports, draining ports, harvesting ports, heating units, cooling/heating units, fluid impellers, gas dispersing heads, valves, pumps, controllers, self-sealable gaskets, fluid manifolds or any other components) which are not important to understanding the shape of the bioreactors. It will be appreciated by those skilled in the art that any such components not shown in FIGS. 4A-4I may be included in any non mutually exclusive combinations and/or permutations in any of the bioreactors schematically illustrated in FIGS. 4A-4I, as is disclosed herein in detail herein and illustrated in the drawing figures.

It is further noted that while the perforated barriers illustrated in FIGS. 4A-4I are illustrated as a flat fixed perforated barriers, this is shown by way of example only and it is contemplated that any of the bioreactors having shapes as disclosed in FIGS. 4A-4I may also be implemented as any of the types of perforated barriers disclosed in the present application (including any of the flat or non-flat, fixed and movable perforated barriers, buckling perforated barriers and all other perforated barrier forms disclosed in the present application).

Turning to FIG. 4A, the bioreactor 300 includes the perforated barrier 12 as disclosed hereinabove which divides the bioreactor 300 into a first chamber 304A shaped as a cylindrical part of the bioreactor 300 and a second chamber 304B shaped as a frustoconical part of the bioreactor 300. Thus the bioreactor 300 has a shape that has a cylindrical part and a frustoconical part.

Turning to FIG. 4B, the bioreactor 310 includes the perforated barrier 12 as disclosed hereinabove which divides the bioreactor 310 into a first chamber 314A shaped as a cylindrical part of the bioreactor 300 and a second chamber 314B shaped as a tapering part of the bioreactor 300. Thus, the bioreactor 300 has a shape that has a cylindrical part and a tapering part. The tapering walls 308 of the second chamber 314B have a convex outer surface 308A.

Turning to FIG. 4C, the bioreactor 320 includes the perforated barrier 12 as disclosed hereinabove which divides the bioreactor 320 into a first chamber 324A shaped as a cylindrical part of the bioreactor 320 and a second chamber 324B shaped as a tapering part of the bioreactor 320. The bioreactor 320 has a shape that has a cylindrical part and a tapering part. The tapering walls 328 of the second chamber 324B have a concave outer surface 328A.

Turning to FIG. 4D, the bioreactor 330 includes the perforated barrier 12 as disclosed hereinabove which divides the bioreactor 330 into a first chamber 334A shaped as a tapering part of the bioreactor 330 and a second chamber 334B shaped as a tapering part of the bioreactor 330. The bioreactor 330 has a tapering shape. The tapering walls 338 of the bioreactor 330 have a convex outer surface 338A.

Turning to FIG. 4E, the bioreactor 340 includes the perforated barrier 12 as disclosed hereinabove which divides the bioreactor 340 into a first chamber 344A shaped as a tapering part of the bioreactor 340 and a second chamber 344B shaped as a tapering part of the bioreactor 300. The bioreactor 340 has a tapering shape. The tapering walls 348 of the bioreactor 340 have a convex outer surface 348A.

Turning to FIG. 4F, the bioreactor 350 includes the perforated barrier 12 as disclosed hereinabove which divides the bioreactor 350 into a first chamber 354A shaped as a conical of part of the bioreactor 350 and a second chamber 354B shaped as a frustoconical part of the bioreactor 300. The bioreactor 350 has a conical shape.

Turning to FIG. 4G, the bioreactor 360 includes the perforated barrier 12 as disclosed hereinabove which divides the bioreactor 360 into a first chamber 364A shaped as a cylindrical part of the bioreactor 360 and a second chamber 364B shaped as a cylindrical part of the bioreactor 360. The bioreactor 360 has a cylindrical shape.

Turning to FIG. 4H, the bioreactor 370 includes the perforated barrier 12 as disclosed hereinabove which divides the bioreactor 370 into a first chamber 374A shaped as a hemispherical part of the bioreactor 370 and a second chamber 374B shaped as a frustoconical part of the bioreactor 370. The bioreactor 370 has a shape similar to a chalice.

Turning to FIG. 4I, the bioreactor 380 includes the perforated barrier 12 as disclosed hereinabove which divides the bioreactor 380 into a first chamber 384A and a second chamber 384B. The bioreactor 380 includes a vertical wall portion 380H that is orthogonal to the bottom part 380B of the bioreactor 380 (the wall portion 380H forms an angle of 90 degrees with the bottom part 380B) and a slanted wall portion 380E that is slanted at an angle $\alpha1$ relative to the wall portion 380H (the dashed line 385 is parallel to the vertical wall portion 380H). Typically the angle $\alpha1<90°$ and in some embodiments but not obligatorily $\alpha1<45°$.

Reference is now made to FIG. 4, which is a top view of the bioreactor 380 of FIG. 4I. The top part 380C of the bioreactor 380 is shaped such that it has a semi-circular portion 380E, two straight portions 380F and 380G and a straight portion 380H. The bottom part 380B of the bioreactor 380 (schematically illustrated by the dashed line 380B in FIG. 4J) can have a shape or contour similar to the shape or contour of the top part but has a smaller cross-sectional area than the cross-sectional area of the top part 380C due to the slanting of the wall portion 380E.

It is noted that while the shape of the top part 38C of the bioreactor 380 is as disclosed hereinabove with respect to FIG. 4Q, this is not obligatory and other different shapes of the top part 380C and the bottom part 380B can be used in some embodiment of the bioreactors having a slanted wall portion or part. In some embodiments of the bioreactors having a slanted wall portion and a non-slanted wall portion, the top and/or bottom parts of the bioreactor can have any other desired shape including but not limited to, a semi-elliptical shape, a semi-circular shape, a rectangular shape, a square shape, a trapazoidal shape, a polygonal shape, or any other suitable regular or irregular shape.

It is noted that while in several of the embodiments of the bioreactors disclosed hereinabove transversal cross sections of the bioreactor can be circular, in other embodiment of the bioreactors of the present application, transversal cross sections of the bioreactor can have other shapes, including, but not limited to an elliptical shape, a polygonal shape, a regular polygonal shape, or any other suitable shape.

It is further noted that in some of the bioreactors disclosed herein different transversal cross sections taken at different positions along a longitudinal axis of the bioreactor can have different shapes. For example, returning to FIG. 4C, while the transversal cross section taken along the lines I-I and II-II (which are both orthogonal to the longitudinal axis 335) can both be circular in shape, in accordance with another embodiment of the bioreactor, the transversal cross section taken along the line I-I can be circular in shape, and the transversal cross section taken along the line II-II can be elliptical in shape.

Furthermore, in accordance with some embodiments of the bioreactor, the shape of the bioreactor can be a conical shape, a frustoconical shape, a tapering shape, a cylindrical shape, a polygonal prism shape, a tapering shape having an ellipsoidal transversal cross section, a tapering shape having a polygonal transversal cross section, a shape having a cylindrical part and a tapering part, and a shape having a conical or tapered part and a hemispherical part.

Figure 5:
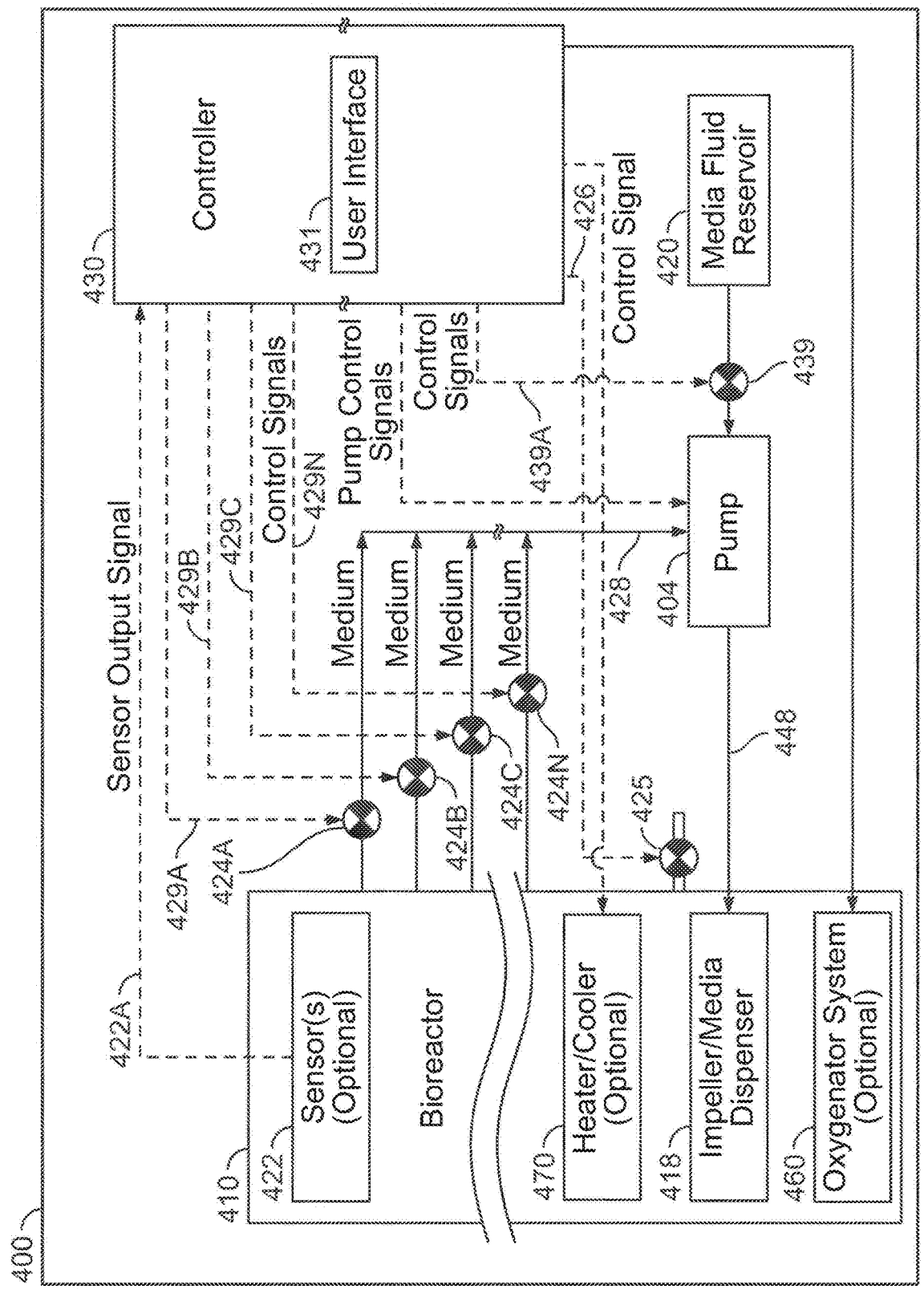
FIG. 5 is a schematic block diagram illustrating the components of a bioreactor system (400), in accordance with some embodiments of the bioreactor systems disclosed herein.

Reference is now made to FIG. 5 which is a schematic block diagram illustrating the components of a bioreactor system, in accordance with some embodiments of the bioreactor systems of the present application. The bioreactor system 400 includes a bioreactor 410, a pump 404, the bioreactor system can also include N+1 controllable valves 424A-424N (wherein N is an integer number) and another controllable valves 439. The bioreactor system can also include an (optional) controller 430, an (optional) fluid reservoir 420, an (optional) fluid impeller 418 an (optional) oxygenating system 460 and an (optional) heater/cooler unit 470. In some embodiments, a bioreactor system disclosed herein further comprises a controller. In some embodiments, a bioreactor system further comprises a fluid reserve. In some embodiments, a bioreactor system further comprises a fluid impeller. In some embodiments, a bioreactor system further comprises an oxygenating system. In some embodiments, a bioreactor system further comprises a heater unit. In some embodiments, heating on the liquid medium can be provided via a heating jacket or any provided bioreactor surrounding environment (not shown). In some embodiments, a bioreactor system further comprises a cooler unit. In some embodiments, a bioreactor system further comprises a heater unit and a cooler unit. According to some embodiments the liquid's temperature can be controlled (heated/cooled to a desired temperature) at the liquid's reservoir.

In some embodiments, a bioreactor system comprises a control signal to an outlet valve (426). In some embodiments, a bioreactor system comprises a control signal (439A) for a pump.

According to some embodiments, the bioreactor 410 can be any of the bioreactors that have multiple fluid outlet ports (as disclosed in the present application and illustrated in the drawing figures) which include a first (lower) chamber and a second (upper) chamber (the first and second chambers are not shown in detail in the schematic block diagram of FIG. 5, but can be seen as illustrated, for example, in FIG. 2). Each of the multiple fluid outlet ports opening into the second chamber (not shown in the schematic diagram of FIG. 5 for the sake of clarity) is fluidically connectable to a fluid manifold 428 through one of the respective N valves 424A-424N.

According to some embodiments, the fluid manifold 428 is configured to feed the growth medium collected from the second chamber of the bioreactor 410 to the pump 404 which is configured to pump the growth medium back into the first chamber of the bioreactor 410 through the fluid inlet port 448 which opens into the first chamber of the bioreactor 410. The fluid input port 448 is configured to (optionally) feed the growth medium to the (optional) fluid impeller 418 as disclosed in detail hereinabove with respect to FIG. 2. The sensor unit 422 can be implemented as disclosed hereinabove with respect to any of the sensor units 22, 122 and 222 (of FIGS. 1, 2 and 3, respectively).

According to some embodiments, the fluid reservoir 420 can be a fluid reservoir external to the bioreactor 410, as disclosed hereinabove, and is configured to be fluidically and controllably coupled to the pump 404 through the valve 439. Each of the N valves 404A-404N is suitably connected to the controller 430 by a respective communication lines 429A-429N to receive control signals from the controller for opening or closing any of the valves 424A-424N. The valve 439 is connected to the controller 430 by a suitable communication line for receiving control signals there from to open or close the valve 439 for allowing growth medium to flow from the reservoir 420 into the pump 404 and there from into the bioreactor 410 as disclosed in detail hereinabove for the valve 39 (of FIG. 1).

According to some embodiments, the pump 404 is configured to be suitably connected to the controller 430 by a suitable communication line for controlling the operation of the pump 404. For example, such control signals can turn the pump on or off and can also control the rate of flow of growth medium through the pump 404 (or the rate of pumping of the growth medium by the pump 404.

According to some embodiments, the (optional) heater/cooler 470 is configured to be disposed in the bioreactor 410 (in some embodiments within the first chamber thereof) to heat or cool the growth medium within the bioreactor 410 to maintain a desired temperature of the growth medium. Optionally, a water jacket (not shown) or blanket (not shown) or any other controlled temperature environment can be used for temperature control of the bioreactor.

According to some embodiments, if the sensor unit 422 includes a temperature sensor, signals representing the sensed temperature can be sent from the temperature sensor to the controller 430 through a communication line(s) 422A. The controller 430 is configured to process such signals and send appropriate signals to the heater/cooler 470 for maintaining a desired temperature, or a set temperature or a preset temperature within the bioreactor as is well known in the art of temperature control. Any other sensors included within the sensor unit 422 are configured to (optionally) send through the communication line(s) 422A sensor signals representing any sensed physical or chemical parameter of the growth medium in the bioreactor 410, as disclosed in detail hereinabove.

According to some embodiments, the controller 430 is configured to process any such sensor signals to determine the status of the growth medium and can also use the processed either display status data or about any monitored or sensed physical or chemical parameters to an operator or user of the bioreactor system 400 by an (optional) display unit (not shown in detail in FIG. 5) included in an (optional) user interface 431 included in the controller 430, as is disclosed hereinabove in detail.

For example, in a case in which the sensor unit includes a dissolved oxygen sensor for sensing the amount of oxygen dissolved in the growth medium within the bioreactor 430, the sensor signals can be processed by the controller 430 and if the concentration of dissolved oxygen is different than a desired set, preset, or predetermined) value, the controller 430 is configured to send control signals to the oxygenating system 460 for stopping or starting the introducing of oxygen containing gas into the growth medium within the bioreactor 430 (or within the fluid reservoir 420, depending on the specific implementation of the bioreactor system 400 to suitably adjust the dissolved oxygen level to the desired level.

It is noted that as disclosed in detail hereinabove with respect to the controller 30 (of FIG. 1), the controller unit 430 is configured to include any type of suitable processor (digital and/or analog) which can be operated by suitable software to automatically or semi-automatically control the operation of the bioreactor 430 or at least some of the operational functions thereof. For example, while the determining of the growth medium level and rate of flow within the second chamber of the bioreactor 410 can be set manually by an operator by using the user interface 431, the regulation of the bioreactor's temperature and/or dissolved oxygen concentration within the growth medium can be automatically controlled by suitable software operating on the controller 430. Similarly, the addition of amounts of fresh growth medium from the reservoir 420 can be fully automated by periodically draining an amount of the growth medium from the first chamber through a draining port 427 by turning the 404 off and opening a draining valve 425, and then closing the draining valve 425, opening the valve 439 and turning the pump 404 on to allow an amount of fresh growth medium to be pumped into the first chamber and then closing the valve 439 to restart the recirculation of the growth medium through the bioreactor 410. A similar method can be used in the reservoir 430 resulting in media refreshment.

When the cells or microorganisms grown within the bioreactor need to be harvested, the harvesting can be performed is several different ways in accordance with the specific structure of the bioreactor.

In some embodiments of the bioreactor (such as, for example in the bioreactor of FIG. 1), the perforated barrier is fixed and immovably attached to the walls of the bioreactor and the harvesting. The harvesting of cells in such a bioreactor, can be performed by using one or more harvesting ports disposed in the vessel walls of the bioreactor and opening into the second chamber in the vicinity of the upper surface of the perforated barrier (such as, for example, the single harvesting port 21 of the bioreactor 10 which opens into the second chamber 14B in the vicinity of the surface 12A of the perforated barrier 12 of FIG. 1. However, since the flat surface 12A of the bioreactor 10 is horizontal during harvesting, the harvesting may be somewhat hampered as some of the cells 3 may not reach the opening of the harvesting port 21.

Reference is now made to FIGS. 6A-6B which are schematic part cross-sectional diagrams illustrating two possible positional states of a tiltable bioreactor, in accordance with some embodiments of the bioreactors of the present application.

It is noted that the bioreactor 510 of FIGS. 6A-6B is only schematically illustrated in outline and only the components necessary for understanding the harvesting operation thereof are shown in detail. Other components of the bioreactor 510 not necessary for understanding of the tilting action and the cell harvesting are not shown in FIGS. 6A-6B for the sake of clarity of illustration and can be implemented as disclosed in detail for the bioreactors of FIG. 1-5 or any other bioreactors disclosed herein. In the tiltable bioreactor 510 of FIG. 6A, the bioreactor includes vessel walls 510A, top part 510C and bottom part 510B. The space within the bioreactor 510 is divided into a first chamber 514A and a second chamber 514B by a perforated barrier 512. Any other components of the bioreactor 510 not shown in detail in FIGS. 6A-D can be as disclosed in detail hereinabove with respect to the bioreactor 10 of FIG. 1. In FIG. 6A, the bioreactor 510 is in a vertical state in which the longitudinal axis 535 of the bioreactor 510 is vertical (in FIG. 6A this is represented by the longitudinal axis 535 being aligned along the vertical axis V). The bioreactor 510 includes a harvesting port 521 and a valve 523.

In FIG. 6A, the valve 523 is shown in the closed state and the bioreactor 510 is shown to contain a small amount of growth medium 2 in which the cells 3 to be harvested are suspended after most (but not all) of the growth medium 2 has been drained from the bioreactor 510 through an outlet port 527 opening into the first chamber 514A by opening the valve 525. During draining, according to some embodiments, some of the growth medium 2 held in the second chamber 514B passes downstream through the perforations of the perforated barrier and into the first chamber 514A and exits from the outlet port 527 but the cells 3 are retained in the second chamber 514B as they cannot pass through the perforations of the perforated barrier. According to some embodiments, the draining can also be provided via a deep tube (not shown) that can be inserted to the upper chamber via for example one of the outlet ports 126A-126D (shown in FIG. 2), as long as the deep tube is positioned above cell mass concentration. According to some embodiments, the draining can also be provided by opening the valve of one of the outlet ports 126A-126D (shown in FIG. 2), as long as the outlet port is located above cell mass concentration. This results in concentrating the cells in the second chamber 514B due to the reduction of the amount of growth medium 2 remaining in the second chamber. When the level of the growth medium 2 in the second chamber 514B has been sufficiently reduced, the valve 525 can be closed.

According to some embodiments, in order to perform the cell harvesting, the bioreactor 510 is now tilted as illustrated in FIG. 6B, which illustrates the bioreactor 510 in a tilted state. In the tilted state, the longitudinal axis 535 of the bioreactor 510 is tilted at an angle $\alpha$ to the vertical direction (represented in FIG. 6B by the vertical dashed line V). The angle $\alpha$ can be any convenient angle in the range $0<\alpha<90$ degrees. After the bioreactor 510 is tilted (for example at an angle $\alpha=45$ degrees), the suspended cells 3 can be harvested into a suitable collecting vessel such as a test tube 511 by opening the valve 523 as illustrated in FIG. 6B. The advantage of such tiltable bioreactors is that during harvesting, the yield of collected cells can be higher as compared to the yield of harvesting performed in non-tiltable bioreactors such as the bioreactor 10 of FIG. 1. As FIGS. 6B, 6C, and 6D are embodiments of the bioreactor 510 of FIG. 6A, the elements in FIGS. 6B, 6C, and 6D that are identified above for FIG. 6A have the same meaning and qualities as these elements in FIG. 6A.

According to some embodiments, the tilting action of the bioreactor 510 (or of any other type of tiltable bioreactor implemented as disclosed in the present application) can be performed by any mechanical means known in the art, such as, but not limited to, by tilting the bioreactor within any mechanical support structure (not shown) holding the bioreactor 510. Additionally, in accordance with some additional embodiments of the bioreactor, the bioreactor 510 is configured to be tiltably supported within a fork-like gantry (not shown) having two opposing arms tiltably holding a bracket within which the bioreactor 510 can be supported. Such mechanical structures for tiltably holding a vessel such that it can be vertically aligned or tilted at any desired angle to the vertical are well known in the art, and are therefore not described in detail hereinafter.

Reference is now made to FIGS. 6C and 6D which are schematic part cross-sectional views illustrating a bioreactor having a fixed slanted perforated barrier, in accordance with some embodiments of the bioreactors of the present application;

It is noted that the bioreactor 550 of FIGS. 6C-6D is only schematically illustrated in outline and only the components necessary for understanding the harvesting operation thereof are shown in detail. Other components of the bioreactor 550 that are not necessary for understanding of the cell harvesting method are not shown in FIGS. 6C-6D for the sake of clarity of illustration and can be implemented as disclosed in detail for the bioreactors of FIGS. 1-2 and 5 or any other bioreactors disclosed herein.

The bioreactor 550 of FIG. 6C includes vessel walls 550A, a top part 550C and a bottom part 550B. The space within the bioreactor 550 is divided into a first chamber 520A and a second chamber 520B by a perforated barrier 512. Any other components of the bioreactor 550 not shown in detail in FIGS. 6C and 6D are disclosed in detail hereinabove with respect to the bioreactor 10 of FIG. 1. The perforated barrier 522 is sealingly and fixedly attached to the vessel walls 550A and is slanted at an angle $\beta$ relative to the horizontal plane H of the bioreactor 550 (the horizontal plane is schematically represented by the dashed line H in FIGS. 6C and 6D). The angle Q can be any angle in the range $0.2<\beta<45$ degrees, but other angles smaller or larger than this range can be used, depending, inter alia, upon the application. In typical applications the angle Q can be in the range of $0.2<\beta<15$ degrees.

The bioreactor 550 includes a harvesting port 531 having a valve 533. The valve 533 of the harvesting port 531 is illustrated in FIG. 6C in a closed state and the bioreactor 550 is shown to contain an amount of growth medium 2 including the cells 3 suspended in the growth medium 2.

Turning now to FIG. 6D, when the cells 3 need to be harvested, most (but not all) of the growth medium 2 is drained from the bioreactor 550 through an outlet port 527 opening into the first chamber 520A by opening the valve 525 of the outlet port 527.

During draining, most of the growth medium 2 (or a washing buffer used to wash the cells 3) flows into the first chamber 520A by passing through the perforations in the perforated barrier 522 and exits from the outlet port 527 but the cells 3 are retained in the second chamber 520B as they cannot pass through the perforations in the perforated barrier. This results in concentrating the cells 3 in the second chamber 520B due to the reduction of the amount of growth medium 2 remaining in the second chamber 520B. When the level of the growth medium 2 in the second chamber 520B has been sufficiently reduced, the valve 525 can be closed.

Turning to FIG. 6D, the bioreactor 550 is illustrated with the second chamber 520B containing the cells 3 concentrated in the small amount of the growth medium 2 remaining within the second chamber 520B after most of the growth medium 2 was drained from the second chamber 520B; for example, by opening the valve 525 of the outlet port until the desired amount of growth medium is drained from the bioreactor 550 and then closing the valve 525, and/or via the deep tube (as mentioned above) and/or one of the second chamber's outlet ports (as mentioned above). The harvesting of the cells can be performed by opening the valve 533 of the harvesting port 531 and connecting a collecting vessel 511 to the end of the harvesting port 531.

Figure 8:
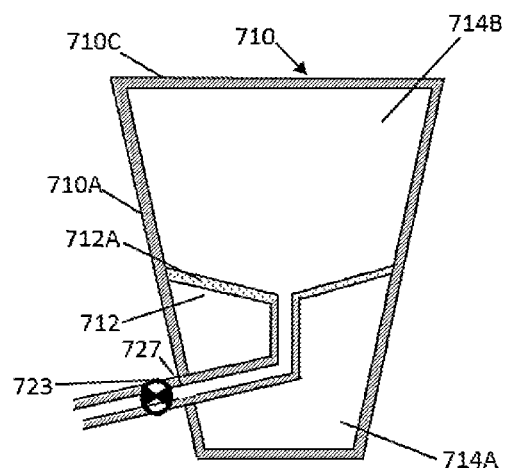
Figure 9:
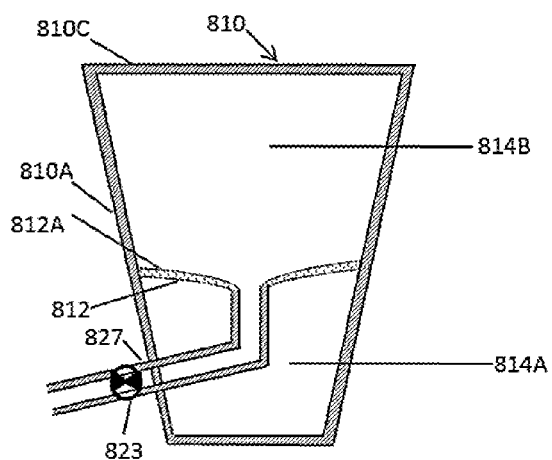
Figure 10A:
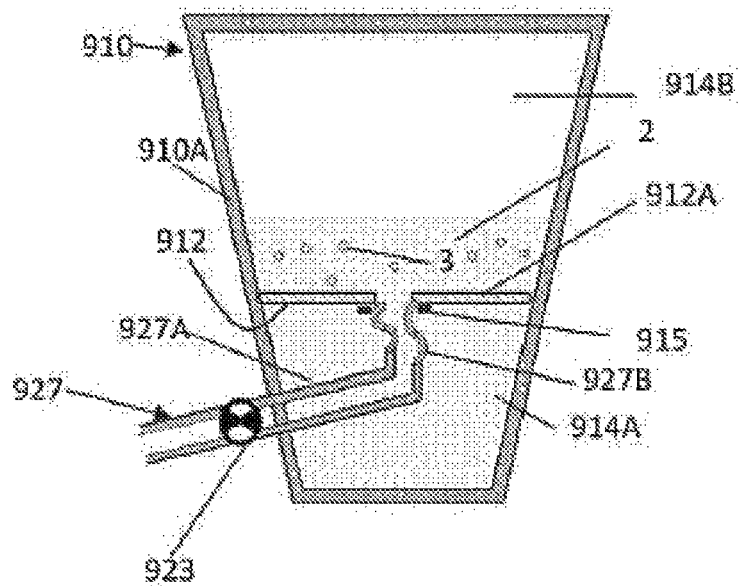
FIGS. 10A and 10B are schematic part cross-sectional views illustrating two embodiments of different states of a bioreactor (910) including a deformable perforated barrier (912)
Figure 10B:
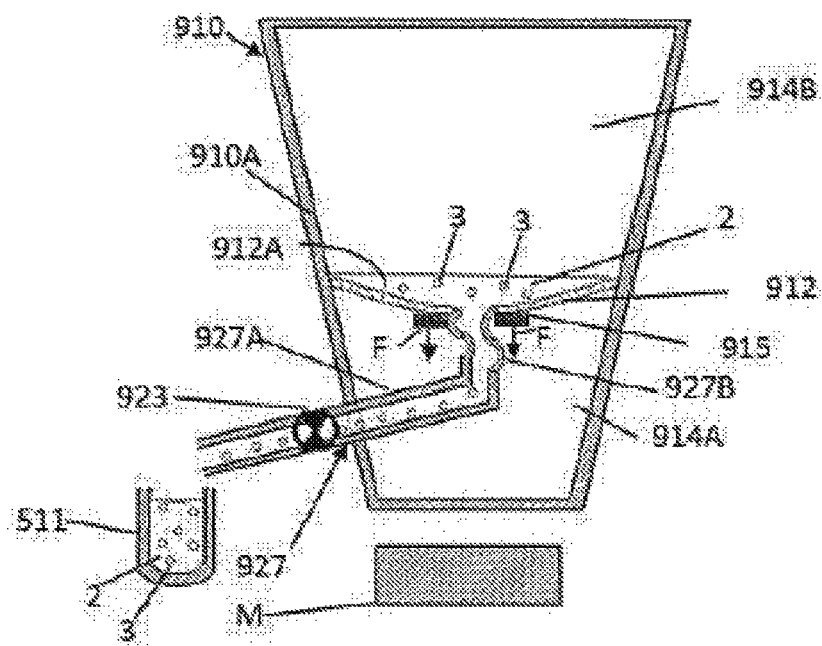

Reference is now made to FIGS. 7-9, which are schematic, part cross-sectional diagrams illustrating three different embodiments of bioreactors including three different types of non-planar (not flat) perforated barriers, in accordance with some embodiments of the bioreactors of the present application. It is noted that for the sake of clarity of illustration, the schematic drawings of FIGS. 7-9 illustrate only the general shape of the walls of the bioreactors and the shape of the perforated barrier included therein and of the harvesting port associated with the perforated barrier and do not show any details of any additional components of the bioreactors or bioreactor systems (such as, for example, various openings in the walls of the bioreactors, sensor units, fluid inlet ports, fluid outlet ports, draining ports, harvesting ports, heating units, cooling units, fluid impellers, gas dispersing heads, valves, controllers, self-sealable gaskets, fluid manifolds or any other components) which are not important to understanding the shape of the perforated barriers shown of the bioreactors. It will be appreciated by those skilled in the art that any such components which are not shown in FIGS. 7-9, can be included in any non-mutually exclusive combinations and/or permutations in any of the bioreactors schematically illustrated in FIGS. 7-9, as is disclosed herein in detail herein and as illustrated in the drawing figures.

Turning to FIG. 7, the bioreactor 610 has vessel walls 610A, a curved perforated barrier 612 is fixedly (non-movably) and sealingly attached to the vessel walls 610A, dividing the space within the bioreactor 610 into a first chamber 614A and a second chamber 614B. The bioreactor 610 further comprises a harvesting port 627 which is a hollow member that includes a valve 623. The harvesting port 627 is similar in structure to the harvesting port 127 of FIG. 2. The harvesting port 627 is sealingly attached to the curved perforated barrier 612 and opens at the surface 612A into the second chamber 614B.

As disclosed in detail hereinabove for the harvesting port 127 (of FIG. 2), the harvesting port 627 scalingly passes through the vessel walls 610A to exit the bioreactor 610. The upper surface 612A of the curved perforated barrier 612 facing the top part 610C of the bioreactor 610 is concave, which can advantageously increase the yield of harvested cells as compared to the yield of harvested cells in a bioreactor having a fixed (non-movable) flat (planar) perforated barrier (such as, for example, the bioreactor 110 of FIG. 2).

Turning to FIG. 8, the bioreactor 710 has vessel walls 710A, a conical perforated barrier 712 is fixedly (non-movably) and sealingly attached to the vessel walls 710A, dividing the space within the bioreactor 710 into a first chamber 714A and a second chamber 714B. The bioreactor 710 further comprises a harvesting port 727 which is a hollow member that includes a valve 723. The harvesting port 727 is similar in structure to the harvesting port 127 of FIG. 2. H represents the horizontal plane H of the bioreactor (710).

According to some embodiments, the harvesting port 727 is sealingly attached to the conical perforated barrier 712 and opens at the surface 712A into the second chamber 714B. As disclosed in detail hereinabove for the harvesting port 127 (of FIG. 2), the harvesting port 727 sealingly passes through the vessel walls 710A to exit the bioreactor 710. The upper surface 712A of the conical perforated barrier 712 facing the top part 710C of the bioreactor 710 is a conical surface, which can advantageously increase the yield of harvested cells as compared to the yield of harvested cells in a bioreactor having a fixed (non-movable) flat (planar) perforated barrier (such as, for example, the bioreactor 110 of FIG. 2).

Turning to FIG. 9, the bioreactor 810 has vessel walls 810A, a tapering perforated barrier 812 is fixedly (non-movably) and sealingly attached to the vessel walls 810A, dividing the space within the bioreactor 810 into a first chamber 814A and a second chamber 814B. The bioreactor 810 further comprises a harvesting port 827 which is a hollow member that includes a valve 823. The harvesting port 827 is similar in structure to the harvesting port 127 of FIG. 2. The harvesting port 827 is sealingly attached to the tapering perforated barrier 812 and opens at the surface 812A into the second chamber 814B.

As disclosed in detail hereinabove for the harvesting port 127 (of FIG. 2), the harvesting port 827 scalingly passes through the vessel walls 810A to exit the bioreactor 810. The upper surface 812A of the tapering perforated barrier 812 facing the top part 810C of the bioreactor 810 is a tapering surface, which can advantageously increase the yield of harvested cells as compared to the yield of harvested cells in a bioreactor having a fixed (non-movable) flat (planar) perforated barrier (such as, for example, the bioreactor 110 of FIG. 2).

It is noted that while all the bioreactors disclosed hereinabove and illustrated in FIGS. 1-3, 4A-4I, 6A-6B and 7-9 include fixed non-movable perforated barriers, this is not obligatory to practicing the using the bioreactors or systems thereof disclosed herein, and in accordance with some embodiments, the bioreactors are configured to include movable (non-fixed) perforated barriers or tiltable perforated barriers.

Reference is now made to FIGS. 1A-10B, 11A-11B and 12A-12B, which illustrated some embodiments of reactors having movable and/or tiltable perforated barriers. FIGS. 1A-10B are schematic part cross-sectional diagrams illustrating two different states of a bioreactor including a deformable perforated barrier, in accordance with some embodiments of the bioreactors of the present application.

Figure 11A:
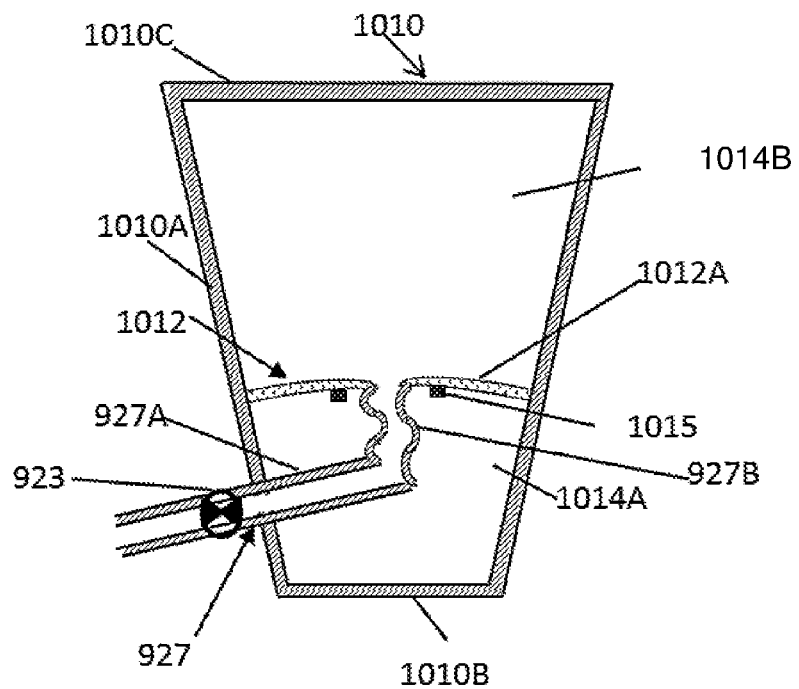
FIGS. 11A and 11B are schematic part cross-sectional views illustrating two embodiments of different states of a bioreactor (1010) including a buckling perforated barrier (1012)
Figure 11B:
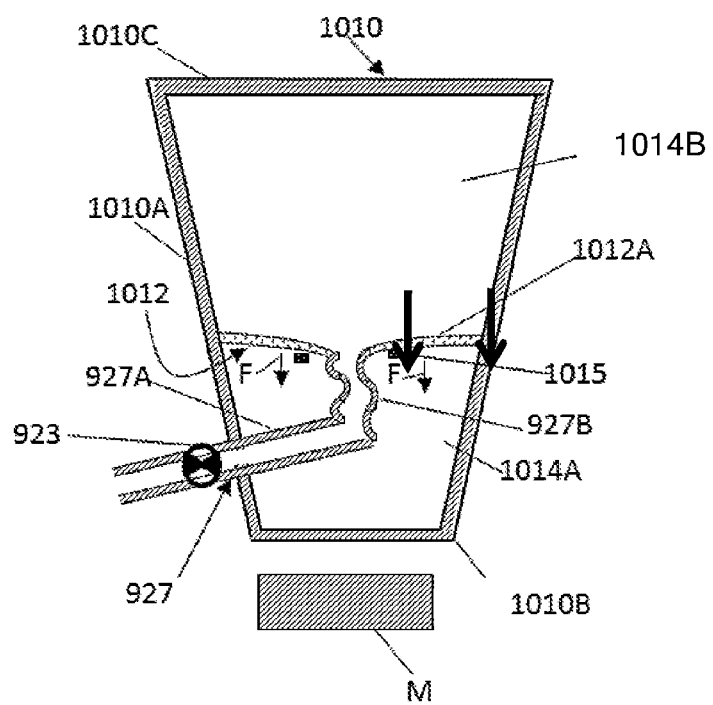
Figure 12A:
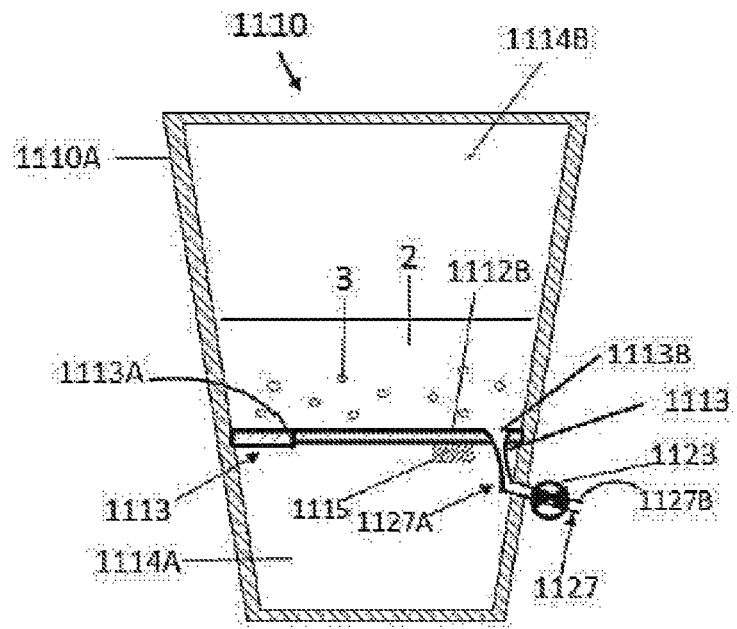
FIGS. 12A and 12B are schematic part cross-sectional views illustrating two embodiments of different operational states of a bioreactor (1110) including a tiltable perforated barrier (1112), in accordance with some embodiments of the bioreactors of the present application.
Figure 12B:
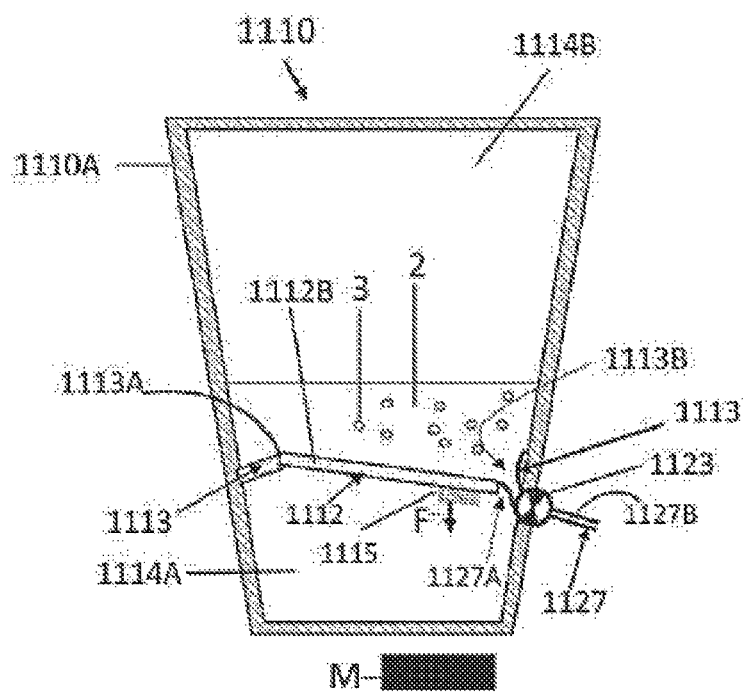

FIGS. 11A-11B are schematic part cross-sectional diagrams illustrating two different states of a bioreactor including a buckling perforated barrier, in accordance with some embodiments of the bioreactors of the present application, and FIGS. 12A-12B are schematic part cross-sectional diagrams illustrating two different states of a bioreactor including a tiltable perforated barrier, in accordance with some embodiments of the bioreactors of the present application. It is noted that, for the sake of clarity of illustration, the schematic drawings of FIGS. 10A-10B, 11A-11B and 12A-12B, illustrate only the general shape of the walls of the bioreactors and the shape and arrangement of the movable or deformable or tiltable or buckling perforated barrier included therein and of the harvesting port associated with the perforated barrier and do not show any details of any additional components of the bioreactors or bioreactor systems (such as, for example, various openings in the walls of the bioreactors, sensor units, fluid inlet ports, fluid outlet ports, draining ports, harvesting ports, heating units, cooling units, fluid impellers, gas dispersing heads, valves, pumps, controllers, self-sealable gaskets, fluid manifolds or any other components) which are not important to understanding the shape of the perforated barriers shown of the bioreactors. It will be appreciated by those skilled in the art that any in such components which not shown in FIGS. 10A-10B, 11A-11B, and 12A-12B can be included in any non mutually exclusive combinations and/or permutations in any of the bioreactors schematically illustrated in FIGS. 0A-10B, 11A-11B, 12A-12B, and 13 as is disclosed in detail herein and as illustrated in the drawing figures.

Turning now to FIGS. 1A-10B, the bioreactor 910 has vessel walls 910A, a deformable perforated barrier 912 is fixedly and sealingly attached to the vessel walls 910A, dividing the space within the bioreactor 910 into a first chamber 914A and a second chamber 914B. The deformable perforated barrier 912 includes multiple perforations as disclosed in detail hereinabove and allows the growth medium 2 to bidirectionally pass there through (from the first chamber 914A to the second chamber 914B, and vice versa) but blocks the passage of cells or organisms there through as is disclosed in detail hereinabove. According to some embodiments, the perforated barrier 912 can be made from a material that is biocompatible for the growing of cells or microorganisms and is also flexible or deformable such that a force applied to the perforated barrier 912 can deform its shape.

The bioreactor 910 further comprises a harvesting port 927 which is a hollow member that includes a valve 923. The harvesting port 927 is sealingly attached to the deformable perforated barrier 912 and opens at the surface 912A into the second chamber 914B. The harvesting port 927 sealingly passes through the vessel walls 910A to exit the bioreactor 910. The harvesting port 927 is a hollow member that has a first rigid (non movable) part (or portion) 927A disposed within the first chamber 914A. The first rigid part 927A sealingly passes through the vessel walls 910A and exits outside the bioreactor 910. The first rigid part 927A has a valve 923 therein for opening or closing the harvesting port 927. According to some embodiments, the harvesting port 927 further comprises a second flexible and/or compressible part (or portion) 927B which is sealingly attached to the first part 927A at one end thereof. The flexible and/or compressible part 927B and the rigid part 927A are connected together to form the hollow member opening to the second chamber 914B at the end of the flexible part 927B which is sealingly attached to the deformable perforated barrier 912 and open at the surface 912A thereof.

It is noted that while the harvesting ports disclosed in some embodiments of the present application are open at the upper surface of the perforated barrier, alternative embodiments can include harvesting ports which are closed or sealed at their end connected to the perforated barrier by a thin sealing membrane (not shown). In such embodiments, when the harvesting port needs to be used for harvesting cells from the second chamber of the bioreactor, the sealing membrane is configured to burst open by either inserting a sharp sterile wire-like instrument through the harvesting port and bursting the sealing membrane, or by inserting a sharp sterile instrument through any of the openings in the top part of the bioreactor into the second chamber and bursting the sealing membrane. Any other mechanical or magnetic mechanisms can also be used for bursting the sealing membrane of such sealed harvesting ports as is known in the art.

According to some embodiments, the bioreactor 910 includes a magnetic member 915 attached to the second compressible (or flexible part) 927B, as illustrated in FIGS. 10A-10B. Alternatively, in accordance with yet another embodiment of the bioreactor 910, the magnetic member 915 is configured to be attached to the deformable perforated barrier 912, in some embodiments near the central part of the perforated barrier 912 (not shown in FIGS. 1A-10B). The magnetic member 915 is configured to be (optionally) shaped like an annular member made from a permanently magnetized material.

For example, the magnetic member 915 can be made from a FeNdB (Iron Neodymium Boron) permanent magnet, a samarium-cobalt permanent magnet or any other magnetic or paramagnetic material known in the art such as, for example, Iron. If necessary, the magnetic member 915 can be coated with, or embedded in a biocompatible material such as, for example, a biocompatible plastic or any suitable biocompatible polymer based material, a biocompatible ceramic layer or any other suitable biocompatible and (in some embodiments) sterilizable material.

Turning now to FIG. 10B, when the cells 3 need to be harvested from the bioreactor 910, an amount of growth medium 2 can be drained from the first chamber 914A of the bioreactor 910 through a suitable outlet port (not shown in FIGS. 10A-10B, for the sake of clarity of illustration, but similar to the outlet port 27 of FIG. 1 or to the outlet port 227 of FIG. 3) as disclosed hereinabove for concentrating the cells 3 in the remaining growth medium 2. A strong magnet M can then be suitably placed near the bioreactor 910 as illustrated in FIG. 10B. The magnet M can be any suitable permanent magnet or an electromagnet known in the art. The placement of the magnet M near the bioreactor 910 exerts a magnetic force represented by the arrows F which is directed towards the magnet M. The force pulls the second part 927B downwards causing the deformable perforated barrier 912 attached to the second compressible part 927 to be also pulled downwards and to deform.

When the magnetic force is acting on the second compressible (or flexible or shortenable) part 927B, the second compressible part 927 is compressed such that it's length shortens, allowing the part of the perforated barrier 912 attached to the second part 927B to move downwards, causing the shape of the perforated barrier to deform into a deformed state (as illustrated in FIG. 10B). The deformation of the deformable perforated barrier 912, results in the perforated barrier 912 assuming a slightly curved shape, such that the upper surface 912A of the perforated barrier 912 in the deformed state can nearly resemble a parabolloidal surface.

Returning to FIG. 10A, the bioreactor 910 is shown with the deformable perforated barrier 912 in a flat non-deformed state. In this non-deformed state, the upper surface 912A of the perforated barrier 912 is substantially planar (flat). In this state the cells 3 can be grown in the second chamber 914B as is described in detail for other bioreactor embodiments disclosed hereinabove.

Returning now to FIG. 10B, the bioreactor 910 is illustrated with the deformable perforated barrier 912 in a deformed state. In this deformed state, the upper surface 912A of the perforated barrier 912 is a curved surface. In this deformed state, the concentrated cells 3 suspended in the growth medium 2 can be harvested by opening the valve 923 of the harvesting port 927 and collecting the cell 3 suspended in the growth medium 2 into a collection vessel 511 as disclosed hereinabove. The concave surface 912A of the curved shape of the deformed perforated barrier 912 can advantageously increase the yield of harvested cells as compared to the yield of harvested cells in a bioreactor having a fixed (non-movable) flat (planar) perforated barrier (such as, for example, the bioreactor 110 of FIG. 2).

Turning now to FIGS. 11A-11B, the bioreactor 1010 has vessel walls 1010A. A buckling perforated barrier 1012 is fixedly and sealingly attached to the vessel walls 1010A, dividing the space within the bioreactor 1010 into a first chamber 1014A and a second chamber 1014B. The buckling perforated barrier 1012 includes multiple perforations as disclosed in detail hereinabove and allows the growth medium 2 to bidirectionally pass there through (from the first chamber 1014A to the second chamber 1014B, and vice versa) but blocks the passage of cells or microorganisms there through as is disclosed in detail hereinabove. According to some embodiments, the buckling perforated barrier 1012 can be made from a stiff but flexible material which is biocompatible for the growing of cells or microorganisms.

According to some embodiments, the perimeter of the buckling perforated barrier 1012 is sealingly attached to the vessel walls 1010A such that in a first stable state of the buckling perforated barrier (illustrated in FIG. 11A), the perforated barrier 1012 is convex in shape and the upper surface 1012A of the perforated barrier 1012 which faces the top part 1010C of the bioreactor 1010 is a convex surface. According to some embodiments, if a force of sufficient magnitude is applied to the buckling perforated barrier 1012, the buckling perforated barrier 1012 will flip into a second stable state (illustrated in FIG. 11B). As compared with the barrier (1012) in FIG. 11A, the barrier (1012) in FIG. 11B is tilted a bit towards the bottom of the bioreactor vessel. In the second state of the perforated barrier 1012, the perforated barrier 1012 is concave in shape and the upper surface 1012A of the perforated barrier 1012 which faces the top part 1010C of the bioreactor 1010 is a concave surface.

According to some embodiments, the buckling perforated barrier 1012 is configured such that it is in a bi-stable configuration in which a transition between the two stable states of the buckling perforated barrier requires the application of sufficient force to the perforated barrier 1012. According to some embodiments, the bioreactor 910 further comprises the harvesting port 927 which is a hollow member that includes a valve 923. The harvesting port 927 is sealingly attached to the buckling perforated barrier 1012 and opens at the upper surface 1012A into the second chamber 1014B. The harvesting port 927 sealingly passes through the vessel walls 1010A to exit the bioreactor 1010. The harvesting port 927 is a hollow member that has a first rigid (non-movable) part (or portion) 927A disposed within the first chamber 1014A.

According to some embodiments, the first rigid part 927A sealingly passes through the vessel walls 1010A and exits outside the bioreactor 1010. The first rigid part 927A has a valve 923 therein for opening or closing the harvesting port 927. According to some embodiments, the harvesting port 927 further comprises a second flexible and/or compressible part (or portion) 927B which is sealingly attached to the first part 927A at an end thereof. According to some embodiments, the flexible and/or compressible part 927B and the rigid part 927A are connected together to form the hollow member opening to the second chamber 1014B at the end of the flexible part 927B which is sealingly attached to the buckling perforated barrier 1012 and open at the surface 1012A thereof.

According to some embodiments, the bioreactor 1010 includes a magnetic member 1015. The magnetic member 1015 is configured to (optionally) have an annular shaped magnetic member attached to the deformable perforated barrier 1012, as illustrated in FIGS. 11A-11B. Alternatively, in accordance with yet another embodiment of the bioreactor 1010, the magnetic member 1015 is configured to be attached to the second compressible (or flexible) part 927B of the harvesting port 927 (this embodiment is not shown in FIGS. 10A-10B). However, the magnetic member 1015 can have any other shape suitable for applying an appropriately downward directed force to the buckling perforated barrier or to the second compressible (or flexible) part 927B of the harvesting port 927 (depending on the part to which the magnetic member 1015 is attached in the above disclosed different alternative embodiments).

According to some embodiments, the magnetic member 1015 can be made from a permanently magnetized material or from a paramagnetic material or from any other magnetizable material as disclosed hereinabove in detail with respect to the magnetic member 1015. If necessary, the magnetic member 1015 can be coated with or embedded in a biocompatible material such as a biocompatible plastic or any suitable biocompatible polymer based material, a biocompatible ceramic layer or any other suitable biocompatible and (in some embodiments) sterilizable material, as disclosed hereinabove with respect to the magnetic member 915.

Turning now to FIG. 11B, when cells (not shown) need to be harvested from the bioreactor 1010, an amount of growth medium (not shown) can be drained from the first chamber 1014A of the bioreactor 1010 through a suitable outlet port (not shown in FIGS. 11A-11B, for the sake of clarity of illustration, but similar to the outlet port 27 of FIG. 1 or to the outlet port 227 of FIG. 3) as disclosed hereinabove for concentrating the cells in the remaining growth medium.

According to some embodiments, a magnet M is configured to then be suitably placed near the bioreactor 1010 as illustrated in FIG. 11B. The magnet M can be any suitable permanent magnet or an electromagnet known in the art, as disclosed in detail with respect to FIG. 10B hereinabove. The placement of the magnet M near the bioreactor 1010 exerts a magnetic force on the magnetic member 1015 represented by the arrows F which is directed towards the magnet M. The force pulls the buckling perforated barrier 1012 downward in the direction represented by the arrows F. According to some embodiments, the magnetic force is of a magnitude that is more than sufficient to cause the buckling perforated barrier 1012 to flip from the first stable (convex) state to the second stable (concave) state (as is illustrated in FIGS. 11A-11B). According to some embodiments, when the perforated barrier 1012 flips from the first state to the second state, the central part of the buckling perforated barrier 1012 moves downwards and causes the second compressible part 927B to be compressed such that the length of the part 927B shortens, allowing the part of the buckling perforated barrier 1012 attached to the second part 927B to move downwards.

According to some embodiments, the flipping of the buckling perforated barrier 1012 from the first state to the second state can also be achieved mechanically using a weal (not shown) or a vertical rod-like pushing/pulling member (not shown) which is configured to be attached at one end thereof to the buckling perforated barrier 1012 while the second end thereof sealingly and slidably passes through a suitable sealing gasket (not shown) disposed in an opening (not Shown) in the top part 1010C of the bioreactor 1010.

According to some embodiments, when the buckling perforated barrier 1012 is in the first state, pushing such a pushing/puling member downwards is configured to flip the buckling perforated barrier 1012 from the first state to the second state. However, it will be appreciated by those skilled in the art that any other mechanical or magnetic or electromagnetic mechanism or combinations of such mechanisms can be used to flip the buckling perforated barrier from the first state into the second state and all such mechanisms or combinations of mechanisms are deemed to be included within the scope of the embodiments of the present application.

In FIG. 11B the bioreactor 1010 is illustrated with the buckling perforated barrier 1012 in the second stable state. In this second state, the upper surface 1012A of the buckling perforated barrier 1012 is a concavely curved surface. In this state, the concentrated cells (not shown) suspended in the growth medium (not shown) within the second chamber 1014B can be harvested by opening the valve 923 of the harvesting port 927 and collecting the cell suspension into a collection vessel (not shown) as disclosed hereinabove. According to some embodiments, the concave surface 1012A of the buckling perforated barrier 1012 in the second stable state can advantageously increase the yield of harvested cells as compared to the yield of harvested cells in a bioreactor having a fixed (non-movable) flat (planar) perforated barrier (such as, for example, the bioreactor 110 of FIG. 2).

Turning now to FIGS. 12A-12B, the bioreactor 1110 has vessel walls 1110A. A tiltable perforated barrier 1112 is sealingly attached to the vessel walls 1110A, dividing the space within the bioreactor 1110 into a first chamber 1114A and a second chamber 1114B. The perimeter of the tiltable perforated barrier 1112 is sealingly attached to a flexible and/or deformable and/or stretchable annular member 1113. Typically, the annular sheet 1113 does not have any perforations therein. The annular member 1113 can be made from a flexible or pliable and/or stretchable material, such as, for example, rubber or latex or a flexible polysilane based thin material and is also sealably attached to the vessel walls 1110A of the bioreactor 1110. In some embodiments, the annular member can be non-permeable to either the cells 3 and to the growth medium 2.

The tiltable perforated barrier 1112 has multiple perforations therein as disclosed in detail hereinabove and allows the growth medium 2 to bi-directionally pass there through (from the first chamber 1114A to the second chamber 1114B and vice versa) but blocks the passage of cells or microorganisms there through as is disclosed in detail hereinabove. According to some embodiments, the perforated barrier 1112 can be (optionally) made from a stiff or rigid material which is biocompatible for the growing of cells or microorganisms.

According to some embodiments, the bioreactor 1110 further comprises the harvesting port 1127 which is a hollow member that includes a valve 1123. A first end 1127A of the harvesting port 1127 is disposed within the first chamber 1114A and is sealingly attached to the annular member 1113 such that the end 1127A opens into the second chamber 1114B through an opening 1113B on the upper surface 1113A of the annular member 1113. The harvesting port 1127 sealingly passes through the vessel walls 1110A to exit the bioreactor 1110. The harvesting port 1127 is a hollow member. A second end 1127B of the harvesting port 1127 is disposed outside the bioreactor 1110 and includes a valve 1123 therein for opening or closing the harvesting port 1127.

According to some embodiments, the bioreactor 1110 also includes a magnetic member 1115. The magnetic member 1115 is configured to (optionally) be a bar shaped magnetic member attached to the perforated barrier 1112 near the perimeter of the perforated barrier 1112, as illustrated in FIGS. 12A-12B. However, the magnetic member 1115 can have any other shape suitable for applying an appropriately downward directed force to the tiltable perforated barrier 1112. When no force is applied to the tiltable perforated barrier 1112, the perforated barrier 1112 is horizontal or nearly horizontal as illustrated in FIG. 12A.

According to some embodiments, the magnetic member 1115 can be made from a permanently magnetized material or from a paramagnetic material or a ferromagnetic material or from any other magnetizable material and can (optionally) be coated with or embedded in a biocompatible material, as disclosed hereinabove in detail with respect to the magnetic member 915.

Turning to FIG. 12B, when the cells 3 need to be harvested from the bioreactor 1110, an amount of growth medium (not shown) can be drained from the first chamber 1114A of the bioreactor 1110 through a suitable outlet port (not shown in FIGS. 12A-12B, for the sake of clarity of illustration, but similar to the outlet port 27 of FIG. 1 or to the outlet port 227 of FIG. 3) as disclosed hereinabove for concentrating the cells in the remaining growth medium 2. A magnet M can be suitably placed near the bioreactor 1110 as illustrated in FIG. 12B. The magnet M can be any suitable permanent magnet or an electromagnet known in the art, as disclosed in detail with respect to FIG. 10B hereinabove.

According to some embodiments, the placement of the magnet M near the bioreactor 1110 exerts a magnetic forte on the magnetic member 1115 represented by the arrow F which is directed towards the magnet M. The magnetic force pulls the side 1112B of the perforated barrier 1112 to which the magnetic member is attached downwards in the direction represented by the arrows F. As a result of the applied magnetic force F, the perforated barrier 1112 is tilted such that the side 1112B of the perforated barrier 1112 is to lower than the side 1112A of the perforated member 1112.

In FIG. 12B, the bioreactor 1110 is illustrated with the perforated barrier 1112 in a tilted state after a magnetic force has been applied by the magnet M to the magnetic member 1115. In this tilted state, the concentrated cells 3 suspended in the growth medium 2 within the second chamber 1114B can be harvested by opening the valve 1123 of the harvesting port 1127 and collecting the cell suspension into a collection vessel (not shown) as disclosed hereinabove. The tilt (relative to the horizon) of the tiltable perforated barrier 1112 can advantageously increase the yield of harvested cells as compared to the yield of harvested cells in a bioreactor having a fixed (non-movable) flat (planar) perforated barrier (such as, for example, the bioreactor 110 of FIG. 2).

It is noted that during operating the bioreactors and bioreactor systems of the present application, a liquid, e.g., a growth medium can be supplied by perfusion (constant replacement of media by recirculation as disclosed in detail), or by fed batch (addition of specific nutrients to the growth medium 2) or by hatch (replacement of the growth medium or part of the growth medium periodically if needed).

According to some embodiments, during harvesting of the cells/microorganisms grown in the bioreactors of the present application, a need may arise to further concentrate the cells being harvested. Such concentrating can be achieved without needing to perform additional actions outside the bioreactor (such as, for example, centrifugation in a centrifuge) which can adversely increase the probability of contaminating the harvested cells by using an inline concentrating filter connected to the harvesting port.

According to some embodiments, washing of the cells in the bioreactors can be done performed by replacing the growth medium 2 with a wash buffer as is known in the art. The replacement of the growth medium 2 can be performed by draining the growth medium 2 from the bioreactor and filling the bioreactor with new wash buffer several times. According to some embodiments, the draining can be performed by using any of the draining ports included in the first (lower) chamber of any of the bioreactors (such as, for example, the outlet port 27 of the bioreactor 10 of FIG. 1, or the outlet port 227 of the bioreactor 210 of FIG. 3) or by using the output ports opening into the second (upper) chamber included in bioreactor embodiments that allow controlling of the level of growth medium in the second chamber of the bioreactors (such as, for example, the outlet port 126D of the bioreactor 110 of FIG. 2).

According to some embodiments, the bioreactors of the present application are configured to allow cell separation and/or cell selection. Cell separation such as magnetic bead binding or antibody binding can be performed inside the second chamber of some embodiments of the bioreactors by using magnetic bead methods as is well known in the at According to some embodiments, magnetic beads (such as, for example magnetic cell specific antibody-coated beads can be inserted into the second chamber through any of the closable openings at the top part of the bioreactors (such as, for example through the opening 110E of the bioreactor 110 of FIG. 2). According to some embodiments, once the cells are bonded to the beads, the beads can be collected by using a magnet as is well known in the art, or by using a large filter that is adapted for selecting between the bead size and cells. Such filters can be positive or negative selectors based on the filter's pore size. For Example, cells attached to beads will not pass the filter whereas native cells not attached to beads will pass through the pores in the filter.

Optionally, according to some embodiments the filter is configured to have an affinity to the beads and can retain the beads and the cells attached to the beads on the filter, while allowing unattached cells to pass through the filter. Alternatively, it is possible to use a "tea hag" shaped enclosure enclosing heads coated with a cell specific antibody that allows free passage of unbound cells through the pores in the "tea bag" but retains any antibody coated beads and the cells that are bonded to the beads within the "tea bag". According to some embodiments, cells can pass through the "tea bag" membrane but the beads are bigger and stay in the bag. According to some embodiments, cells that are attached to the beads can be retained in the "tea bag" and taken out of the bioreactor or can be retained depending on the intended use and application.

According to some embodiments, the bioreactor can further comprise a 3D hollow container (for example but not limited to a column-like container 560) in its upper chamber (demonstrated in FIG. 6A), configured to be used for cell sorting; for a non-limiting example, precipitating CAR-T cells with magnetic beads.

In some embodiments, the upper chamber (second chamber) is configured to comprise an immobilized matrix and or beads in order to select cells or microorganisms having a particular binding activity. In some embodiment, the cells or microorganisms comprised in the fluid, for example but not limited to a growth media or wash media, can be circulated through an inner 3D container comprising the immobilized matrix or beads. In some embodiments, the container walls permit cell and media flow in and out of the container but beads and cells bound to beads or the immobilized matrix are not permitted egress from the container. In some embodiments, the container comprises an immobilized matrix.

In some embodiments, beads comprise an affinity molecule on their surface. In some embodiments, an affinity molecule comprises a polypeptide, or portion thereof or a peptide or a carbohydrate binding molecule. In some embodiments, an affinity molecule comprises an antibody, biotin, avidin, a receptor or part thereof, an agglutinin, a lectin, or any other molecule known in the art to which a cell or microorganism can bind. In some embodiments, the beads comprise magnetic beads. In the case of a magnet, magnetic beads can be retained in the container by positioning a magnet near the container and retaining the positive cells attached to the magnetic heads in the container while circulating back the negative cells.

In some embodiments, an immobilized matrix comprises an affinity molecule on its surface. In some embodiments, an affinity molecule comprises a polypeptide, or portion thereof or a peptide or a carbohydrate binding molecule. In some embodiments, an affinity molecule comprises an antibody, biotin, avidin, a receptor or part thereof, an agglutinin, a lectin, or any other molecule known in the art to which a cell or microorganism can bind.

In some embodiments, cells pass through the container, wherein if the cells or microorganism possess a binding partner to the surface marker present on the beads or immobilized matrix, the cells can bind to the surface of the beads or immobilized matrix and be retained within the container.

In some embodiments, the container comprises a "tea bag" like structure, wherein the sides are configured to be flexible.

According to some embodiments, a material such as Retro-Nectin can be added to the barrier or to the affinity matrix in order to enhance infection rate of viruses, such as retor or lenti virus, as commonly used for CAR T. According to some embodiments, the barrier and/or the affinity matrix can be coated with relevant antibodies.

Activation of cells such as, for example, T cells can be achieved by adding cytokines and activation signals to the growth medium 2 or by co-culturing the T-cells with cytokine secreting cells that can be adhered to the perforated barrier or to any other type of suitable carrier, or adhered to a "tea bag" or floating in a "tea bag" or on magnetic beads, as disclosed hereinabove. Additionally, the activation of T-cells can be performed by co-culturing T-cells with Antigen presenting cells, as is known in the art. It is noted that co-culturing of different types of cells is not limited to cell activation only. For a non-limiting example, anti CD3/CD28 conjugated beads can also be used to activate T cells. In another non-limiting example, Anti CD3 and Anti CD28 antibodies can also be used for activating T cells.

According to some embodiments, the bioreactors of the present application are configured to also be used for co-culturing other types of cells for achieving other results. For example, when culturing embryonic stem cells, the bioreactors of the present application are configured to also be used to co-culture the embryonic stem cells with feeder cells (such as, for example, fibroblasts) which can release into the growth medium substances and/or factors necessary for maintaining growth and proliferation of the stem cells and/or for inducing differentiation of the stem cells.

It is noted that for increasing harvesting efficiency the entire second (upper) chamber of the bioreactors disclosed hereinabove or the upper surface of the perforated barriers included within such bioreactors can be washed by growth medium can be perfused or added to the second chamber of the bioreactors from the top or bottom of the second chamber (such as, for example by adding growth medium through the opening 110E of the bioreactor 110, or trough the opening 10G at the top part 10C of the bioreactor 10 of FIG. 1, or by injecting growth medium through the self-sealing gasket 211 of the bioreactor 210 of FIG. 3 by using a syringe filled with sterile growth medium 2). Such washing of the walls of the second chamber and/or of the perforated barriers can result in pushing the cells towards the opening of any harvesting port opening into the second (upper) chamber of the bioreactor as disclosed hereinabove.

According to some embodiments, cells that are grown within the bioreactors disclosed in the present application can be counted on line and concentrated by using a circulation loop with a conic shaped concentrating filter to allow volume reduction. The cell counting can be performed by indirect measurements such as by using capacitance measurements, optical density measurements, and/or other optical sensors as is well known in the art.

According to some embodiments, the bioreactors of the present application are configured to allow culturing of adherent cells on an attachment surface such as a carrier packed bed or even plenary surfaces above the perforated barrier. Detachment of the cells adhering to the perforated barrier can be performed enzymatically, as is well known in the art. Such enzymatic treatment can also be combined with flushing the attachment surface with growth medium or a wash buffer and/or with applying vibrations to the attachment surface.

Figure 13:
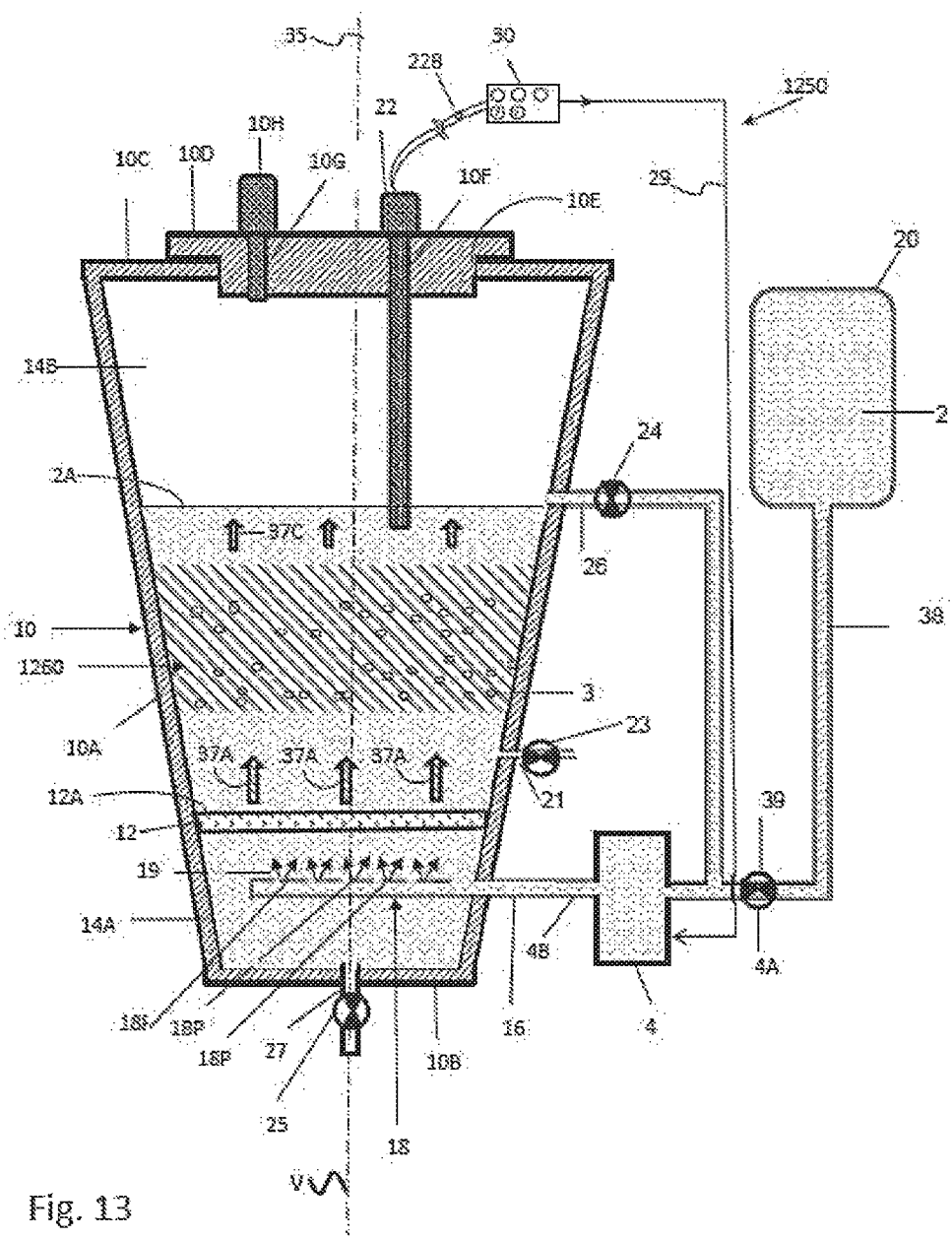
FIG. 13 is a schematic part cross-sectional view illustrating an embodiment of a bioreactor system (1250) comprising a bioreactor (10) having a perforated barrier (12) and a cell carrier matrix (1260)

Reference is now made to FIG. 13 which is a schematic part cross-sectional diagram illustrating a bioreactor system including a bioreactor having a perforated barrier and a cell carrier matrix, in accordance with an embodiment of the bioreactor of the present application. Descriptions of elements presented in FIG. 13 not specifically detailed herein below, are presented in the description of FIG. 1 above.

The bioreactor system 1250 is similar to the bioreactor system 50 of FIG. 1 except that the bioreactor 10 of the bioreactor system 1250 further comprises a supporting matrix 1260 which is disposed within the second chamber 14B. While the supporting matrix 1260 of the system 1250 occupies only a portion of the volume immersed within the growth medium 2, in other embodiments of the bioreactor systems, the supporting matrix is configured to extend up to the surface 2A of the growth medium 2 and can also extend downwards towards the upper surface 12A of the perforated barrier 12. The volume occupied by the support matrix 1260 can depend, inter alia, upon the specific application, the resistance of the cell supporting matrix 1260 to the flow of the growth medium 2, the final amount of required cells or microorganisms and other consideration.

According to some embodiments, the bioreactor system 1250 of the present application is configured to allow culturing of adherent cells on an attachment surface such as, for example, a cell carrier matrix packed bed or even plenary surfaces above the perforated barrier. According to some embodiments, the packed bed of the cell supporting matrix 1260 is configured to be positioned above the perforated barrier 12 of the bioreactor 10 allowing grow medium (or other solutions) to circulate through the immobile (or less mobile) cell supporting matrix 1260 for feeding the cells attached to the surface(s) of the cell supporting matrix 1260.

This arrangement enables constant feeding of the cells attached to the cell supporting matrix 1260, allowing high density cell culturing with a high surface to volume ratio and very low sheer forces while constantly feeding the cells 3. Such cell supporting matrix 1260 can comprise, inter alia, woven and none woven fibers, electrospin-meshes, plastic beads, plastic surfaces, biodegradable materials such as, for example alginate or any other suitable matrices or carriers having two dimensional and/or three dimensional surface(s), as is well known in the art.

According to some embodiments, once there is a need to harvest the cells attached to the cell supporting matrix 1260, the cells 3 can be enzymatically detached from packed the surface(s) of the cell supporting matrix 1260 as is well known in the art. The enzymatic treatment can be combined together with flushing the attachment surface with growth medium or a wash buffer and/or with vibrating of the surface to facilitate detachment of the adhered cells.

According to some embodiments, Enzymatic detachment of adhered cells can be performed by adding one or more enzymes to the growth medium 2 and incubation of the adherent cells in the enzyme containing growth medium for a prescribed time period. Enzymes useful for performing cell detachment can include but are not limited to a protease (such as, for example, trypsin, pepsin or papain) or a suitable collagenase, or any combinations of a collagenase and a protease. Once the cells are harvested from the attachment surface, washing and processing of the cells can be done as described carrier.

Furthermore, in accordance with some embodiments of the bioreactors of the present application, the second (upper) chamber of any of the bioreactors disclosed herein is configured to also include a cell supporting matrix similar to the above disclosed cell supporting matrix 1260 which is configured to be introduced into the second chamber through any of the openings available in the top part of the bioreactors (such as, for example, through the closable opening 110E of the bioreactor 110 of FIG. 2). While growing non-adherent cells in the bioreactors disclosed herein in which the cells are suspended in the growth medium and do not typically adhere to a surface, the bioreactors disclosed herein are configured to also be used for growing adherent cells that require some surface or substrate to adhere to. While such adherent cells can adhere to the perforated barrier of the bioreactor, it can be desirable to increase the surface area available for such adherent cells in order to increase cell yield. Therefore, in accordance with some embodiments of the bioreactors of the present application, any of the bioreactors disclosed herein are configured to include a suitable cell supporting matrix disposed within the second chamber of the bioreactor.

According to some embodiments, the cell supporting matrix can be any type of cell supporting matrix known in the art to which the cells can adhere. For example, the cell supporting matrix can include a collagen based matrix, woven and none woven fibers, electro-spin meshes, plastic (polymer based) beads, plastic (polymer based) particles surfaces, biodegradable materials such as, for example alginate, any type of collagen or any other suitable matrices or cell carriers having two dimensional and/or three dimensional surface(s) with a high surface to volume ratio, as is well known in the art.

It is noted that the bioreactors and bioreactor systems disclosed in the present application are configured to be used for many different applications including, inter alia, the growing of microorganisms like bacteria or any other single cell or multicellular microorganisms, isolated living cells of any type, including but not limited to, living cells from insects, living cells of invertebrates, living cells of vertebrates, living mammalian cells, and various different types of human cells. The total volume, shape and other components and/or characteristics of the various embodiments of the bioreactors and bioreactor systems disclosed hereinabove are configured to be scaled and adapted to each specific application.

According to some embodiments, the bioreactor 1250 is configured to be used to co-culture together adherent and non-adherent suspended cells that need co-culturing were the adherent cells are attached to the cell supporting matrix 1260 and the suspended non-adhering cells are suspended in the medium above the perforated barrier 12 and below the cell supporting matrix 1260. For example the bioreactor 1250 or any other of the bioreactors containing a cell supporting matrix are configured to be used for culturing of embryonic stem cells which are suspended non-adherent cells with feeder cells such as adherent fibroblasts.

One example application of the bioreactors and bioreactor systems is the growing of cells for cell therapy. Cell therapy is an evolving industry where cells are used as therapeutic agents. The cells can be obtained from an autologous source (from the patient) or an allogeneic source (different individual donor). In cases of use of autologous cells, such as immune-cell therapy (using T cells, and/or B cells and/or dendritic cells, and/or natural killer cells) and/or mesenchymal stem cells. The therapeutic dosages can range from several million cells to several billion typically cultured in volumes of a few litters (1-20 L). In allogeneic therapies the bio-manufacturing of the therapeutic agents can reach volumes of up to thousands of litters per bioreactor.

In some of the embodiments of the bioreactors of the present application, providing for adaptive culturing (using variable medium levels) which allow incremental volume changes, media perfusion and refreshments and high density culturing (such as, but not limited to, in the bioreactor 20 of FIG. 2) the working volume and bioreactor size can be advantageously reduced dramatically by about 2-100 fold as compared to prior art bioreactors. For example, a typical bioreactor having a total volume in the range of 1-2 litter can be used for culturing the cells required for autologous therapy. Such relatively small bioreactor volumes can allow the growing of a few billion cells.

According to some embodiments, the ability to use the relatively small bioreactors of the present application can advantageously save space and reduce operating costs significantly in the facility by allowing the use of many small bioreactors in the same workspace, allowing many small bioreactors to share common services (such as, for example, by sharing a central oxygenating supply space, sharing other facilities, such as computers, controllers and/or workspace temperature controlling devices and air conditioning devices and other shareable devices and systems.

It is noted that similar workspace reductions and cost savings can also be obtained in larger bioreactors adapted for use in allogeneic culturing in which larger bioreactor volumes are required. Such allogeneic cell culturing can require using embodiments of the bioreactors disclosed in the present application having bioreactor volumes in the range of 10-1000 liter (with a typical exemplary, but not obligatory, bioreactor volume of about 100 liter).

It is noted that all the above disclosed bioreactor volume ranges in both applications of growing allogeneic cells and/or autologous cells are given by way of example only and are not obligatory. Thus, bioreactors having volumes that are either larger or smaller than the above ranges can also be used in certain applications and are included within the scope of the volumes of the bioreactors of the present application. For example, in some applications such as, for example, growing algae, bacteria or other microorganisms for obtaining biofuels or other products, the volume of any of the bioreactors of the present application are configured to be scaled up to volumes much higher than 1000 liter.

According to some embodiments, the above mentioned washing methods using the above mentioned bioreactors can be applied to any provided cell mass, even if originally incubated in a different bioreactor.

According to some embodiments, the bioreactors' designs as mentioned above, are configured to allow cell washing and formulating in a very gentle and efficient manner without the need of opening the bioreactor chamber or interfering thereto.

According to some embodiments, the bioreactors' designs as mentioned above, are configured to allow continuous, optimal and adaptive cell culturing at changing volumes, feeding schemes, activating, manipulating, washing and formulating, all in a closed and automated bioreactor with minimal sheer force applied onto the cell mass.

It is appreciated that certain features of the bioreactors and systems thereof disclosed herein, which are, for clarity, described in the context of separate embodiments, may also be provided in combination in a single embodiment. Conversely, various features of the bioreactors and systems thereof disclosed herein, which are, for brevity, described in the context of a single embodiment, may also be provided separately or in any suitable sub-combination or as suitable in any other described embodiment of the bioreactors and systems thereof disclosed herein. Certain features described in the context of various embodiments are not to be considered essential features of those embodiments, unless the embodiment is inoperative without those elements.

Although the bioreactors and systems thereof disclosed herein have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present bioreactors and systems thereof disclosed herein. To the extent that section headings are used, they should not be construed as necessarily limiting.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments may be presented in a range format. It should be understood that the description in range format is merely for convenience and brevity and should not be construed as an inflexible limitation on the scope. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

A skilled artisan would appreciate that the term "medium" may encompass in some embodiments any type of growth medium suitable for growing cells (either eukaryotic or prokaryotic) or any other type of unicellular or multi-cellular microorganisms. In some embodiments, the term "medium" comprises any type of solution used for cell or microorganism processing including but not limited to wash buffers, nutrient buffers, enzyme mixtures, selection solutions, and final formulation solutions.

As used herein, in one embodiment the term "about" refers to ±10%. In another embodiment, the term "about" refers to ±9%. In another embodiment, the term "about" refers to ±9%. In another embodiment, the term "about" refers to ±8%. In another embodiment, the term "about" refers to ±7%. In another embodiment, the term "about" refers to ±6%. In another embodiment, the term "about" refers to ±5%. In another embodiment, the term "about" refers to ±4%. In another embodiment, the term "about" refers to ±3%. In another embodiment, the term "about" refers to ±2%. In another embodiment, the term "about" refers to ±1%.

As used herein, the term "optionally" encompasses the meaning that some element "is provided in some embodiments and not provided in other embodiments." Any particular embodiment disclosed herein may include a plurality of "optional" features unless such features conflict.

Additional objects, advantages, and novel features disclosed herein will become apparent to one ordinarily skilled in the art upon examination of the following examples, which are not intended to be limiting. Additionally, various embodiments and aspects disclosed herein as delineated hereinabove and as claimed in the claims section below finds experimental support in the following examples.

EXAMPLES

Figure 14A:
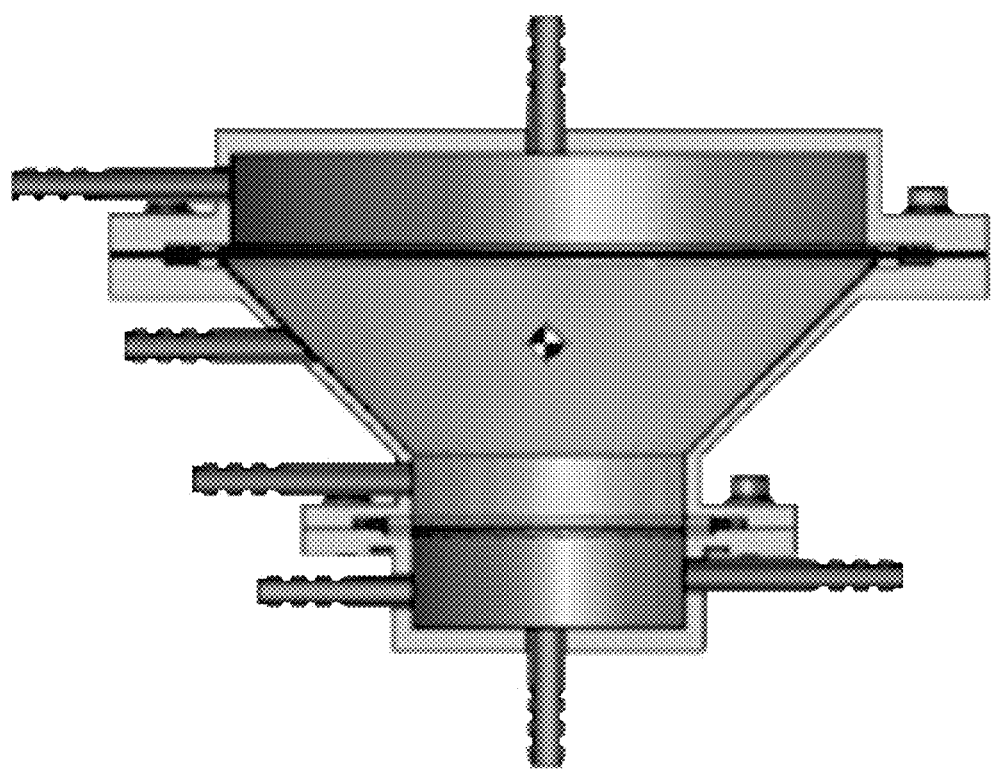
FIGS. 14A-14C show a schematic of an embodiment of a bioreactor used for culturing cells (FIG. 14A) and the growth curves (number of cells versus days) of cells grown using the bioreactor of FIG. 14A.

The bioreactor system used in the following examples included a bioreactor schematically presented in FIG. 14A, which comprises a bioreactor similar to that shown in FIG. 1. The perforated barrier was circular in shape with a 50 $cm^2$ diameter and 1 micrometer thickness. The upper chamber had a conical shape and a 120 $cm^2$ top. The total volume of the growth chamber (upper chamber) was 250 ml. The term "footprint" used herein refers to the lower perforated barrier surface area and total chamber area.

Cells, used to exemplify bioreactor use and effectiveness, were T-lymphocytes, but this in no way should be considered limiting.

The flow rate used in the Examples was about 2-3 mm per mins. This is a representative embodiment of the flow rate for the cells used, wherein the skilled artisan would appreciate that flow rate may change depending on cells used. Thus, the flow rate used in the Examples should in no way be considered limiting. For example, a skilled artisan would appreciate that when culturing larger cells, such as mesenchymal stem cells (MSC), the flow rate may reach 10 mm per minute, and for even larger cells, such as macrophages, flow rate may reach 20 mm (data not shown).

Example 1: Growth of High Density Cell Cultures

Objective: High density culturing of cells.
Methods:
Cells (T cell lymphocytes) were grown on a 50 square cm perforated barrier system with 150 ml media for 7 days, starting at the maximum known cell density for these cells of about 4 million cells per ml. Based on knowledge in the art, this is the density at which these cells would normally be passaged and then maintained at 1 million cells per ml. The media was perfused so the total media used was increased but the volume of media in the chamber remained at 150 ml.
Results:

TABLE 1

| Days | $CM^2$ | Cells(E6/ml) | Total Cells | Cells/cm2 |
|---|---|---|---|---|
| 0 | 50 | 3.580 | 667,000,000 | 13,340,000 |
| 2 | 50 | 5.230 | 784,500,000 | 15,690,000 |
| 4 | 50 | 9.267 | 1,390,050,000 | 27,801,000 |
| 7 | 50 | 24.55 | 3,683,632,500 | 73,672,650 |

The data shows that using a bioreactor disclosed herein, the cells were grown at a density (cells/ml) that is more than 24-fold of the normally expected density for these cells ($1\times10^6$/ml). Similarly, the data shows that growing cells in a bioreactor system having a footprint of 50 $cm^2$, that starting at 13.3 million per $cm^2$ (as opposed to the maximum reported of $10\times10^6/cm^2$), use of a bioreactor described herein resulted in having $73.6\times10^6$ per $cm^2$.

Conclusion: Cells can be grown at high density using a bioreactor comprising a very small footprint (50 $cm^2$) of the culturing system. Thus, the bioreactor provides for a system that allowed optimal and adaptive cell culturing at changing volumes and feeding schemes, allowed for activating, manipulating, feeding, washing, and formulating cells in a closed automated manner with minimal sheer force (See, Examples 2-3 as well). Additional cell incubators or centrifuges are not required for culturing and collection of cells, respectively.

Example 2: Comparison Cell Cultures: Bioreactors vs. Tissue Culture Flasks

Objective: Compare culturing cells in a bioreactor comprising a 50 cm2 perforated barrier with culturing cells in tissue culture flasks.

Methods:

Cells (T cell lymphocytes) were cultured for 14 days in the same dishes as follows: in either a 50 cm² perforated barrier bioreactor system with perfusion, or a T75 flask without media change, or T75 flask with media exchange every 4 days.

Figure 14B:
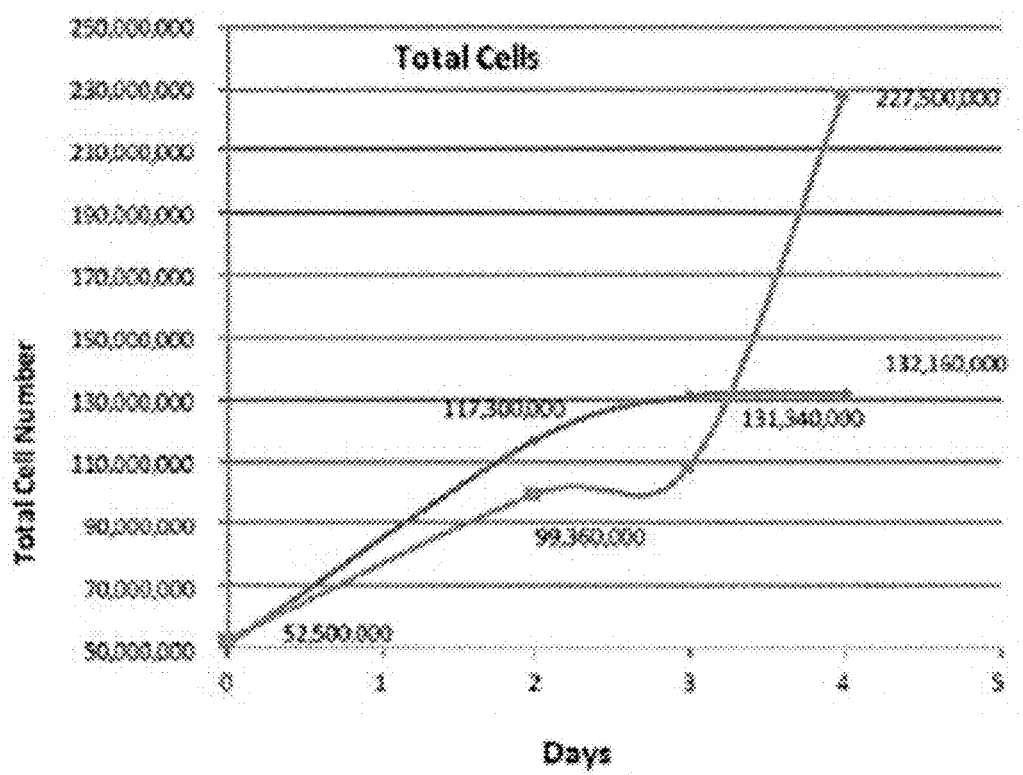
Figure 14C:
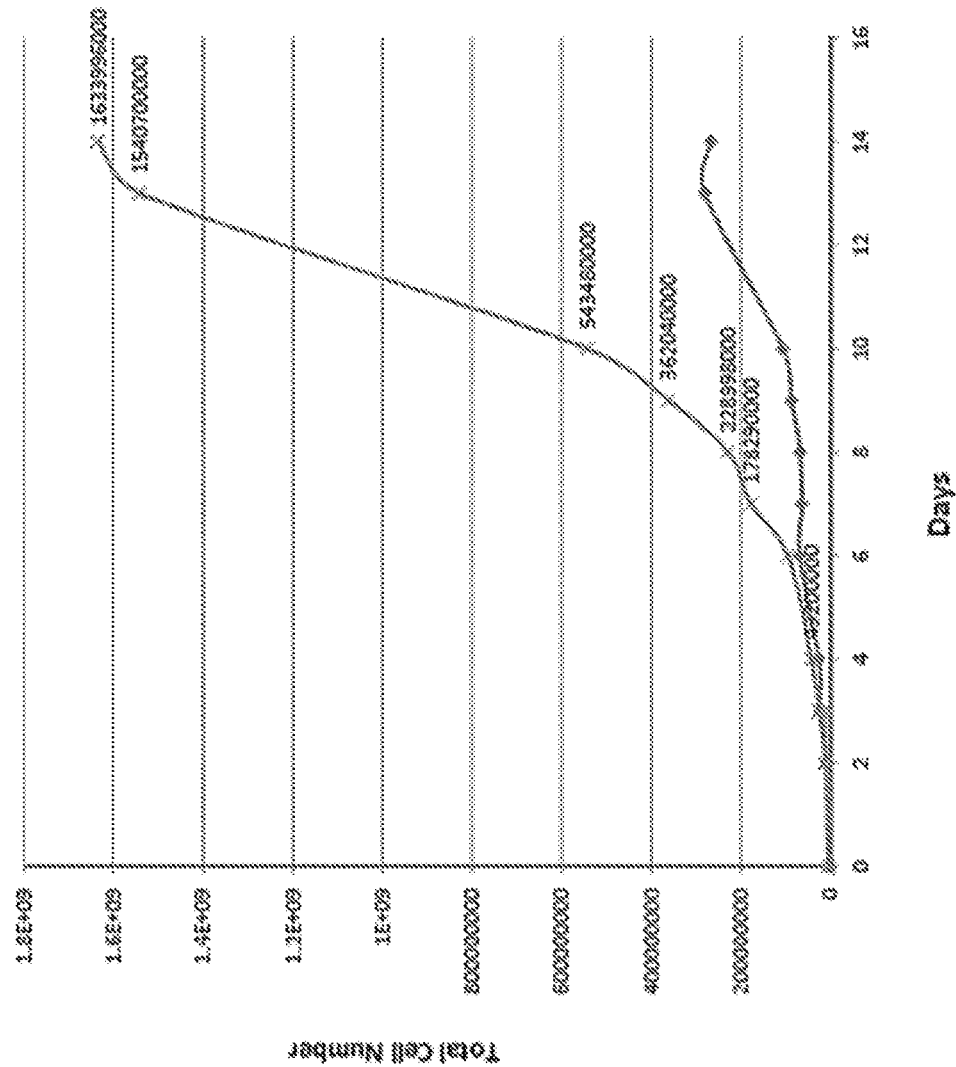

Results:

FIGS. 14B-14C present growth curves from two representative culturing experiments, showing that cells could be continuously grown in a bioreactor system having a 50 cm² perforated barrier without the need to replace media (a pour out/pour in complete exchange), passage or change the container. Further, that cells grown in the closed continuous bioreactor system (yellow) continued to proliferate for at least 14 days, and achieved a total cell number of 1,633, 996,000 cells compared with only about 4,3200,000 cells in the T75 flask without media change (grey), and only about 300,000,000 cells in the T75 flask with media change (blue). The 14-day time frame was used based on the fact that growth of cells in the bioreactor surpassed that in the flasks after a week. Cells can be cultured for more than two weeks in the bioreactor (data not shown).

Conclusion:

Culturing of cells in a bioreactor system described herein is more effective than culturing of cells in flasks even with media exchange.

Example 3: Processing of Cells Grown in a Bioreactor

Objective: Processing of cells (or microorganisms) includes washing the cells, media replacement, and concentrating the cells. These steps are normally accomplished in the prior art by repeated centrifugation and pelleting of the cells. There are two additional technologies known in the art for replacing media which are a TFF (tangential force filtration) centrifugation and a counter flow centrifuge. The objective of this example was to examine cell recovery from a bioreactor as disclosed herein, including the viability of the cells recovered.

Methods:

In the bioreactor system used (demonstrated in FIG. 15A), in order to wash the cells and replace the growth media, the wash buffer was perfused upstream 1510 from the bottom of the bioreactor vessel (lower chamber 1550), wherein the wash buffer flowed through a first perforated barrier 1512 into the upper chamber 1540 and was extracted from the highest valve 1530. This perfusion flow diluted the media until growth media had been replaced by the wash solution. In some embodiments, the valve 1530 can comprise a perforated barrier or a filter (not shown), configured to prevent the cells from leaving the bioreactor (during the liquids change).

At this point, the final formulation media may be perfused through the system, replacing the wash buffer. In addition, in some embodiments, some of the growth media could be drawn-off from the upper chamber (optionally via a second screening perforated barrier (FIG. 15A 1502) configured to prevent the cells from leaving the bioreactor) until a level where the cells are located, thereby reducing the volume and concentrating the cells, before the final formulation media is perfused (FIG. 15A). As demonstrated in FIG. 15A, the provided bioreactor with an inverted frustoconical shape allows the cells (or microorganisms) growing mass to float and to elevate to a larger surface, due to the wash solution upstream flow (against gravity direction) and the pressure equilibrium (mass gravity vs. upstream liquid's flow). Further, due to constant volumetric-flow, a slower flow of the wash solution runs through the cells (or microorganisms) mass 3 at the upper and larger areas of the inverted frusto-conical shape, which assist in concentrating the cells mass, and reduces shear forces applied by the wash solution flow.

Figure 15B:
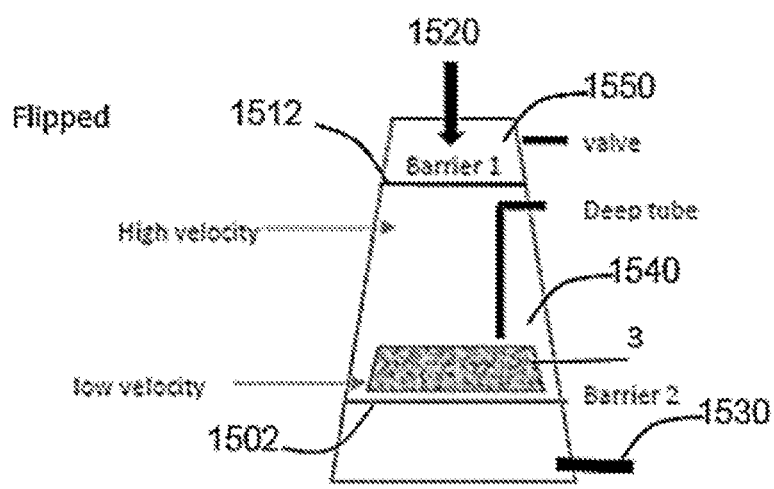

In another embodiment, larger volumes of wash solution can be exchanged with growth media by using a bioreactor with an additional barrier located above the level of the cells (when looking at Hg. 15A) and inverting the bioreactor (as shown in FIG. 15B). The bioreactor vessel is configured to be flipped such that the upper chamber (or what is now the lower chamber 1540) will have perforated barriers both below 1502 and above 1512 the mass of cells. This practically allows more media or wash solution to be downstream perfused due to the larger surface area of the second barrier (barrier 2 in FIG. 15B). A skilled artisan would recognize that more volume on wider surface area results in the same velocity (flow rate) so the cells stay near the second barrier (barrier 2 in FIG. 15B) and larger volumes of cells mass can be washed.

Figure 15C:
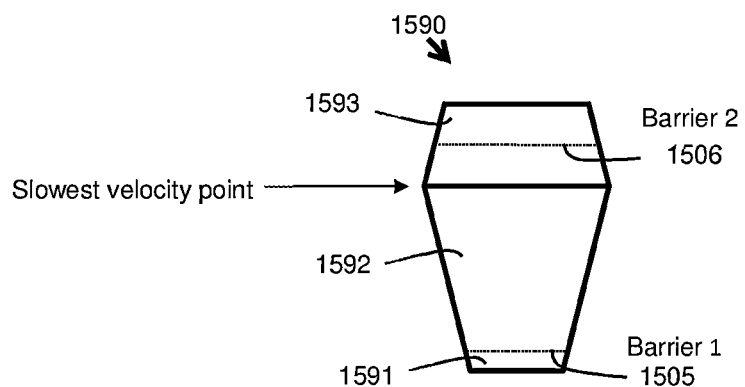
Figure 15D:
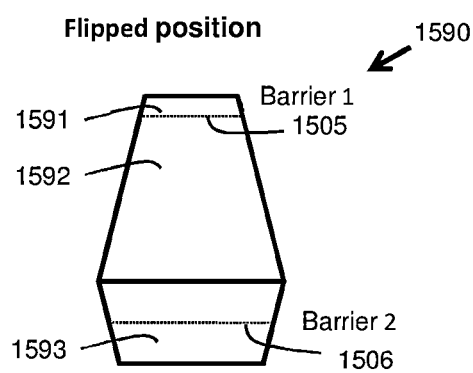
Figure 16:
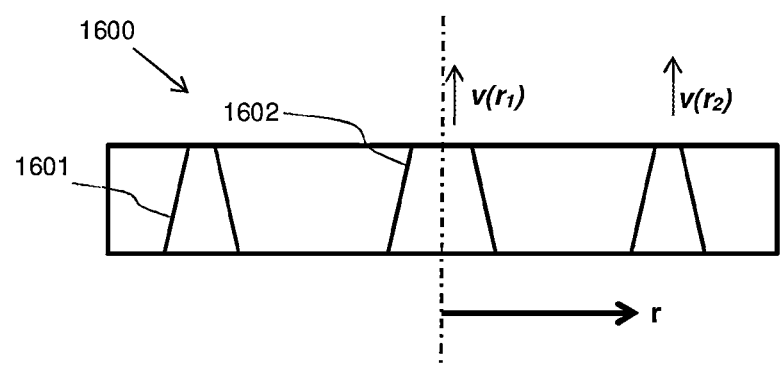
FIG. 16 is a schematic cross-sectional illustrating a perforated barrier configured to control fluid velocity.

FIGS. 15C and 15D demonstrate a bioreactor 1590 comprising a vessel constructed of two frusto-conical parts having same diameter for their wider base, yet their narrower base can comprise a different diameter. The two parts are sited one on top of the other coaxially joined together at their wider (similar) base. The vessel is divided into three chambers by two perforated harriers; a first perforated barrier 1505 and a second (screening) perforated barrier 1506, which are sealingly disposed at the walls of the bioreactors vessel, according to some embodiments. FIG. 15C demonstrates the bioreactor during cell growth stage, where the first lower chamber 1591 (having the narrowest base as its bottom) is configured to be introduced (not shown here) with the growth medium, which flows upstream via the first perforated barrier 1505, and into the second middle chamber 1592 (which was created by the two perforated barrier); the middle chamber is configured to be introduced with (not shown here) and to accommodate the cells. As shown, the second middle chamber 1592 comprises the area with the largest/widest cross-section surface 1595, therefore with the slowest medium's flow rate. According to some embodiments, the aim is not to have the cells pass this largest/widest area, during the growing stage; this could be achieved for example by controlling the medium's flow velocity. Above the widest area a second perforated barrier 1506 is shown, which serves as the bottom of upper third chamber 1593, which is configured to be introduced with a washing medium (not shown here).

FIG. 15D demonstrates the bioreactor 1590 at its flipped or inverted position during a washing stage. During the washing stage, the washing media is introduced to downstream via the third chamber 1593 (not shown) and then down via the cells mass accommodated in the middle chamber 1952 and then drained out via the third chamber 1593. The second perforated barrier 1506 is configured to prevent cells passage; therefore washed cells are retained in the second middle chamber.

According to some embodiments, a bioreactor configuration such as demonstrated in FIGS. 15C and 15D, where one base of the vessel is wider than the other, can serve for growing cells in two steps. In the first step, the growing can start where the smaller base is facing down, as demonstrated in FIG. 15C, with very low amounts of cells, allowed to grow to higher surface areas. In the second step when the cell mass is grown, instead of moving to the cells into a larger chamber of another bioreactor, the bioreactor 1590 can be flipped or inverted to have now the wider base facing down, as shown in FIG. 15D, allowing the cell mass larger surface area and lower medium's flow rates.

The downstream washing/collecting process was tested in an embodiment of a bioreactor with a single perforated harder, wherein three different surface velocities were examined near the perforated barrier: 3.6 mm/min, 1.8 mm/min, and 1.2 mm/min. Following removal of media with a deep tube (FIG. 15A) 15 ml of cells in growth media remained. The total wash volume used was 600 ml, wherein the final volume of liquid comprising the cells was again reduced to 15 ml. Media replacement was performed for 40 cycles (Forty (40)×15 ml washes=600 ml total wash volume). There is not a limit to the volume of media that can be replaced.

Results:

In order to examine the effect of flow rate during exchange of a liquid solution, the volume of liquid used in the downstream washing/collection was maintained but the rate at which the liquid flowed was differed. Thus, an exchange in a shorter time period was a result of a higher flow, and a longer time period was the result of a lower flow rate.

After 30 mins of media exchange at 3.6 mm/min, 60.3% of the cells recovered having viability of 87.8%. After 60 mins of media exchange at 1.8 mm/min, 100% of the cells were recovered having 91% viability. After 90 minutes of media exchange at 1.2 m/min, 100% of the cells were recovered with 92.1% viability.

Conclusion:

Media replacement was comparable to other methods known in the art, such as TFF, which replaces/dilutes 5 volumes. Significantly, using the method described here to wash and collect cells avoids the high flow rate and shear of the continues flow centrifuge (1-2 liters per minute), as the low flow rates used were 1,000 to 10,000 fold lower with much less shear.

While certain features of the bioreactors and systems thereof disclosed herein have been illustrated and described herein, many modifications, substitutions, changes, and equivalents will now occur to those of ordinary skill in the art. It is, therefore, to be understood that the appended claims are intended to cover all such modifications and changes as fall within the true spirit of the bioreactors and systems thereof disclosed herein.

What is claimed is:

1. A method of growing cells, comprising:
   obtaining a bioreactor,
      wherein the bioreactor comprises a closed vessel,
         wherein the closed vessel comprises a first chamber and a second chamber upstream of and in fluid communication with the first chamber,
            wherein the second chamber comprises an increasing transversal cross sectional area from a bottom end of the second chamber adjacent the first chamber to a top end of the second chamber which is opposite the bottom end;
   introducing a plurality of cells into the second chamber;
   introducing a fluid, through a fluid inlet port, into the first chamber,
      wherein the fluid comprises a nutrient;
   flowing the fluid in a first direction, from the first chamber toward the second chamber, through a first plurality of pores, the first plurality of pores aligning the fluid, controlling a velocity of the fluid, and preventing passage of a bubble through the first plurality of pores, to thereby provide an aligned fluid;
   flowing the aligned fluid in only the first direction through a second plurality of pores into the second chamber, the second plurality of pores above the first plurality of pores, the second plurality of pores preventing the plurality of cells in the second chamber from passing from the second chamber into the first chamber;
   decreasing the velocity of the aligned fluid as the fluid flows from the bottom end of the second chamber toward the top end of the second chamber, due to the increasing transversal cross sectional area of the second chamber, to thereby provide a reduced velocity fluid;
   suspending at least some cells of the plurality of cells in the reduced velocity fluid, to thereby provide suspended cells;
   growing the suspended cells with the nutrient, to thereby provide grown cells; and
   removing at least a portion of the reduced velocity fluid, through a fluid outlet port, from the second chamber, to thereby provide a removed fluid.

2. The method of claim 1, further comprising:
   harvesting at least some of the grown cells from the second chamber.

3. The method of claim 1, further comprising:
   harvesting at least some of the grown cells, through a harvesting port, from the second chamber.

4. The method of claim 3, wherein the harvesting port is between the fluid inlet port and the fluid outlet port.

5. The method of claim 1, wherein the first plurality of pores is separated from the second plurality of pores by a gap.

6. The method of claim 1,
   wherein a diameter of each of the pores of the first plurality of pores is from 0.1 to 40 micrometers, and
   wherein a diameter of each of the pores of the second plurality of pores is
      greater than the diameter of each of the pores of the first plurality of pores, and less than 1 millimeter.

7. The method of claim 1, wherein at least some of the pores of the second plurality of pores are conical.

8. The method of claim 1, wherein a shape of the transversal cross sectional area comprises at least one of a circle, an ellipse, and a polygon.

9. The method of claim 1, further comprising:
   heating the fluid prior to introducing the fluid into the first chamber, through the fluid inlet port.

10. The method of claim 1, further comprising:
    cooling the fluid prior to introducing the fluid into the first chamber, through the fluid inlet port.

11. The method of claim 1, further comprising:
    reintroducing at least a portion of the removed fluid, through the fluid inlet port, back into the first chamber.

12. The method of claim 1, wherein removing at least the portion of the reduced velocity fluid comprises pumping at least the portion of the reduced velocity fluid through the fluid outlet port, from the second chamber, to thereby provide the removed fluid, and
    wherein the method further comprises:
       recirculating at least a portion of the removed fluid, through the fluid inlet port, back into the first chamber.

13. The method of claim 1, wherein removing at least the portion of the reduced velocity fluid comprises pumping at least the portion of the reduced velocity fluid through the fluid outlet port, from the second chamber, to thereby provide the removed fluid, and wherein the method further comprises:
adding at least one additional fluid to the removed fluid, to thereby provide a supplemented fluid; and
pumping the supplemented fluid, through the inlet port, into the first chamber, with a pump.

14. The method of claim 13, wherein the pump comprises an impeller.

15. The method of claim 13, wherein the at least one additional fluid comprises a gas.

16. The method of claim 15, wherein the gas comprises oxygen.

17. The method of claim 13, wherein the at least one additional fluid comprises an additional nutrient.

18. The method of claim 1, further comprising:
sensing at least one property of the reduced velocity fluid; and
introducing a second fluid, into the fluid inlet port, based on the sensed property.

19. The method of claim 1, wherein the first plurality of pores are formed within a first barrier, and wherein the second plurality of pores are formed with a second barrier.

20. The method of claim 19, wherein the first barrier is offset from the second barrier by a gap between the first barrier and the second barrier.

21. A method of growing cells, comprising:
obtaining a bioreactor,
wherein the bioreactor comprises a closed vessel,
wherein the closed vessel comprises a first chamber and a second chamber upstream of and in fluid communication with the first chamber;
introducing a plurality of cells into the second chamber;
introducing a fluid, through a fluid inlet port, into the first chamber,
wherein the fluid comprises a nutrient;
flowing the fluid in a first direction, from the first chamber toward the second chamber, through a first plurality of pores, the first plurality of pores aligning the fluid, controlling a velocity of the fluid, and preventing passage of a bubble through the first plurality of pores, to thereby provide an aligned fluid;
flowing the aligned fluid in the first direction through a second plurality of pores into the second chamber, the second plurality of pores above the first plurality of pores, the second plurality of pores preventing the plurality of cells in the second chamber from passing from the second chamber into the first chamber;
decreasing the velocity of the aligned fluid as the fluid flows from a bottom end of the second chamber toward a top end of the second chamber, due to an increasing cross sectional area of the second chamber, to thereby provide a reduced velocity fluid;
suspending at least some cells of the plurality of cells in the reduced velocity fluid, to thereby provide suspended cells;
growing the suspended cells with the nutrient, to thereby provide grown cells; and
removing at least a portion of the reduced velocity fluid, through a fluid outlet port, from the second chamber, to thereby provide a removed fluid.

22. The method of claim 21, further comprising:
harvesting at least some of the grown cells from the second chamber.

23. The method of claim 21, further comprising:
harvesting at least some of the grown cells, through a harvesting port, from the second chamber.

24. The method of claim 21, wherein the first plurality of pores is separated from the second plurality of pores by a gap.

25. The method of claim 21,
wherein a diameter of each of the pores of the first plurality of pores is from 0.1 to 40 micrometers, and
wherein a diameter of each of the pores of the second plurality of pores is
greater than the diameter of each of the pores of the first plurality of pores, and less than 1 millimeter.

26. The method of claim 21, wherein at least some of the pores of the second plurality of pores are conical.

27. The method of claim 21, wherein a shape of the cross sectional area of the chamber comprises at least one of a circle, an ellipse, and a polygon.

28. The method of claim 21, further comprising:
sensing at least one property of the reduced velocity fluid; and
introducing a second fluid, into the fluid inlet port, based on the sensed property.

29. The method of claim 21,
wherein the first plurality of pores are formed within a first barrier, and
wherein the second plurality of pores are formed with a second barrier.

30. The method of claim 29, wherein the first barrier is offset from the second barrier by a gap between the first barrier and the second barrier.

* * * * *